US010463668B2

(12) United States Patent
Byrd et al.

(10) Patent No.: US 10,463,668 B2
(45) Date of Patent: Nov. 5, 2019

(54) METHODS OF TREATING AND PREVENTING GRAFT VERSUS HOST DISEASE

(71) Applicant: Pharmacyclics LLC, Sunnyvale, CA (US)

(72) Inventors: John C. Byrd, Columbus, OH (US); Jason A. Dubovsky, Columbus, OH (US); Natarajan Muthusamy, Columbus, OH (US); Amy J. Johnson, Columbus, OH (US); David Miklos, Stanford, CA (US)

(73) Assignee: Pharmacyclics LLC, Sunnyvale, CA (US)

( * ) Notice: Subject to any disclaimer, the term of this patent is extended or adjusted under 35 U.S.C. 154(b) by 0 days.

(21) Appl. No.: 15/586,058

(22) Filed: May 3, 2017

(65) Prior Publication Data

US 2018/0078555 A1  Mar. 22, 2018

Related U.S. Application Data

(63) Continuation of application No. 14/523,650, filed on Oct. 24, 2014, now Pat. No. 9,795,604.

(60) Provisional application No. 61/973,173, filed on Mar. 31, 2014, provisional application No. 61/973,176, filed on Mar. 31, 2014, provisional application No. 61/910,945, filed on Dec. 2, 2013, provisional application No. 61/895,981, filed on Oct. 25, 2013.

(51) Int. Cl.
| A61K 31/519 | (2006.01) |
| A61K 38/13 | (2006.01) |
| A61K 31/5377 | (2006.01) |
| A61K 31/56 | (2006.01) |
| A61P 35/00 | (2006.01) |
| A61P 35/02 | (2006.01) |
| A61P 43/00 | (2006.01) |
| A61K 35/17 | (2015.01) |
| A61K 45/06 | (2006.01) |
| A61K 35/28 | (2015.01) |

(52) U.S. Cl.
CPC ........ *A61K 31/519* (2013.01); *A61K 31/5377* (2013.01); *A61K 31/56* (2013.01); *A61K 35/17* (2013.01); *A61K 38/13* (2013.01); *A61K 45/06* (2013.01); *A61P 35/00* (2018.01); *A61P 35/02* (2018.01); *A61P 43/00* (2018.01); *A61K 35/28* (2013.01)

(58) Field of Classification Search
CPC .... A61K 31/5377; A61K 31/56; A61K 38/13; A61K 31/519; A61K 35/17; A61K 35/28; A61K 45/06; A61P 35/00; A61P 35/02; A61P 43/00
See application file for complete search history.

(56) References Cited

U.S. PATENT DOCUMENTS

| 6,303,652 | B1 | 10/2001 | Uckun et al. |
| 6,326,469 | B1 | 12/2001 | Ullrich et al. |
| 6,506,769 | B2 | 1/2003 | Snow et al. |
| 6,660,744 | B1 | 12/2003 | Hirst et al. |
| 6,753,348 | B2 | 6/2004 | Uckun et al. |
| 6,770,639 | B2 | 8/2004 | Snow et al. |
| 6,921,763 | B2 | 7/2005 | Hirst et al. |
| 7,514,444 | B2 | 4/2009 | Honigberg et al. |
| 7,625,880 | B2 | 12/2009 | Jankowski et al. |
| 7,732,454 | B2 | 6/2010 | Verner |
| 8,008,309 | B2 | 8/2011 | Honigberg et al. |
| 8,067,395 | B2 | 11/2011 | Jankowski et al. |
| 8,088,781 | B2 | 1/2012 | Honigberg et al. |
| 8,476,284 | B2 | 7/2013 | Honigberg et al. |
| 8,501,751 | B2 | 8/2013 | Honigberg et al. |
| 8,552,010 | B2 | 10/2013 | Honigberg et al. |
| 8,697,711 | B2 | 4/2014 | Honigberg et al. |
| 8,790,662 | B2 | 7/2014 | Spellberg et al. |
| 8,987,421 | B2 | 3/2015 | Chang et al. |
| 9,522,917 | B2 | 12/2016 | Izumi et al. |
| 9,655,857 | B2 | 5/2017 | Chong et al. |
| 9,795,604 | B2 | 10/2017 | Byrd et al. |
| 10,010,507 | B1 | 7/2018 | Chong et al. |
| 10,213,386 | B2 | 2/2019 | Chong et al. |
| 2002/0016460 | A1 | 2/2002 | Snow et al. |
| 2003/0035833 | A1 | 2/2003 | He |
| 2003/0040461 | A1 | 2/2003 | McAtee |
| 2003/0118078 | A1 | 6/2003 | Carlson et al. |
| 2003/0125235 | A1 | 7/2003 | Foxwell |
| 2004/0006083 | A1 | 1/2004 | Hirst et al. |
| 2005/0008640 | A1 | 1/2005 | Waegell et al. |

(Continued)

FOREIGN PATENT DOCUMENTS

| CN | 101674834 A | 3/2010 |
| JP | 2010504324 A | 2/2010 |

(Continued)

OTHER PUBLICATIONS

Devillier et al., "TLI in refractory chronic GVHD", 2013, Bone Marrow Transplantation, 48, pp. 854-858. (published online Dec. 10, 2012). (Year: 2013).*

(Continued)

*Primary Examiner* — My-Chau T. Tran
(74) *Attorney, Agent, or Firm* — Foley Hoag LLP

(57) ABSTRACT

Described herein are methods for treating and preventing graft versus host disease using ACK inhibitors. The methods include administering to an individual in need thereof an ACK inhibitor such as ibrutinib for treating and preventing graft versus host disease.

4 Claims, 18 Drawing Sheets

Specification includes a Sequence Listing.

(56) References Cited

U.S. PATENT DOCUMENTS

| | | | |
|---|---|---|---|
| 2005/0084905 | A1 | 4/2005 | Prescott et al. |
| 2005/0090499 | A1 | 4/2005 | Currie et al. |
| 2005/0101604 | A1 | 5/2005 | Currie et al. |
| 2005/0153990 | A1 | 7/2005 | Watkins |
| 2005/0196851 | A1 | 9/2005 | Uckun |
| 2005/0209255 | A1 | 9/2005 | Jimenez et al. |
| 2006/0079494 | A1 | 4/2006 | Santi et al. |
| 2006/0167090 | A1 | 7/2006 | Uckun et al. |
| 2008/0076921 | A1 | 3/2008 | Honigberg et al. |
| 2008/0108636 | A1 | 5/2008 | Honigberg et al. |
| 2008/0139582 | A1 | 6/2008 | Honigberg et al. |
| 2009/0181987 | A1 | 7/2009 | Honigberg et al. |
| 2010/0004270 | A1 | 1/2010 | Honigberg et al. |
| 2010/0022561 | A1 | 1/2010 | Honigberg et al. |
| 2010/0041677 | A1 | 2/2010 | Honigberg et al. |
| 2012/0053189 | A1 | 3/2012 | Loury |
| 2012/0071497 | A1 | 3/2012 | Buggy et al. |
| 2012/0088912 | A1 | 4/2012 | Honigberg et al. |
| 2012/0184013 | A1 | 7/2012 | Honigberg et al. |
| 2013/0178483 | A1 | 7/2013 | Buggy et al. |
| 2015/0086507 | A1 | 3/2015 | Izumi et al. |
| 2015/0118209 | A1 | 4/2015 | Byrd et al. |
| 2015/0140085 | A1 | 5/2015 | Goldstein |
| 2015/0157634 | A1 | 6/2015 | Blazar et al. |
| 2016/0022683 | A1* | 1/2016 | Fardis ............... A61K 45/06 424/736 |
| 2016/0256397 | A1 | 9/2016 | Chong et al. |
| 2016/0287592 | A1* | 10/2016 | Chang ............... A61K 31/519 |
| 2018/0078555 | A1 | 3/2018 | Byrd et al. |
| 2018/0078558 | A1 | 3/2018 | Blazar et al. |

FOREIGN PATENT DOCUMENTS

| | | |
|---|---|---|
| JP | 2013527249 A | 6/2013 |
| WO | WO-1997/028161 A1 | 8/1997 |
| WO | WO-2000/56737 A2 | 9/2000 |
| WO | WO-2001/019829 A2 | 3/2001 |
| WO | WO-2001/019829 A3 | 3/2001 |
| WO | WO-2001/25238 A2 | 4/2001 |
| WO | WO-2001/041754 A2 | 6/2001 |
| WO | WO-2001/044258 A1 | 6/2001 |
| WO | WO-2002/38797 A2 | 5/2002 |
| WO | WO-2002/076986 A1 | 10/2002 |
| WO | WO-2002/080926 A1 | 10/2002 |
| WO | WO-2003/000187 A2 | 1/2003 |
| WO | WO-2004/096253 A1 | 11/2004 |
| WO | WO-2004/100868 A2 | 11/2004 |
| WO | WO-2004/100868 A3 | 11/2004 |
| WO | WO-2005/005429 A1 | 1/2005 |
| WO | WO-2005/014599 A1 | 2/2005 |
| WO | WO-2008/039218 A2 | 4/2008 |
| WO | WO-2008/054827 A2 | 5/2008 |
| WO | WO-2008/121742 A2 | 10/2008 |
| WO | WO-2010/0068806 A1 | 6/2010 |
| WO | WO-2011/153514 A2 | 12/2011 |
| WO | WO-2012/171007 A2 | 12/2012 |
| WO | WO-2013/059738 A2 | 4/2013 |
| WO | WO-2013/177596 A2 | 11/2013 |
| WO | WO-2015/061751 A1 | 4/2015 |
| WO | WO-2015/084857 A1 | 6/2015 |

OTHER PUBLICATIONS

Yalniz et al., "Steroid Refractory Chronic Graft-Versus-Host Disease: Cost-Effectiveness Analysis", 2017, Biology of Blood and Marrow Transplantation, 24(9), pp. 1920-1927. (Year: 2018).*
Waller et al., "Ibrutinib for Chronic Graft-versus-Host Disease After Failure of Prior Therapy: 1-Year Update of a Phase 1 b/2 Study", 2019 (Available online Jun. 2019), Biology of Blood and Marrow Transplantation, pp. 1-6 (Article in Press). (Year: 2019).*
Arnold et al. Pyrrolo[2,3-d]pyrimidines Containing an Extended 5-Substituent as Potent and Selective Inhibitors of Ick 1. Bioorg. Med. Chem. Ltrs. 10:2167-2170 (2000).
Brown, "PCI-32765, the First BTK (Bruton's Tyrosine Kinase) Inhibitor in Clinical Trials," Curr Hematol Malig Rep, 8(1): 1-6 (2013).
Browning. B cells move to centre stage: novel opportunities for autoimmune disease treatment. Nature Reviews/Drug Discovery 5:564-576 (Jul. 2006).
Burchat et al. Pyrazolo[3,4-d]pyrimidines Containing an Extended 3-Substituent as Potent Inhibitors of Lck—a Selectivity Insight. Bioorg. Med. Chem. Ltrs. 12:1687-1690 (2002).
Burger et al. High-Level Expression of the T-Cell Chemokines CCL3 and CCL4 by Chronic Lymphocytic Leukemia B Cells in Nurselike Cell Cocultures and After BCR Stimulation. Blood 113(13):3050-3058 (2008).
Cetkovic-Cvrlje et al., "Dual targeting of Bruton's tyrosine kinase and Janus kinase 3 with rationally designed inhibitors prevents graft-versus-host disease (GVHD) in a murine allogeneic bone marrow transplantation model," Br J Haematol, 126(6): 821-827 (2004).
Chang et al., "The Bruton tyrosine kinase inhibitor PCI-32765 ameliorates autoimmune arthritis by inhibition of multiple effector cells," Arhtritis Res Ther, 13:R115 (2011).
Co-pending U.S. Appl. No. 14/523,650, filed Oct. 24, 2014.
Co-pending U.S. Appl. No. 14/558,297, filed Dec. 2, 2014.
Cohen et al. Structural Bioinformatics-Based Design of Selective, Irreversible Kinase Inhibitors. Science 308:1318-1321 (May 27, 2005).
Desiderio. Role of Btk in B cell development and signaling. Curr. Op. in Immunology 1997, 9:534-540.
Dorwald, F.Z., "Side Reactions in Organic Synthesis," Wiley:VCH, Weinheim p. IX of Preface, Wiley-VCH Verlag GmbH & C KGaA (2005).
Dubovsky et al., "Ibrutinib can reverse established chronic graft-versus-host disease, which is dependent upon IL-2 inducible T-cell kinase (ITK) and Bruton's tyrosine kinase (BTK)-driven lymphocyte activation," Cancer Res, 74(19): 2591 (2014).
Dubovsky et al., "Ibrutinib Treatment Ameliorates Murine Chronic Graft-Versus-Host Disease," J Clin Invest, 124(11): 4867-4876 (2014).
European Search Report and Written Opinion for European Application No. EP 06850386.1 dated Sep. 10, 2010.
European Search Report for European Application No. EP 06850039 dated Feb. 9, 2010.
European Search Report for European Application No. EP 10155834.4 dated May 19, 2010.
European Search Report for European Application No. EP 14856623.5 dated Jun. 16, 2017.
European Search Report for European Application No. EP 14867905 dated Mar. 31, 2017.
Filipovich et al., "National Institutes of Health Consensus Development Project on Criteria for Clinical Trials in Chronic Graft-versus-Host Disease: I. Diagnosis and Staging Working Group Report," Biol Blood Marrow Tr, 11(12): 945-956 (2005).
Flynn et al., "Therapeutic treatment of multi-organ system, obstructive pulmonary and scleradermatous chronic graft-versus-host disease with the BTK and ITK inhibitor Ibrutinib," J Immunol, 192(1): TRAN3P-873 (2014).
Fruman. Xid-like Phenotypes: A B Cell Signalosome Takes Shape. Immunity 13:1-3 (Jul. 2000).
Gold. To make antibodies or not:signaling by the B-cell antigen receptor. Trends in Pharmacological Sciences, 23(7):316-324 (Jul. 2002).
Honigberg et al. The Bruton tyrosine kinase inhibitor PCI-32765 blocks B-cell activation and is efficacious in models of autoimmune disease and B-cell malignancy. PNAS USA 107:13075-13080 (2010).
Horwood et al. Bruton's Tyrosine Kinase Is Required for Lipopolysaccharide-induced Tumor Necrosis Factor α Production. J. Exp. Med. 197(12):1603-1611 (Jun. 2003).
International Preliminary Report on Patentability for International Application No. PCT/US2014/062277 dated Apr. 26, 2016.
International Preliminary Report on Patentability for International Application No. PCT/US2014/068177 dated Jun. 7, 2016.
International Search Report and Written Opinion for International Application No. PCT/US2010/052377 dated Jun. 29, 2011.

(56) References Cited

OTHER PUBLICATIONS

International Search Report and Written Opinion for International Application No. PCT/US2014/062277 dated Jan. 30, 2015.
International Search Report and Written Opinion for International Application No. PCT/US2014/068177 dated Feb. 27, 2015.
International Search Report for International Application No. PCT/US2006/049626 dated Apr. 9, 2008.
Iwaki et al. Btk Plays a Crucial Role in the Amplification of FceRI-mediated Mast Cell Activation by Kit. J. Biol. Chem. 280(48):40261-40270 (Dec. 2, 2005).
Jacobson et al., "B-cell-directed therapy for chronic graft-versus-host disease," Haematologica, 95(11): 1811-1813 (2010).
Jefferies et al., "Bruton's tyrosine kinase is a toll/interleukin-1 receptor domain-binding protein that participates in nuclear factor kB activation by toll-like receptor 4," J Biol Chem, 278:26258-64 (2003).
Kapur et al., "B-cell involvement in chronic graft-versus-host disease," Haematologica, 93(11): 1702-1711 (2008).
Kawakami et al. Terreic acid, a quinone epoxide inhibitor of Bruton's tyrosine kinase. PNAS USA 96:2227-2232 (1999).
Kuppers. Mechanisms of B-cell lymphoma pathogenesis. Nature Reviews/Cancer 5:251-262 (2005).
Kurosaki. Functional dissection of BCR signaling pathways. Curr. Op. Imm. 12:276-281 (2000).
Lehmann, "Pathogenesis and treatment of immune-mediated neuropathies," Adv Neurol Disord, 2(4): 261-281 (2009).
Luskova et al. Modulation of the Fce Receptor I Signaling by Tyrosine Kinase Inhibitors: Search for Therapeutic Targets of Inflammatory and Allergy Diseases. Curr. Pharmaceutical Design 10:1727-1737 (2004).
Magenau et al., "Advances in understanding the pathogenesis of graft-versushost disease", 2016, British Journal of Haematology, vol. 173, Issue 2, pp. 190-205.
Mahajan et al. Rational Design and Synthesis of a Novel Anti-leukemic Agent Targeting Bruton's Tyrosine Kinase (BTK), LFM-A13 [a-Cyano-β-Methyl-N-(2,5-Dibromophenyl)Propenamide]. J. of Biol. Chem. 274(14):9587-9599 (1999).
Mangla et al., "Pleiotropic consequences of Bruton tyrosine kinase deficiency in myeloid lineages lead to poor inflammatory responses," Blood, 104(4):1191-1197 (2004).
Merged Markush Service Search, Jun. 27, 2005.
Miklos, Safety and Efficacy of Ibrutinib in Patients with Relapsed/Refractory (R/R) Chronic Lymphocytic Leukemia (CLL)/Small Lymphocytic Lymphoma (SLL) Who Have Undergone Prior Allogeneic Stem Cell Transplant. 2015 BMT Tandem Meetings (Feb. 11-15, San Diego, California).
Min, "The pathophysiology of chronic graft-versus-host disease: the unveiling of an enigma," Korean J Hematol, 46(2): 80-87 (2011).
Niiro et al. Regulation of B-Cell Fate by Antigen-Receptor Signals. Nature Reviews 2:945-956 (2002).
Nisitani et al. In situ detection of activated Bruton's tyrosine kinase in the Ig signaling complex by phosphopeptide-specific monoclonal antibodies. PNAS USA 96:2221-2226 (1999).
Oligino et al. Targeting B cells for the treatment of rheumatoid arthritis. Arthritis Res. Ther., 5(Suppl.4):S7-S11 (2002).
Pan et al., "Discovery of selective irreversible inhibitors for Bruton's tyrosine kinase," ChemMedChem, 2:58-61 (2007).
Pharmacyclics, Inc. Safety and efficacy study of Bruton's tyrosine kinase inhibitor in subjects with relapsed or refractory diffuse large B-cell lymphoma. In: ClinicalTrials.gov [Internet]. Bethesda (MD): National Library of Medicine (US). Feb. 2, 2011—[cited Nov. 22, 2013]. Available from: http://clinicaltrials.gov/ct2/show/NCT01325701 NLM Identifier: NCT01325701.
Pharmacyclics, Inc. Study of the Bruton's Tyrosine Kinase Inhibitor in Subjects With Chronic Graft Versus Host Disease. In: ClinicalTrials.gov [Internet]. Bethesda (MD): National Library of Medicine (US). Jul. 11, 2014 [cited Feb. 5, 2015] Available from: https://clinicaltrial.gov/ct2/show/NCT02195869?term=NCT02195869 NLM Identifier: NCT02195869.
Ponader et al. The Bruton tyrosine kinase inhibitor PCI-32765 thwarts chronic lymphocytic leukemia cell survival and tissue homing in vitro and in vivo. Blood (Epub Dec. 16, 2011), 119(5):1182-1189 (Feb. 2012).
Quek et al. A role for Bruton's tyrosine kinase (Btk) in platelet activation by collagen. Curr. Biol. 8(20):1137-1140 (1998).
Ryan et al. Ibrutinib Treatment of Relapsed CLL Following Allogeneic Transplantation: Sustained Disease Response and Promising Donor Immune Modulation—Abstract submission to 56th ASH Annual Meeting and Exposition (Dec. 6-9, 2014).
Sada et al. Protein-Tyrosine Kinases and Adaptor Proteins in FceRI-Mediated Signaling in Mast Cells. Curr. Mol. Med. 3(1):85-94 (2003).
Schaeffer et al. Tec family kinases in lymphocyte signaling and function. Curr. Op. Imm. 12:282-288 (2000).
Science IP CAS Search, Mar. 16, 2006.
Science IP CAS Search, Sep. 5, 2006.
Shaffer et al. Lymphoid malignancies: the dark side of B-cell differentiation. Nature Reviews/Immunology 2:920-932 (2002).
Smaill et al., "Tyrosine kinase inhibitors. 15. 4-(phenylamino)quinazoline and 4-(phenylamino)pyrido[d]pyrimidine acrylamides as irreversible inhibitors of the ATP binding site of the epidermal growth factor receptor," J Med Chem, 42(10):1803-15 (1999).
Smith et al., "The Tec family of cytoplasmic tyrosine kinases: mammalian Btk, Bmx, Itk, Tec, Txk and homologs in other species," BioEssays, 23:436-46 (2001).
Smolen et al. Therapeutic Strategies for Rheumatoid Arthritis. Nature Reviews 2:473-488 (2003).
Srinivasan et al., "Donor B-cell alloantibody deposition and germinal center formation are required for the decelopment of murine chronic GVHD and bronchiolitis obliterans," Blood, 119(6): 1570-1580 (2012).
Taiwan Search Report for TW103136912 dated Nov. 13, 2015.
The Journal of Pharmacy, 21 (2), 37-46, 2005.
Treister, "How we treat oral chronic graft-versus-host disease," Blood, 120: 3407-3418 (2012).
Uckun et al. The Anti-leukemic Bruton's Tyrosin Kinase Inhibitor a-cyano-β-hydroxy-β-mehyl-N-(2,5-dibromophenyl)Propenamide (LFM-A13)Prevents Fatal Thromboembolism. Leuk. Lymphoma 44(9):1569-1577 (2003).
Uckun et al., "Bruton's tyrosine kinase as a molecular target in treatment of leukemias and lymphomas as well as inflammatory disorders and autoimmunity," Expert Opin Ther Pat, 20(11):1-14 (2010).
Uckun et al., "Btk as a mediator of radiation-induced apoptosis in DT-40 lymphoma B cells," Science, 273(5278):1096-100 (1996).
Uckun et al., "In vivo pharmacokinetic features, toxicity profile, and chemosensitizing activity of alpha-cyano-beta-hydroxy-beta-methyl-N-(2,5-dibromophenyl)propenamide (LFM-A13), a novel antileukemic agent targeting Bruton's tyrosine kinase," Clin Cancer Res, 8(5):1224-33 (2002).
Vassilev et al. Bruton's Tyrosine Kinase as an Inhibitor of the Fas/CD95 Death-inducing Signaling Complex. J. Biol. Chem. 274(3):1646-1656 (1999).
Vassilev et al. Therapeutic Potential of Inhibiting Bruton's Tyrosine Kinase, (BTK). Current Pharmaceutical Design 10:1757-1766 (2004).
Vippagunta et al. Crystalline Solids, Advanced Drug Delivery Reviews, 48:3-26 (2001).
Xu et al., "Oral administration of ibrutinib is ineffective at preventing sclerodermain chronic GVHD in two preclinical mouse models," Poster 56th ASH Annual Meeting and Exposition (Dec. 6-9, 2014).
Yamamoto et al. The Orally Available Spleen Tyrosine Kinase Inhibitor 2-[7-(3,4-Dimethoxyphenyl)-imidazo[1,2-c]pyrimidin-5-ylamino]-nicotinamide Dihydrochloride (BAY61-3606) Blocks Antigen-Induced Airway Inflammation in Rodents. J. Pharma. And Exp. Therapeutics 306(3):1174-1181 (2003).
Bernstein, "Polymorphism—A Perspective," Crystal Growth & Design, 11: 632-650 (2011).
Byrd et al., "A randomized, multicenter, open-label, phase III study of the Bruton tyrosine kinase (BTK) inhibitor ibrutinib (PCI-32765) versus ofatumumab in patients (pts) with relapsed or refractory

(56) References Cited

OTHER PUBLICATIONS (RR) chronic lymphocytic leukemia (CLL)/small lymphocytic lymphoma (SLL): Resonate," J Clin Oncol, 31(15) (2013).
Byrn et al., "Pharmaceutical Solids: A Strategic Approach to Regulatory Considerations," Pharmaceutical Research, 12: 945-954 (1995).
Calderwood et al., "Pyrrolo[2,3-d]pyrimidines Containing Diverse N-7 Substituents as Potent Inhibitors of Lcks," Bioorg Med Chem Lett, 12: 1683-1686 (2002).
Castor et al., "The Role of Chemokines in Mediating Graft Versus Host Disease: Opportunities for Novel Therapeutics," Frontiers in Pharmacology, 3: 1-13, 1 (Feb. 2012).
Chenson et al., "Novel Targeted Agents and the Need to Refine Clinical End Points in Chronic Lymphocytic Leukemia," Journal of Clinical Oncology, 30(23):2820-2822 (2012).
Ciric et al., "Clonal Evolution in Waldenström macroglobulinemia Highlights Functional Role of B-Cell Receptor," Blood, 97: 312-232 (2001).
De Rooij et al., "The Clinically Active BTK Inhibitor PCI-32765 Targets B-Cell Receptor and Chemokine Controlled Adhesion and Migration in Chronic Lymphocytic Leukemia," Blood, 119(11):2590-2594 (2012).
Fry et al., "Specific Irreversible Inactivation of the Epidermal Growth Factor Receptor and erbB2, by a New Class of Tyrosine Kinase Inhibitor," Proc Natl Acad Sci, 95: 12022-12027 (1998).
Good et al., "Classification of non-Hodgkin's Lymphoma," Hematol Oncol Clin N Am, 22: 781-805 (2008).
Gu et al., "Polymorph Screening: Influence of Solvent on the Rate of Solvent-Mediated Polymorphic Transformation," Journal of Pharmaceutical Sciences 90, 11: 1878-1890 (2001).
Herman et al., "Bruton Tyrosine Kinase Represents a Promising Therapeutic Target for Treatment of Chronic Lymphocytic Leukemia and is Effectively Targeted by PCI-32765," Blood, 117(23):6287-6296 (2013).
Honigberg et al., "The Bruton Tyrosine Kinase Inhibitor PCI-32765 Blocks B-Cell Activation and is Efficacious in Models of Autoimmune Disease and B-Cell Malignancy," PNAS, 107(29):13075-13080 (2010).
International Conference on Harmonisation of Technical Requirements for Registration of Pharmaceuticals for Human Use-Specifications: Test Procedures and Acceptance Criteria for New Drug Substances and New Drug Products: Chemical Substances (1999).
Morissette et al., "High-throughput Crystallization: Polymorphs, Salts, Co-Crystals and Solvates of Pharmaceutical Solids," Advanced Drug Delivery Review, 56: 275-300 (2004).
Pollyea et al., "A Phase I Dose Escalation Study of the Btk Inhibitor PCI-32765 in Relapsed and Refractory B Cell Non-Hodgkin Lymphoma and Use of a Novel Fluorescent Probe Pharmacodynamics Assay," Blood, 114(22): Abstract No. 3713 (Nov. 20, 2009).
Smaill et al., "Irreversible Inhibitors of the Epidermal Growth Factor Receptor: 4-(Phenylamino)quinazoline- and 4-(Phenylamino)pyrido[3,2-d]pyrimidine-6-acrylamides Bearing Additional Solubilizing Functions," J Med Chem, 43: 1380-1397 (2000).
Uckun, "Clinical Potential of Targeting Bruton's Tyrosine," Int'l Revs Immunology, 27: 43-69 (2008).
Winer et al., "PCI-32765: A Novel Bruton's Tyrosine Kinase Inhibitor for the Treatment of Lymphoid Malignancies," Expert Opin. Investig. Drugs, 3:1-7 (2012).
Woyach et al., "The B-Cell Receptor Signaling Pathway as a Therapeutic in CLL," Blood, 120(6):1175-1184 (2012).
"FDA expands ibrutinib indications to chronic GVHD," FDA.gov, last visited May 24, 2019.
Aalipour et al., "Bruton Tyrosine Kinase Inhibitors: A Promising Novel Targeted Treatment for B Cell Lymphomas," British Journal of Haematology, 163:436-443 (2013).
Betts et al., "Anti-IL6-receptor-alpha (tocilizumab) does not inhibit human monocyte-derived dendritic cell maturation or alloreactive T-cell responses," Blood, 118(19):5340-5343 (2011).
Buggy et al., "Bruton Tyrosine Kinase (BTK) and Its Role in B-cell Malignancy," International Reviews of Immunology, 31:119-132 (2012).
Choi et al., "Pathogenesis and management of graft-versus-host disease," Immunol Allergy Clin N Am, 30:75-101 (2010).
Dignan et al., "Diagnosis and management of chronic graft-versus-host disease," British Journal of Haematology, 158:46-61 (2012).
Dubovsky et al., "Ibrutinib is an irreversible molecular inhibitor of ITK driving a Th1-selective pressure in T lymphocytes," Blood, 112(15):2539-2549 (2013).
Ferrara et al., "Chapter 16: Cellular Therapy for Hematology Malignancies: Allogeneic Hematopoietic Stem Transplantation, Graft-Versus-Host Disease, and Graft Versus Leukemia Effects," Advances in Stem Cell Research, 303-366 (2012).
Ferrara et al., "Graft-versus-host disease," The Lancet, 373:1550-1561 (2009).
Henden et al., "Cytokines in Graft-versus-Host Disease," The Journal of Immunology, 194:4604-4612 (2015).
Imbruvica® Label Prescribing Information dated Jan. 2019.
Kitko et al., "Combination therapy for graft-versus-host disease prophylaxis with etanercept an extracorporeal photopheresis: Results of a Phase II clinical trial," Biol Blood Marrow Transplant, 22:862-868 (2016).
Kitko et al., "Plasma CXCL9 elevations correlate with chronic GVHD diagnosis," Blood, 123(5):786-793 (2014).
Kobbe et al., "Treatment of severe steroid refractory acute graft-versus-host disease with infliximab, a chimeric human/mouse antiTNFα antibody," Bone Marrow Transplantation, 28:47-49 (2001).
Lee, "New approaches for preventing and treating chronic graft-versus-host disease," Blood, 105(11):4200-4206 (2005).
Levine et al., "Etanercept plus methylprednisolone as initial therapy for acute graft-versus-host disease," Blood, 111(4):2470-2475 (2008).
MacMillan et al., "A phase 2/3 multicenter randomized clinical trial of ABX-CBL versus ATG as secondary therapy for steroid-resistant acute graft-versus-host disease," Blood, 109(6):2657-2662 (2007).
Martin et al., "Evaluation of mycophenolate mofetil for initial treatment of chronic graft-versus-host disease," Clinical Trials and Observations, Blood, 113(21):5074-5082 (2009).
Martin et al., "Treatment of chronic graft-versus-host disease: Past, present and future," The Korean Journal of Hematology, 46(3):153-163 (2011).
McIver et al., "Rituximab administration within 6 months of T cell-depleted allogeneic SCT is associated with prolonged life-threatening cytopenias," Biol Blood Marrow Transplant, 16:1549-1556 (2010).
Miklos et al., "Ibrutinib for chronic graft-versus-host disease after failure of prior therapy," Blood, 130(21):2243-2250 (2017).
Musumeci, "FDA Approves Ibrutinib to Treat Chronic Graft Versus Host Disease," Lymphoma.org, (2017) last visited Jun. 24, 2019.
NCI Staff, "Ibrutinib Relieves Chronic Graft-Versus-Host Disease Symptoms," National Cancer Institute, 1-4, (2017) last visited Jun. 24, 2019.
Pavletic et al., "Are we making progress in GVHD prophylaxis and treatment?" Hematology, 251-264 (2012).
Reddy et al., "Graft-versus-host disease and graft-versus-leukemia responses," Hematology,1650-1668 (2018).
Shimabukuro-Vornhagen et al., "Response: Friend of foe in GVHD: a matter of targeting the right B-cell subset," Blood, 115(12):2558-2559 (2010).
Stewart, "Health Canada Oks Imbruvica for Treating Chronic Graft-Versus-Host Disease," Lymphoma News Today, 1-2, (2017) last visited May 24, 2019.
Van Den Akker et al., "The BTK inhibitor LFM-A13 is a potent inhibitor of Jak2 kinase activity," Biol Chem, 385:409-413 (2004).
Yoon et al., "Effects of pravastatin on murine chronic graft-versus-host disease," Transplantation, 90(8):853-860 (2010).
Zorn et al., "Bruton's tyrosine kinase is dispensable for the Toll-like receptor-mediated activation of mast cells," Cellular Signalling, 21:79-86 (2009).
Jagasia et al., "Classic and overlap chronic graft-versus-host disease (cGVHD) is associated with superior outcome after extracorporeal photopheresis (ECP)," Biol Blood Marrow Transplant, 15(10:1288-1295 (2009).

(56) References Cited

OTHER PUBLICATIONS

Shimabukuro-Vornhagen et al., "The role of B cells in the pathogenesis of graft-versus-host disease," Blood, 114(24):4919-4927 (2009).
Pavletic et al., "Measuring Therapeutic Response in Chronic Graft-versus-Host Disease: National Institutes of Health Consensus Development Project on Criteria for Clinical Trials in Chronic Graft-versus-Host Disease: IV. Response Criteria Working Group Report," Biology of Blood and Marrow Transplantation, 12(3): 252-266 (2006).
Ponader et al., "The Bruton Tyrosine Kinase Inhibitor PCI-32765 Thwarts Chronic Lymphocytic Leukemia Cell Survival and Tissue Homing in Vitro and in Vivo," Blood, 119(5):1182-1189 (2012).
Uckun et al. Bruton's Tyrosine Kinase (BTK) as a Dual-Function Regulator of Apoptosis. Biochem. Pharmacology 56:683-691 (1998).

\* cited by examiner

Chronic Graft Versus Host Disease Scoring

| Coat | | Skin | | Weight | | Posture | |
|---|---|---|---|---|---|---|---|
| Score | Description | Score | Description | Score | Description | Score | Description |
| 0 | No hair loss | 0 | No sclerodermatous lesions | 0 | No weight loss or overall weight gain | 0 | No posture defect |
| 1 | Ruffled hair with a small amount of hair loss | 1 | Red or irritated skin lesion | 1 | Weight loss <5% | 1 | Mild hunched posture |
| 2 | Hair loss in a single area <1cm² | 2 | Skin flaking/peeling single lesion | 2 | Weight loss >5% but <10% | 2 | Moderate hunched posture |
| 3 | Hair loss in a single area >1cm² | 3 | Scabbing or bleeding in a single area | 3 | Weight loss >10% but <15% | 3 | Severely hunched posture |
| 4 | Complete hair loss or >1 area involved | 4 | Scabbing or bleeding in multiple areas | 4 | Weight loss >15% | | |

| Posture | | Mobility | | Vitality | |
|---|---|---|---|---|---|
| Score | Description | Score | Description | Score | Description |
| 0 | No posture defect | 0 | Full mobility | 0 | Live |
| 1 | Mild hunched posture | 1 | Slowed gait | 10 | Dead |
| 2 | Moderate hunched posture | 2 | Slowed gait: reticent to move when touched | Instructions: Score each category for each individual mouse. Total score is the summation of all individual scores. In the event of a dead mouse total should = 10 | |
| 3 | Severely hunched posture | 3 | Immobility when touched | | |

D

E

A

B

C

D

E

METHODS OF TREATING AND PREVENTING GRAFT VERSUS HOST DISEASE

CROSS-REFERENCE

This application is a continuation of U.S. application Ser. No. 14/523,650, filed Oct. 24, 2014, now U.S. Pat. No. 9,795,604, issued Oct. 24, 2017, which claims the benefit of priority of U.S. Provisional Application No. 61/895,981, filed Oct. 25, 2013; U.S. Provisional Application No. 61/910,945, filed Dec. 2, 2013; U.S. Provisional Application No. 61/973,173, filed Mar. 31, 2014; and U.S. Provisional Application No. 61/973,176 filed Mar. 31, 2014, each of which are hereby incorporated by reference in their entireties as if fully set forth herein.

SEQUENCE LISTING

The instant application contains a Sequence Listing which has been submitted in ASCII format via EFS-Web and is hereby incorporated by reference in its entirety. Said ASCII copy, created on Oct. 25, 2017, is named PIR-88502_Sequence_Listing and is 674 bytes in size.

BACKGROUND OF THE INVENTION

Chronic graft versus host disease (cGVHD) is the most common long-term complication following allogeneic stem cell transplant (SCT), affecting 30-70% of patients who survive beyond the first 100 days. cGVHD and its associated immune deficiency have been identified as a leading cause of non-relapse mortality (NRM) in allogeneic SCT survivors. SCT survivors with cGVHD are 4.7 times as likely to develop severe or life-threatening health conditions compared with healthy siblings, and patients with active cGVHD are more likely to report adverse general health, mental health, functional impairments, activity limitation, and pain than allo-SCT survivors with no history of cGVHD. Any organ system can be affected, and further morbidity is frequently caused by long-term exposure to the corticosteroids and calcineurin inhibitors required to treat the condition.

SUMMARY OF THE INVENTION

Disclosed herein, in some embodiments, are methods of preventing the occurrence of graft versus host disease (GVHD) or reducing the severity of GVHD occurrence in a patient requiring cell transplantation comprising administration of a therapeutically effective amount of an ACK inhibitor (e.g., an ITK or BTK inhibitor). In some embodiments, disclosed herein are methods of reducing the severity of GVHD occurrence in a patient requiring cell transplantation comprising administration of a therapeutically effective amount of an ACK inhibitor (e.g., an ITK or BTK inhibitor). In some embodiments the ACK inhibitor is a compound of Formula (A). In some embodiments, disclosed herein are methods of preventing the occurrence of graft versus host disease (GVHD) or reducing the severity of GVHD occurrence in a patient requiring cell transplantation, comprising administration of a therapeutically effective amount of a compound of Formula (A) having the structure:

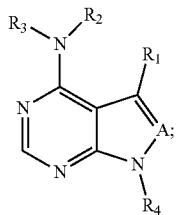

Formula (A)

wherein:

A is N;

$R_1$ is phenyl-O-phenyl or phenyl-S-phenyl;

$R_2$ and $R_3$ are independently H;

$R_4$ is $L_3$-X-$L_4$-G, wherein, $L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;

X is optional, and when present is a bond, —O—, —C(=O)—, —S—, —S(=O)—, —S(=O)$_2$—, —NH—, —NR$_9$—, —NHC(O)—, —C(O)NH—, —NR$_9$C(O)—, —C(O)NR$_9$—, —S(=O)$_2$NH—, —NHS(=O)$_2$—, —S(=O)$_2$NR$_9$—, —NR$_9$S(=O)$_2$—, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl-, aryl-, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;

$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;

or $L_3$, X and $L_4$ taken together form a nitrogen containing heterocyclic ring;

G is wherein,

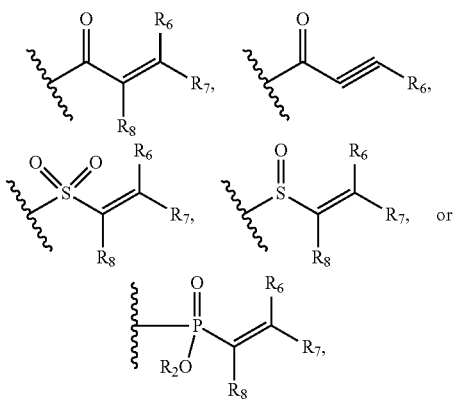

$R_6$, $R_7$ and $R_8$ are independently selected from among H, halogen, CN, OH, substituted or unsubstituted alkyl or substituted or unsubstituted heteroalkyl or substituted or unsubstituted cycloalkyl, substituted or unsubstituted heterocycloalkyl, substituted or unsubstituted aryl, substituted or unsubstituted heteroaryl;

each $R_9$ is independently selected from among H, substituted or unsubstituted lower alkyl, and substituted or unsubstituted lower cycloalkyl;

each $R_{10}$ is independently H, substituted or unsubstituted lower alkyl, or substituted or unsubstituted lower cycloalkyl; or two $R_{10}$ groups can together form a 5-, 6-, 7-, or 8-membered heterocyclic ring; or $R_{10}$ and $R_{11}$ can together form a 5-, 6-, 7-, or 8-membered heterocyclic ring; or each $R_{11}$ is independently selected from H or substituted or unsubstituted alkyl; or a pharmaceutically acceptable salt thereof. In some embodiments, $L_3$, X and $L_4$ taken together form a nitrogen containing heterocyclic ring. In some embodiments, the nitrogen containing heterocyclic ring is a piperidine group. In some embodiments, G is

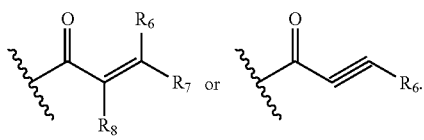

In some embodiments, the compound of Formula (A) is 1-[(3R)-3-[4-amino-3-(4-phenoxyphenyl)pyrazolo[3,4-d]pyrimidin-1-yl]piperidin-1-yl]prop-2-en-1-one. In some embodiments, the patient has cancer. In some embodiments, the patient has a hematological malignancy. In some embodiments, the patient has a relapsed or refractory hematological malignancy. In some embodiments, the patient has a B-cell malignancy. In some embodiments, the patient has a T-cell malignancy. In some embodiments, the patient has a leukemia, a lymphoma, or a myeloma. In some embodiments, the B-cell malignancy is a non-Hodgkin's lymphoma. In some embodiments, the B-cell malignancy is chronic lymphocytic leukemia (CLL). In some embodiments, the B-cell malignancy is a relapsed or refractory B-cell malignancy. In some embodiments, the B-cell malignancy is a relapsed or refractory non-Hodgkin's lymphoma. In some embodiments, the B-cell malignancy is a relapsed or refractory CLL. In some embodiments, the patient has high risk CLL. In some embodiments, the patient has a 17p chromosomal deletion. In some embodiments, the patient has 10%, 20%, 30%, 40%, 50%, 60%, 70%, 80%, 90%, or greater CLL as determined by bone marrow biopsy. In some embodiments, the patient has received one or more prior anticancer agents. In some embodiments, the anticancer agent is selected from among alemtuzumab, bendamustine, bortezomib, CAL-101, chlorambucil, cyclophosphamide, dexamethasone, docetaxel, doxorubicin, endostatineverolimus, etoposide, fludarabine, fostamatinib, hydroxydaunorubicin, ibritumomab, ifosphamide, lenalidomide, mesalazine, ofatumumab, paclitaxel, pentostatin, prednisone, rituximab, temsirolimus, thalidomide, tositumomab, vincristine, or a combination thereof. In some embodiments, the anticancer agent is rituximab. In some embodiments, the anticancer agent is alemtuzumab. In some embodiments, the anticancer agent is fludarabine, cyclophosphamide, and rituximab (FCR). In some embodiments, the anticancer agent is oxaliplatin, fludarabine, cytarabine, rituximab (OFAR). In some embodiments, the amount of the ACK inhibitor compound (e.g., a compound of Formula (A)) prevents or reduces GVHD while maintaining a graft-versus-leukemia (GVL) reaction effective to reduce or eliminate the number of cancerous cells in the blood of the patient. In some embodiments, the cell transplantation is a hematopoietic cell transplantation. In some embodiments, the GVHD is acute GVHD. In some embodiments, the GVHD is chronic GVHD. In some embodiments, the GVHD is sclerodermatous GVHD. In some embodiments, the GVHD is steroid resistant GVHD. In some embodiments, the GVHD is cyclosporin-resistant GVHD. In some embodiments, the GVHD is refractory GVHD. In some embodiments, the GHVD is oral GVHD. In some embodiments, the oral GVHD is reticular oral GVHD. In some embodiments, the oral GVHD is erosive oral GVHD. In some embodiments, the oral GVHD is ulcerative oral GVHD. In some embodiments, the oral GVHD is GVHD of the oral cavity. In some embodiments, the oral GVHD is GVHD of the oropharyngeal region. In some embodiments, the oral GVHD is GVHD of the pharyngeal region. In some embodiments, the oral GVHD is GVHD of the esophageal region. In some embodiments, the oral GVHD is acute oral GVHD. In some embodiments, the oral GVHD is chronic oral GVHD. In some embodiments, the patient exhibits one or more symptoms of GVHD. In some embodiments, the patient has or will receive an allogeneic bone marrow or hematopoietic stem cell transplant. In some embodiments, the ACK inhibitor compound (e.g., a compound of Formula (A)) is administered concurrently with an allogeneic bone marrow or hematopoietic stem cell transplant. In some embodiments, the ACK inhibitor compound (e.g., a compound of Formula (A)) is administered prior to an allogeneic bone marrow or hematopoietic stem cell transplant. In some embodiments, the ACK inhibitor compound (e.g., a compound of Formula (A)) is administered subsequent to an allogeneic bone marrow or hematopoietic stem cell transplant. In some embodiments, the patient is a candidate for receiving HLA-mismatched hematopoietic stem cells. In some embodiments, the patient is a candidate for receiving unrelated donor hematopoietic stem cells, umbilical vein hematopoietic stem cells, or peripheral blood stem cells. In some embodiments, the ACK inhibitor compound (e.g., a compound of Formula (A)) is administered orally. In some embodiments, the ACK inhibitor compound (e.g., a compound of Formula (A)) is administered at a dosage of between about 0.1 mg/kg per day to about 100 mg/kg per day. In some embodiments, the ACK inhibitor compound (e.g., a compound of Formula (A)) is administered at a dosage of about 40 mg/day, about 140 mg/day, about 280 mg/day, about 420 mg/day, about 560 mg/day, or about 840 mg/day. In some embodiments, the ACK inhibitor compound (e.g., a compound of Formula (A)) is administered in combination with other prophylactic agents. In some embodiments, the ACK inhibitor compound (e.g., a compound of Formula (A)) is administered from day 1 to about day 120 following allogeneic bone marrow or hematopoietic stem cell transplant. In some embodiments, the ACK inhibitor compound (e.g., a compound of Formula (A)) is administered from day 1 to about day 1000 following allogeneic bone marrow or hematopoietic stem cell transplant. In some embodiments, the ACK inhibitor compound (e.g., a compound of Formula (A)) is administered in combination with one or more additional therapeutic agents. In some embodiments, the additional therapeutic agent is a corticosteroid. In some embodiments, the therapeutic agent is cyclosporine (CSA), mycophenolate mofetil (MMF) or a combination thereof. In some embodiments, the patient has or will receive a donor lymphocyte infusions (DLI). In some embodiments, the patient is administered one or more DLIs. In some embodiments, the patient is administered two or more DLIs. In some embodiments, the DLI comprises CD3+ lymphocytes. In some embodiments, the patient is administered one or more donor lymphocyte infusions (DLI) following an allogeneic bone marrow or hematopoietic stem cell transplant. In some embodiments, the ACK inhibitor compound (e.g., a compound of Formula (A)) is administered concurrently with a DLI following allogeneic bone marrow or hematopoietic stem cell transplant. In some embodiments, the ACK inhibitor compound (e.g., a compound of Formula (A)) is administered prior to a DLI following an allogeneic bone marrow or hematopoietic stem cell transplant. In some embodiments, the ACK inhibitor compound (e.g., a compound of Formula (A)) is administered following a DLI following an allogeneic bone marrow or hematopoietic stem cell transplant. In some embodiments, the ACK inhibitor compound (e.g., a compound of Formula (A)) is ibrutinib.

Disclosed herein, in some embodiments, are methods of treating a patient for alleviation of a bone marrow mediated disease, comprising administering to the patient allogeneic hematopoietic stem cells and/or allogeneic T-cells, and a therapeutically effective amount of an ACK inhibitor (e.g., an ITK or BTK inhibitor). In some embodiments, disclosed herein are methods of treating a patient for alleviation of a bone marrow mediated disease, with alleviation of consequently developed graft versus host disease (GVHD), comprising administering to the patient allogeneic hematopoietic stem cells and/or allogeneic T-cells, and a therapeutically effective amount of a compound of Formula (A):

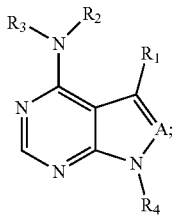

Formula (A)

wherein:

A is N;

$R_1$ is phenyl-O-phenyl or phenyl-S-phenyl;

$R_2$ and $R_3$ are independently H;

$R_4$ is $L_3$-X-$L_4$-G, wherein, $L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;

X is optional, and when present is a bond, —O—, —C(=O)—, —S—, —S(=O)—, —S(=O)$_2$—, —NH—, —NR$_9$—, —NHC(O)—, —C(O)NH—, —NR$_9$C(O)—, —C(O)NR$_9$—, —S(=O)$_2$NH—, —NHS(=O)$_2$—, —S(=O)$_2$NR$_9$—, —NR$_9$S(=O)$_2$—, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl-, aryl-, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;

$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;

or $L_3$, X and $L_4$ taken together form a nitrogen containing heterocyclic ring;

G is

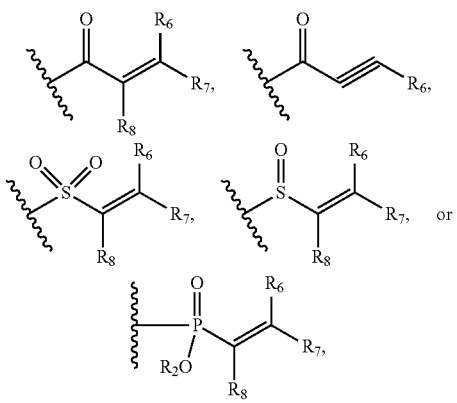

wherein, $R_6$, $R_7$ and $R_8$ are independently selected from among H, halogen, CN, OH, substituted or unsubstituted alkyl or substituted or unsubstituted heteroalkyl or substituted or unsubstituted cycloalkyl, substituted or unsubstituted heterocycloalkyl, substituted or unsubstituted aryl, substituted or unsubstituted heteroaryl;

each $R_9$ is independently selected from among H, substituted or unsubstituted lower alkyl, and substituted or unsubstituted lower cycloalkyl;

each $R_{10}$ is independently H, substituted or unsubstituted lower alkyl, or substituted or unsubstituted lower cycloalkyl; or two $R_{10}$ groups can together form a 5-, 6-, 7-, or 8-membered heterocyclic ring; or $R_{10}$ and $R_{11}$ can together form a 5-, 6-, 7-, or 8-membered heterocyclic ring; or each $R_{11}$ is independently selected from H or substituted or unsubstituted alkyl; or a pharmaceutically acceptable salt thereof, is administered prior to, concurrently with, or following the allogeneic hematopoietic stem cells and/or allogeneic T-cells. In some embodiments, $L_3$, X and $L_4$ taken together form a nitrogen containing heterocyclic ring. In some embodiments, the nitrogen containing heterocyclic ring is a piperidine group. In some embodiments, G is

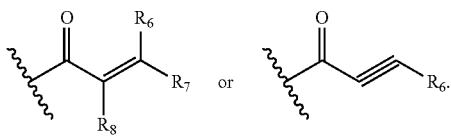

In some embodiments, the compound of Formula (A) is 1-[(3R)-3-[4-amino-3-(4-phenoxyphenyl)pyrazolo[3,4-d]pyrimidin-1-yl]piperidin-1-yl]prop-2-en-1-one. In some embodiments, the patient has cancer. In some embodiments, the patient has a hematological malignancy. In some embodiments, the patient has a relapsed or refractory hematological malignancy. In some embodiments, the patient has a leukemia, a lymphoma, or a myeloma. In some embodiments, the patient has a B-cell malignancy. In some embodiments, the B-cell malignancy is a non-Hodgkin's lymphoma. In some embodiments, the B-cell malignancy is chronic lymphocytic leukemia (CLL). In some embodiments, the B-cell malignancy is a relapsed or refractory B-cell malignancy. In some embodiments, the B-cell malignancy is a relapsed or refractory non-Hodgkin's lymphoma. In some embodiments, the B-cell malignancy is a relapsed or refractory CLL. In some embodiments, the patient has high risk CLL. In some embodiments, the patient has a 17p chromosomal deletion. In some embodiments, the patient has 10%, 20%, 30%, 40%, 50%, 60%, 70%, 80%, 90%, or greater CLL as determined by bone marrow biopsy. In some embodiments, the patient has received one or more prior anticancer agents. In some embodiments, the anticancer agent is selected from among alemtuzumab, bendamustine, bortezomib, CAL-101, chlorambucil, cyclophosphamide, dexamethasone, docetaxel, doxorubicin, endostatineveroli-mus, etoposide, fludarabine, fostamatinib, hydroxydaunoru-bicin, ibritumomab, ifosphamide, lenalidomide, mesalazine, ofatumumab, paclitaxel, pentostatin, prednisone, rituximab, temsirolimus, thalidomide, tositumomab, vincristine, or a combination thereof. In some embodiments, the anticancer agent is rituximab. In some embodiments, the anticancer agent is alemtuzumab. In some embodiments, the anticancer agent is fludarabine, cyclophosphamide, and rituximab (FCR). In some embodiments, the anticancer agent is oxa-liplatin, fludarabine, cytarabine, rituximab (OFAR). In some embodiments, the amount of the ACK inhibitor compound (e.g., a compound of Formula (A)) prevents or reduces GVHD while maintaining a graft-versus-leukemia (GVL) reaction effective to reduce or eliminate the number of cancerous cells in the blood of the patient. In some embodi-ments, the cell transplantation is a hematopoietic cell trans-plantation. In some embodiments, the GVHD is acute GVHD. In some embodiments, the GVHD is chronic GVHD. In some embodiments, the GVHD is scleroderma-tous GVHD. In some embodiments, the GVHD is steroid resistant GVHD. In some embodiments, the GVHD is cyclosporin-resistant GVHD. In some embodiments, the GVHD is refractory GVHD. In some embodiments, the GHVD is oral GVHD. In some embodiments, the oral GVHD is reticular oral GVHD. In some embodiments, the oral GVHD is erosive oral GVHD. In some embodiments, the oral GVHD is ulcerative oral GVHD. In some embodi-ments, the oral GVHD is GVHD of the oral cavity. In some embodiments, the oral GVHD is GVHD of the oropharyn-geal region. In some embodiments, the oral GVHD is GVHD of the pharyngeal region. In some embodiments, the oral GVHD is GVHD of the esophageal region. In some embodiments, the oral GVHD is acute oral GVHD. In some embodiments, the oral GVHD is chronic oral GVHD. In some embodiments, the patient exhibits one or more symp-toms of GVHD. In some embodiments, the patient has or will receive an allogeneic bone marrow or hematopoietic stem cell transplant. In some embodiments, the ACK inhibi-tor compound (e.g., a compound of Formula (A)) is admin-istered concurrently with an allogeneic bone marrow or hematopoietic stem cell transplant. In some embodiments, the ACK inhibitor compound (e.g., a compound of Formula (A)) is administered prior to an allogeneic bone marrow or hematopoietic stem cell transplant. In some embodiments, the ACK inhibitor compound (e.g., a compound of Formula (A)) is administered subsequent to an allogeneic bone mar-row or hematopoietic stem cell transplant. In some embodi-ments, the patient is a candidate for receiving HLA-mis-matched hematopoietic stem cells. In some embodiments, the patient is a candidate for receiving unrelated donor hematopoietic stem cells, umbilical vein hematopoietic stem cells, or peripheral blood stem cells. In some embodiments, the ACK inhibitor compound (e.g., a compound of Formula (A)) is administered at a dosage of between about 0.1 mg/kg per day to about 100 mg/kg per day. In some embodiments, the ACK inhibitor compound (e.g., a compound of Formula (A)) is administered at a dosage of about 40 mg/day, about 140 mg/day, about 280 mg/day, about 420 mg/day, about 560 mg/day, or about 840 mg/day. In some embodiments, the ACK inhibitor compound (e.g., a compound of Formula (A)) is administered orally. In some embodiments, the ACK inhibitor compound (e.g., a compound of Formula (A)) is administered in combination with additional therapeutic agents. In some embodiments, the additional therapeutic agent is a corticosteroid. In some embodiments, the addi-tional therapeutic agent is cyclosporine (CSA), mycophe-nolate mofetil (MMF) or a combination thereof. In some embodiments, the ACK inhibitor compound (e.g., a com-pound of Formula (A)) is administered from day 1 to about day 120 following allogeneic bone marrow or hematopoietic stem cell transplant. In some embodiments, the ACK inhibi-tor compound (e.g., a compound of Formula (A)) is admin-istered from day 1 to about day 1000 following allogeneic bone marrow or hematopoietic stem cell transplant. In some embodiments, the patient has or will receive a donor lym-phocyte infusion (DLI). In some embodiments, the patient has or will receive two or more donor lymphocyte infusions (DLI). In some embodiments, the patient is administered one or more donor lymphocyte infusions (DLI). In some embodiments, the DLI comprises CD3+ lymphocytes. In some embodiments, the patient is administered one or more donor lymphocyte infusions (DLI) following an allogeneic bone marrow or hematopoietic stem cell transplant. In some embodiments, the ACK inhibitor compound (e.g., a com-pound of Formula (A)) is administered concurrently with a DLI following allogeneic bone marrow or hematopoietic stem cell transplant. In some embodiments, the ACK inhibi-tor compound (e.g., a compound of Formula (A)) is admin-istered prior to a DLI following an allogeneic bone marrow or hematopoietic stem cell transplant. In some embodiments, the ACK inhibitor compound (e.g., a compound of Formula (A)) is administered following a DLI following an alloge-neic bone marrow or hematopoietic stem cell transplant. In some embodiments, the ACK inhibitor compound (e.g., a compound of Formula (A)) is ibrutinib.

In some embodiments, disclosed herein are methods of reducing the severity of GVHD occurrence in a patient requiring cell transplantation comprising administration of a therapeutically effective amount of ibrutinib (1-[(3R)-3-[4-amino-3-(4-phenoxyphenyl)pyrazolo[3,4-d]pyrimidin-1-yl] piperidin-1-yl]prop-2-en-1-one). In some embodiments, the patient has cancer. In some embodiments, the patient has a hematological malignancy. In some embodiments, the patient has a relapsed or refractory hematological malig-nancy. In some embodiments, the patient has a B-cell malignancy. In some embodiments, the patient has a T-cell malignancy. In some embodiments, the patient has a leuke-mia, a lymphoma, or a myeloma. In some embodiments, the B-cell malignancy is a non-Hodgkin's lymphoma. In some embodiments, the B-cell malignancy is chronic lymphocytic leukemia (CLL). In some embodiments, the B-cell malig-nancy is a relapsed or refractory B-cell malignancy. In some embodiments, the B-cell malignancy is a relapsed or refrac-tory non-Hodgkin's lymphoma. In some embodiments, the B-cell malignancy is a relapsed or refractory CLL. In some embodiments, the patient has high risk CLL. In some embodiments, the patient has a 17p chromosomal deletion. In some embodiments, the patient has 10%, 20%, 30%, 40%, 50%, 60%, 70%, 80%, 90%, or greater CLL as determined by bone marrow biopsy. In some embodiments, the patient has received one or more prior anticancer agents. In some embodiments, the anticancer agent is selected from among alemtuzumab, bendamustine, bortezomib, CAL-101, chlorambucil, cyclophosphamide, dexamethasone, docetaxel, doxorubicin, endostatineverolimus, etoposide, fludarabine, fostamatinib, hydroxydaunorubicin, ibritumomab, ifosphamide, lenalidomide, mesalazine, ofatumumab, paclitaxel, pentostatin, prednisone, rituximab, temsirolimus, thalidomide, tositumomab, vincristine, or a combination thereof. In some embodiments, the anticancer agent is rituximab. In some embodiments, the anticancer agent is alemtuzumab. In some embodiments, the anticancer agent is fludarabine, cyclophosphamide, and rituximab (FCR). In some embodiments, the anticancer agent is oxaliplatin, fludarabine, cytarabine, rituximab (OFAR). In some embodiments, the amount of ibrutinib prevents or reduces GVHD while maintaining a graft-versus-leukemia (GVL) reaction effective to reduce or eliminate the number of cancerous cells in the blood of the patient. In some embodiments, the cell transplantation is a hematopoietic cell transplantation. In some embodiments, the GVHD is acute GVHD. In some embodiments, the GVHD is chronic GVHD. In some embodiments, the GVHD is sclerodermatous GVHD. In some embodiments, the GVHD is steroid resistant GVHD. In some embodiments, the GVHD is cyclosporin-resistant GVHD. In some embodiments, the GVHD is refractory GVHD. In some embodiments, the GHVD is oral GVHD. In some embodiments, the oral GVHD is reticular oral GVHD. In some embodiments, the oral GVHD is erosive oral GVHD. In some embodiments, the oral GVHD is ulcerative oral GVHD. In some embodiments, the oral GVHD is GVHD of the oral cavity. In some embodiments, the oral GVHD is GVHD of the oropharyngeal region. In some embodiments, the oral GVHD is GVHD of the pharyngeal region. In some embodiments, the oral GVHD is GVHD of the esophageal region. In some embodiments, the oral GVHD is acute oral GVHD. In some embodiments, the oral GVHD is chronic oral GVHD. In some embodiments, the patient exhibits one or more symptoms of GVHD. In some embodiments, the patient has or will receive an allogeneic bone marrow or hematopoietic stem cell transplant. In some embodiments, the ibrutinib is administered concurrently with an allogeneic bone marrow or hematopoietic stem cell transplant. In some embodiments, the ibrutinib is administered prior to an allogeneic bone marrow or hematopoietic stem cell transplant. In some embodiments, the ibrutinib is administered subsequent to an allogeneic bone marrow or hematopoietic stem cell transplant. In some embodiments, the patient is a candidate for receiving HLA-mismatched hematopoietic stem cells. In some embodiments, the patient is a candidate for receiving unrelated donor hematopoietic stem cells, umbilical vein hematopoietic stem cells, or peripheral blood stem cells. In some embodiments, the ibrutinib is administered orally. In some embodiments, the ibrutinib is administered at a dosage of between about 0.1 mg/kg per day to about 100 mg/kg per day. In some embodiments, the ibrutinib is administered at a dosage of about 40 mg/day, about 140 mg/day, about 280 mg/day, about 420 mg/day, about 560 mg/day, or about 840 mg/day. In some embodiments, the ibrutinib is administered in combination with other prophylactic agents. In some embodiments, the ibrutinib is administered from day 1 to about day 120 following allogeneic bone marrow or hematopoietic stem cell transplant. In some embodiments, the ibrutinib is administered from day 1 to about day 1000 following allogeneic bone marrow or hematopoietic stem cell transplant. In some embodiments, the ibrutinib is administered in combination with one or more additional therapeutic agents. In some embodiments, the additional therapeutic agent is a corticosteroid. In some embodiments, the therapeutic agent is cyclosporine (CSA), mycophenolate mofetil (MMF) or a combination thereof. In some embodiments, the patient has or will receive a donor lymphocyte infusions (DLI). In some embodiments, the patient is administered one or more DLIs. In some embodiments, the patient is administered two or more DLIs. In some embodiments, the DLI comprises CD3+ lymphocytes. In some embodiments, the patient is administered one or more donor lymphocyte infusions (DLI) following an allogeneic bone marrow or hematopoietic stem cell transplant. In some embodiments, the ibrutinib is administered concurrently with a DLI following allogeneic bone marrow or hematopoietic stem cell transplant. In some embodiments, the ibrutinib is administered prior to a DLI following an allogeneic bone marrow or hematopoietic stem cell transplant. In some embodiments, the ibrutinib is administered following a DLI following an allogeneic bone marrow or hematopoietic stem cell transplant.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
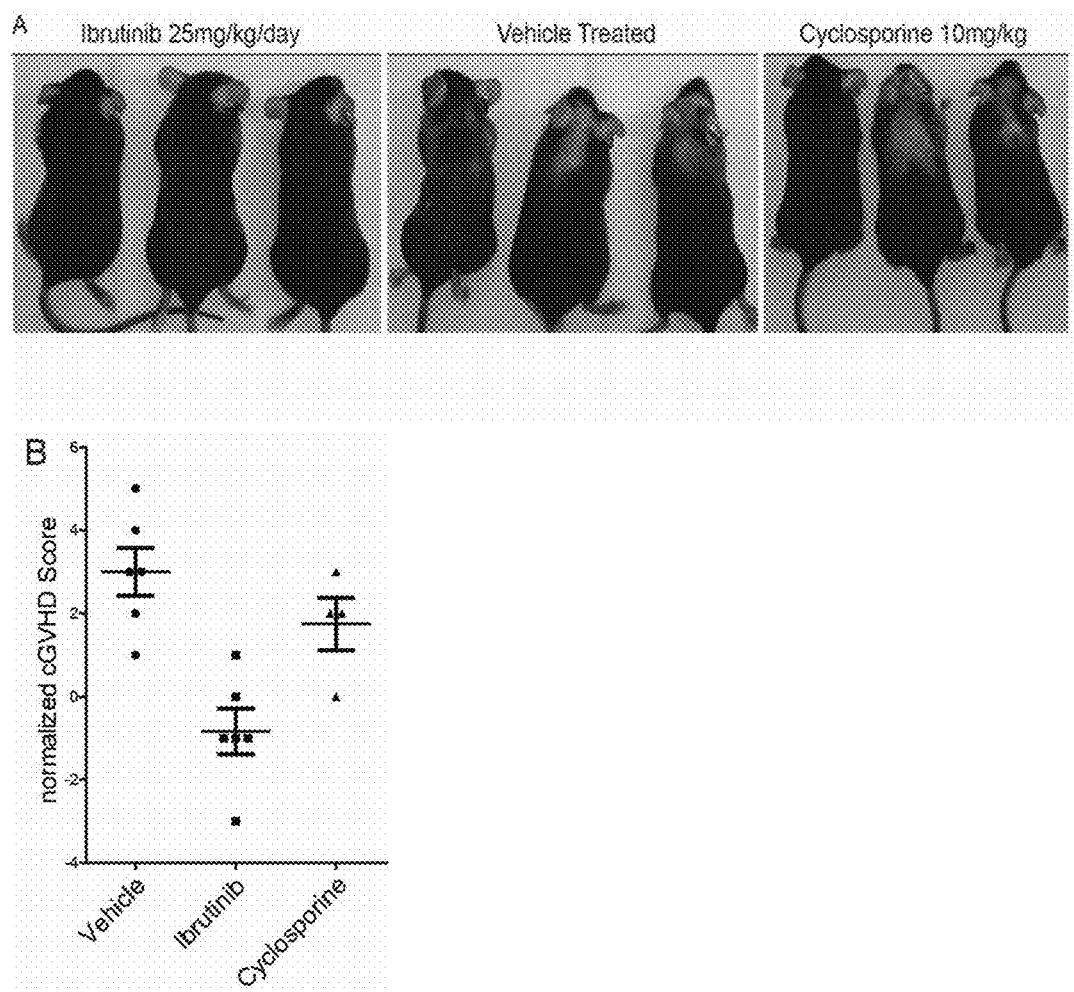
FIG. 1 exemplifies that ibrutinib ameliorates cGVHD symptomatology after allotransplant. C57BL/6 mice were engrafted with LP/J bone marrow after 850 cGy lethal irradiation. 25 days post-transplant mice were randomly assigned to ibrutinib, vehicle, or cyclosporine groups. Panel A shows images showing external signs of cGVHD including alopecia, scleroderma, and fibrotic lesions at day 36 post-transplant. Ibrutinib treatment group displayed few external signs of cGVHD progression as compared to vehicle or cyclosporine groups. Panel B shows an analysis of cGVHD mouse groups using a physical scoring system adapted from Cooke et al., which incorporates weight, posture, coat condition, skin condition, and mobility. Scoring was conducted on day 36 post-transplantation. Panel C shows the LP/J→C57BL/6 cGVHD scoring. Each category: coat condition, skin condition, weight, posture, mobility, and vitality are individually scored and summed to achieve an overall cGVHD condition score. Scores are taken by a consistent unbiased observer with no knowledge of treatment cohorts. Panel D provides images of cGVHD mouse groups at day 39 post-HSCT. Panel E provides images of H&E stained skin preparations of sclerodermatous skin lesions showing levels of dermal fibrosis, epidermal hyperplasia, serocellular crusting, erosion, and lymphohistiocytic infiltration, consistent with cGVHD.
Figure 1:
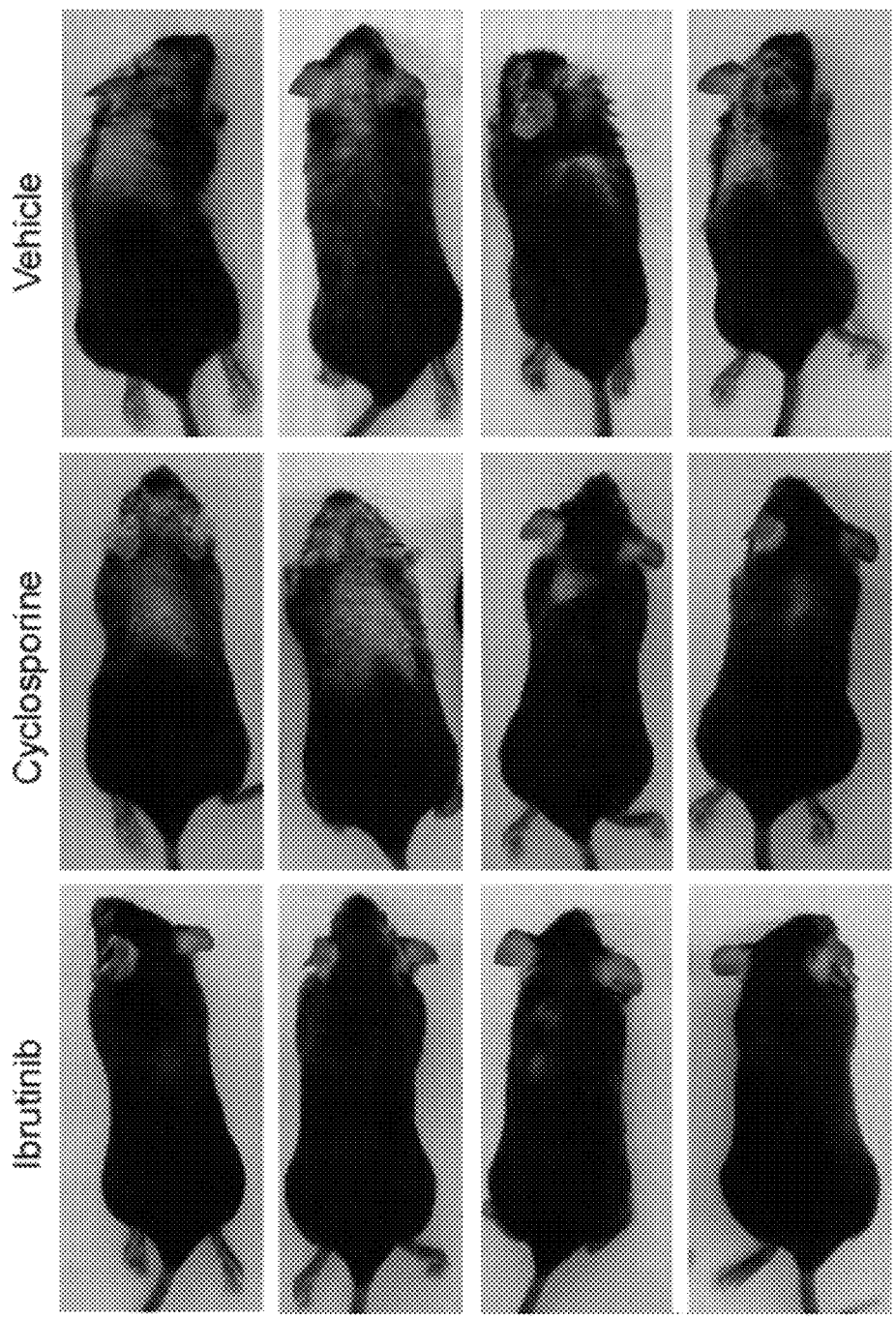
Figure 1:
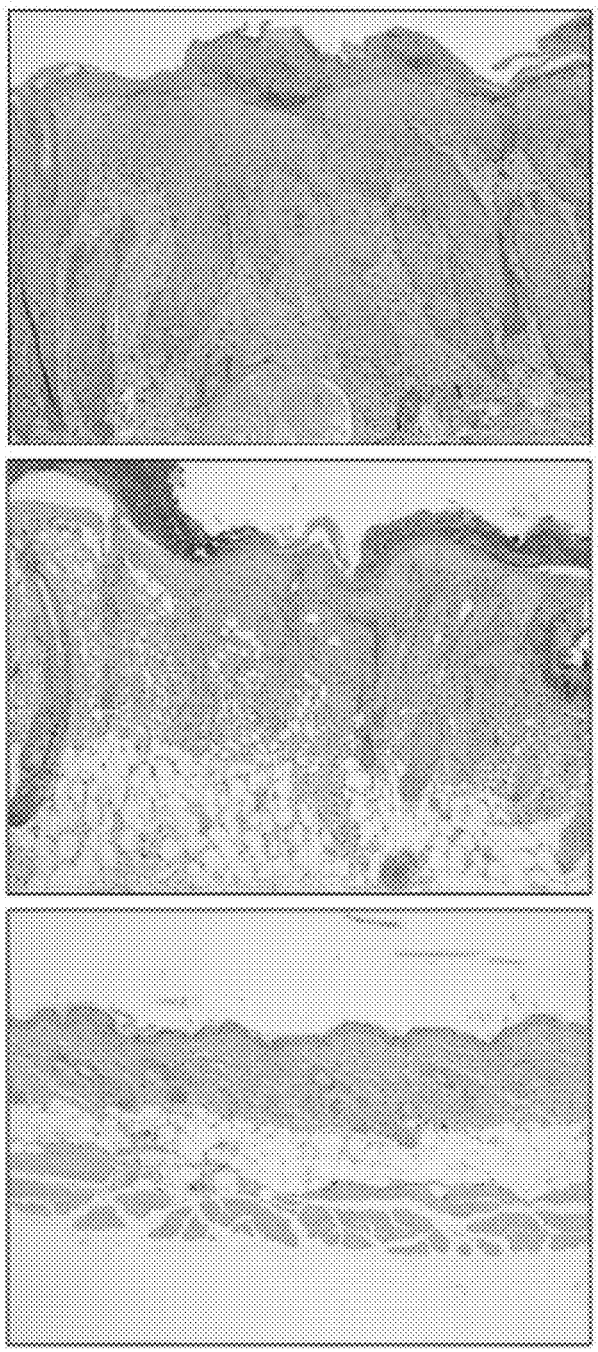

In some embodiments, disclosed herein is a method of preventing the occurrence of graft versus host disease (GVHD) or reducing the severity of GVHD occurrence in a patient requiring cell transplantation, comprising administration of an ACK inhibitor compound (e.g., an ITK or BTK inhibitor compound). In some embodiments, disclosed herein is a method of preventing the occurrence of graft versus host disease (GVHD) or reducing the severity of GVHD occurrence in a patient requiring cell transplantation, comprising administration of a therapeutically effective amount of a compound of Formula (A) having the structure:

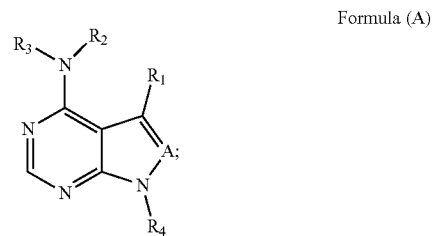

Formula (A)

wherein:

A is N;

$R_1$ is phenyl-O-phenyl or phenyl-S-phenyl;

$R_2$ and $R_3$ are independently H;

$R_4$ is $L_3$-X-$L_4$-G, wherein, $L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;

X is optional, and when present is a bond, —O—, —C(=O)—, —S—, —S(=O)—, —S(=O)$_2$—, —NH—, —NR$_9$—, —NHC(O)—, —C(O)NH—, —NR$_9$C(O)—, —C(O)NR$_9$—, —S(=O)$_2$NH—, —NHS(=O)$_2$—, —S(=O)$_2$NR$_9$—, —NR$_9$S(=O)$_2$—, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl-, aryl-, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;

L$_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;

or L$_3$, X and L$_4$ taken together form a nitrogen containing heterocyclic ring;

G is

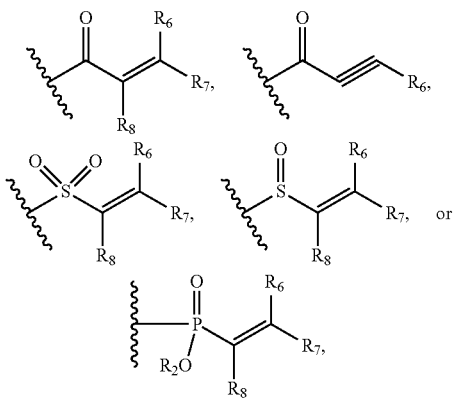

wherein,

R$_6$, R$_7$ and R$_8$ are independently selected from among H, halogen, CN, OH, substituted or unsubstituted alkyl or substituted or unsubstituted heteroalkyl or substituted or unsubstituted cycloalkyl, substituted or unsubstituted heterocycloalkyl, substituted or unsubstituted aryl, substituted or unsubstituted heteroaryl;

each R$_9$ is independently selected from among H, substituted or unsubstituted lower alkyl, and substituted or unsubstituted lower cycloalkyl;

each R$_{10}$ is independently H, substituted or unsubstituted lower alkyl, or substituted or unsubstituted lower cycloalkyl; or two R$_{10}$ groups can together form a 5-, 6-, 7-, or 8-membered heterocyclic ring; or R$_{10}$ and R$_{11}$ can together form a 5-, 6-, 7-, or 8-membered heterocyclic ring; or each R$_{11}$ is independently selected from H or substituted or unsubstituted alkyl; or a pharmaceutically acceptable salt thereof. In some embodiments, L$_3$, X and L$_4$ taken together form a nitrogen containing heterocyclic ring. In some embodiments, the nitrogen containing heterocyclic ring is a piperidine group. In some embodiments, G is

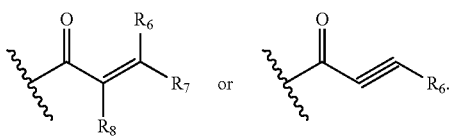

In some embodiments, the compound of Formula (A) is 1-[(3R)-3-[4-amino-3-(4-phenoxyphenyl)pyrazolo[3,4-d]pyrimidin-1-yl]piperidin-1-yl]prop-2-en-1-one. In some embodiments, the patient has cancer. In some embodiments, the patient has a hematologic malignancy. In some embodiments, the patient has a B-cell malignancy. In some embodiments, the patient has a T-cell malignancy. In some embodiments, the patient has a leukemia, a lymphoma, or a myeloma. In some embodiments, the patient has a B-cell malignancy. In some embodiments, the B-cell malignancy is a non-Hodgkin's lymphoma. In some embodiments, the B-cell malignancy is chronic lymphocytic leukemia (CLL). In some embodiments, the B-cell malignancy is a relapsed or refractory B-cell malignancy. In some embodiments, the B-cell malignancy is a relapsed or refractory non-Hodgkin's lymphoma. In some embodiments, the B-cell malignancy is a relapsed or refractory CLL. In some embodiments, the patient has high risk CLL. In some embodiments, the patient has a 17p chromosomal deletion. In some embodiments, the patient has 10%, 20%, 30%, 40%, 50%, 60%, 70%, 80%, 90%, or greater CLL as determined by bone marrow biopsy. In some embodiments, the patient has received one or more prior anticancer agents. In some embodiments, the anticancer agent is selected from among alemtuzumab, bendamustine, bortezomib, CAL-101, chlorambucil, cyclophosphamide, dexamethasone, docetaxel, doxorubicin, endostatineverolimus, etoposide, fludarabine, fostamatinib, hydroxydaunorubicin, ibritumomab, ifosphamide, lenalidomide, mesalazine, ofatumumab, paclitaxel, pentostatin, prednisone, rituximab, temsirolimus, thalidomide, tositumomab, vincristine, or a combination thereof. In some embodiments, the anticancer agent is rituximab. In some embodiments, the anticancer agent is alemtuzumab. In some embodiments, the anticancer agent is fludarabine, cyclophosphamide, and rituximab (FCR). In some embodiments, the anticancer agent is oxaliplatin, fludarabine, cytarabine, rituximab (OFAR). In some embodiments, the amount of the compound of Formula (A) prevents or reduces GVHD while maintaining a graft-versus-leukemia (GVL) reaction effective to reduce or eliminate the number of cancerous cells in the blood of the patient. In some embodiments, the cell transplantation is a hematopoietic cell transplantation. In some embodiments, the GVHD is acute GVHD. In some embodiments, the GVHD is chronic GVHD. In some embodiments, the GVHD is sclerodermatous GVHD. In some embodiments, the GVHD is steroid resistant GVHD. In some embodiments, the GVHD is cyclosporin-resistant GVHD. In some embodiments, the GVHD is refractory GVHD. In some embodiments, the GHVD is oral GVHD. In some embodiments, the oral GVHD is reticular oral GVHD. In some embodiments, the oral GVHD is erosive oral GVHD. In some embodiments, the oral GVHD is ulcerative oral GVHD. In some embodiments, the oral GVHD is GVHD of the oral cavity. In some embodiments, the oral GVHD is GVHD of the oropharyngeal region. In some embodiments, the oral GVHD is GVHD of the pharyngeal region. In some embodiments, the oral GVHD is GVHD of the esophageal region. In some embodiments, the oral GVHD is acute oral GVHD. In some embodiments, the oral GVHD is chronic oral GVHD. In some embodiments, the patient exhibits one or more symptoms of GVHD. In some embodiments, the patient has or will receive an allogeneic bone marrow or hematopoietic stem cell transplant. In some embodiments, the compound of Formula (A) is administered concurrently with an allogeneic bone marrow or hematopoietic stem cell transplant. In some embodiments, the compound of Formula (A) is administered prior to an allogeneic bone marrow or hematopoietic stem cell transplant. In some embodiments, the compound of Formula (A) is administered following an allogeneic bone marrow or hematopoietic stem cell transplant. In some embodiments, the patient is a candidate for receiving HLA-mismatched hematopoietic stem cells. In some embodiments, the patient is a candidate for receiving unrelated donor hematopoietic stem cells, umbilical vein hematopoietic stem cells, or peripheral blood stem cells. In some embodiments, the compound of Formula (A) is administered at a dosage of between about 0.1 mg/kg per day to about 100 mg/kg per day. In some embodiments, the compound of Formula (A) is administered at a dosage of about 40 mg/day, about 140 mg/day, about 280 mg/day, about 420 mg/day, about 560 mg/day, or about 840 mg/day. In some embodiments, the compound of Formula (A) is administered in combination with additional therapeutic agents. In some embodiments, the additional therapeutic agent is a corticosteroid. In some embodiments, the additional therapeutic agent is cyclosporine (CSA), mycophenolate mofetil (MMF) or a combination thereof. In some embodiments, the compound of Formula (A) is administered orally. In some embodiments, the compound of Formula (A) is administered from day 1 to about day 120 following allogeneic bone marrow or hematopoietic stem cell transplant. In some embodiments, the compound of Formula (A) is administered from day 1 to about day 1000 following allogeneic bone marrow or hematopoietic stem cell transplant. In some embodiments, the patient is administered one or more donor lymphocyte infusions (DLI). In some embodiments, the DLI comprises CD3+ lymphocytes. In some embodiments, the patient is administered one or more donor lymphocyte infusions (DLI) following an allogeneic bone marrow or hematopoietic stem cell transplant. In some embodiments, the compound of Formula (A) is administered concurrently with a DLI following allogeneic bone marrow or hematopoietic stem cell transplant. In some embodiments, the compound of Formula (A) is administered prior to a DLI following an allogeneic bone marrow or hematopoietic stem cell transplant. In some embodiments, the compound of Formula (A) is administered following a DLI following an allogeneic bone marrow or hematopoietic stem cell transplant. In some embodiments, the compound of Formula (A) is ibrutinib.

Disclosed herein, in some embodiments, is a method of treating a patient for alleviation of a bone marrow mediated disease, with alleviation of consequently developed graft versus host disease (GVHD), comprising administering to the patient allogeneic hematopoietic stem cells and/or allogeneic T-cells, wherein a therapeutically effective amount of a compound of Formula (A):

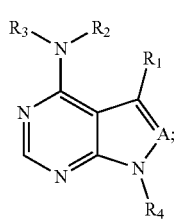

Formula (A)

wherein:
A is N;
$R_1$ is phenyl-O-phenyl or phenyl-S-phenyl;
$R_2$ and $R_3$ are independently H;
$R_4$ is $L_3$-X-$L_4$-G, wherein,
$L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;

X is optional, and when present is a bond, —O—, —C(=O)—, —S—, —S(=O)—, —S(=O)$_2$—, —NH—, —NR$_9$—, —NHC(O)—, —C(O)NH—, —NR$_9$C(O)—, —C(O)NR$_9$—, —S(=O)$_2$NH—, —NHS(=O)$_2$—, —S(=O)$_2$NR$_9$—, —NR$_9$S(=O)$_2$—, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl-, aryl-, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;

$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;

or $L_3$, X and $L_4$ taken together form a nitrogen containing heterocyclic ring;

G is

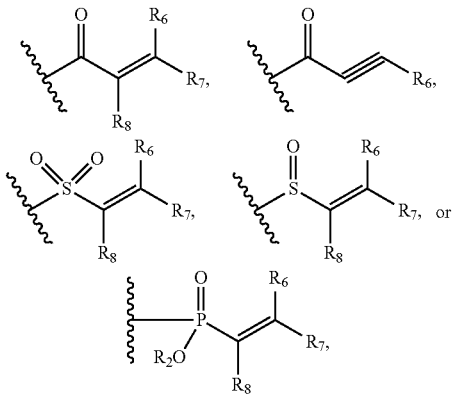

wherein, $R_6$, $R_7$ and $R_8$ are independently selected from among H, halogen, CN, OH, substituted or unsubstituted alkyl or substituted or unsubstituted heteroalkyl or substituted or unsubstituted cycloalkyl, substituted or unsubstituted heterocycloalkyl, substituted or unsubstituted aryl, substituted or unsubstituted heteroaryl;

each $R_9$ is independently selected from among H, substituted or unsubstituted lower alkyl, and substituted or unsubstituted lower cycloalkyl;

each $R_{10}$ is independently H, substituted or unsubstituted lower alkyl, or substituted or unsubstituted lower cycloalkyl; or two $R_{10}$ groups can together form a 5-, 6-, 7-, or 8-membered heterocyclic ring; or $R_{10}$ and $R_{11}$ can together form a 5-, 6-, 7-, or 8-membered heterocyclic ring; or each $R_{11}$ is independently selected from H or substituted or unsubstituted alkyl; or a pharmaceutically acceptable salt thereof, is administered prior to, concurrently with, or following the administration allogeneic hematopoietic stem cells and/or allogeneic T-cells. In some embodiments, $L_3$, X and $L_4$ taken together form a nitrogen containing heterocyclic ring. In some embodiments, the nitrogen containing heterocyclic ring is a piperidine group. In some embodiments, G is

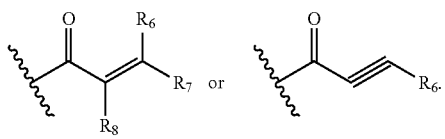

In some embodiments, the compound of Formula (A) is 1-[(3R)-3-[4-amino-3-(4-phenoxyphenyl)pyrazolo[3,4-d]pyrimidin-1-yl]piperidin-1-yl]prop-2-en-1-one. In some embodiments, the patient has cancer. In some embodiments, the patient as a hematologic malignancy. In some embodiments, the patient has a B-cell malignancy. In some embodiments, the patient has a T-cell malignancy. In some embodiments, the patient has a leukemia, a lymphoma, or a myeloma. In some embodiments, the patient has a B-cell malignancy. In some embodiments, the B-cell malignancy is a non-Hodgkin's lymphoma. In some embodiments, the B-cell malignancy is chronic lymphocytic leukemia (CLL). In some embodiments, the B-cell malignancy is a relapsed or refractory B-cell malignancy. In some embodiments, the B-cell malignancy is a relapsed or refractory non-Hodgkin's lymphoma. In some embodiments, the B-cell malignancy is a relapsed or refractory CLL. In some embodiments, the patient has high risk CLL. In some embodiments, the patient has a 17p chromosomal deletion. In some embodiments, the patient has 10%, 20%, 30%, 40%, 50%, 60%, 70%, 80%, 90%, or greater CLL as determined by bone marrow biopsy. In some embodiments, the patient has received one or more prior anticancer agents. In some embodiments, the anticancer agent is selected from among alemtuzumab, bendamustine, bortezomib, CAL-101, chlorambucil, cyclophosphamide, dexamethasone, docetaxel, doxorubicin, endostatineverolimus, etoposide, fludarabine, fostamatinib, hydroxydaunorubicin, ibritumomab, ifosfamide, lenalidomide, mesalazine, ofatumumab, paclitaxel, pentostatin, prednisone, rituximab, temsirolimus, thalidomide, tositumomab, vincristine, or a combination thereof. In some embodiments, the anticancer agent is rituximab. In some embodiments, the anticancer agent is alemtuzumab. In some embodiments, the anticancer agent is fludarabine, cyclophosphamide, and rituximab (FCR). In some embodiments, the anticancer agent is oxaliplatin, fludarabine, cytarabine, rituximab (OFAR). In some embodiments, the amount of the compound of Formula (A) prevents or reduces GVHD while maintaining a graft-versus-leukemia (GVL) reaction effective to reduce or eliminate the number of cancerous cells in the blood of the patient. In some embodiments, the cell transplantation is a hematopoietic cell transplantation. In some embodiments, the GVHD is acute GVHD. In some embodiments, the GVHD is chronic GVHD. In some embodiments, the GVHD is sclerodermatous GVHD. In some embodiments, the GVHD is steroid resistant GVHD. In some embodiments, the GVHD is cyclosporin-resistant GVHD. In some embodiments, the GVHD is refractory GVHD. In some embodiments, the GHVD is oral GVHD. In some embodiments, the oral GVHD is reticular oral GVHD. In some embodiments, the oral GVHD is erosive oral GVHD. In some embodiments, the oral GVHD is ulcerative oral GVHD. In some embodiments, the oral GVHD is GVHD of the oral cavity. In some embodiments, the oral GVHD is GVHD of the oropharyngeal region. In some embodiments, the oral GVHD is GVHD of the pharyngeal region. In some embodiments, the oral GVHD is GVHD of the esophageal region. In some embodiments, the oral GVHD is acute oral GVHD. In some embodiments, the oral GVHD is chronic oral GVHD. In some embodiments, the patient exhibits one or more symptoms of GVHD. In some embodiments, the patient has or will receive an allogeneic bone marrow or hematopoietic stem cell transplant. In some embodiments, the compound of Formula (A) is administered concurrently with an allogeneic bone marrow or hematopoietic stem cell transplant. In some embodiments, the compound of Formula (A) is administered prior to an allogeneic bone marrow or hematopoietic stem cell transplant. In some embodiments, the compound of Formula (A) is administered following an allogeneic bone marrow or hematopoietic stem cell transplant. In some embodiments, the patient is a candidate for receiving HLA-mismatched hematopoietic stem cells. In some embodiments, the patient is a candidate for receiving unrelated donor hematopoietic stem cells, umbilical vein hematopoietic stem cells, or peripheral blood stem cells. In some embodiments, the compound of Formula (A) is administered at a dosage of between about 0.1 mg/kg per day to about 100 mg/kg per day. In some embodiments, the compound of Formula (A) is administered at a dosage of about 40 mg/day, about 140 mg/day, about 280 mg/day about 420 mg/day, about 560 mg/day, or about 840 mg/day. In some embodiments, the compound of Formula (A) is administered in combination with additional therapeutic agents. In some embodiments, the additional therapeutic agent is a corticosteroid. In some embodiments, the additional therapeutic agent is cyclosporine (CSA), mycophenolate mofetil (MMF) or a combination thereof. In some embodiments, the compound of Formula (A) is administered orally. In some embodiments, the compound of Formula (A) is administered from day 1 to about day 120 following allogeneic bone marrow or hematopoietic stem cell transplant. In some embodiments, the compound of Formula (A) is administered from day 1 to about day 1000 following allogeneic bone marrow or hematopoietic stem cell transplant. In some embodiments, the patient is administered one or more donor lymphocyte infusions (DLI). In some embodiments, the DLI comprises CD3+ lymphocytes. In some embodiments, the patient is administered one or more donor lymphocyte infusions (DLI) following an allogeneic bone marrow or hematopoietic stem cell transplant. In some embodiments, the compound of Formula (A) is administered concurrently with a DLI following allogeneic bone marrow or hematopoietic stem cell transplant. In some embodiments, the compound of Formula (A) is administered prior to a DLI following an allogeneic bone marrow or hematopoietic stem cell transplant. In some embodiments, the compound of Formula (A) is administered following a DLI following an allogeneic bone marrow or hematopoietic stem cell transplant. In some embodiments, the compound of Formula (A) is ibrutinib.

In some embodiments, there are provided uses of a compound of Formula (A) for preventing the occurrence of graft versus host disease (GVHD) or reducing the severity of GVHD occurrence in a patient requiring cell transplantation, wherein Formula (A) has the structure:

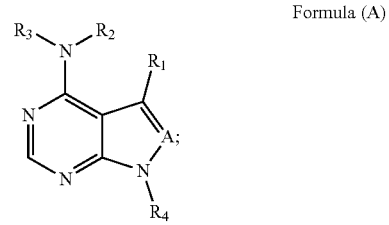

Formula (A)

Formula (A);
wherein:
A is N;
$R_1$ is phenyl-O-phenyl or phenyl-S-phenyl;
$R_2$ and $R_3$ are independently H;
$R_4$ is $L_3$-X-$L_4$-G, wherein,
$L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;
X is optional, and when present is a bond, —O—, —C(=O)—, —S—, —S(=O)—, —S(=O)$_2$—, —NH—, —NR$_9$—, —NHC(O)—, —C(O)NH—, —NR$_9$C(O)—, —C(O)NR$_9$—, —S(=O)$_2$NH—, —NHS(=O)$_2$—, —S(=O)$_2$NR$_9$—, —NR$_9$S(=O)$_2$—, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl-, aryl-, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;
$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;
or $L_3$, X and $L_4$ taken together form a nitrogen containing heterocyclic ring;
G is

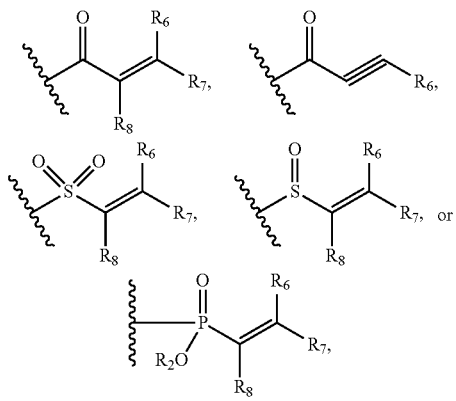

wherein,
$R_6$, $R_7$ and $R_8$ are independently selected from among H, halogen, CN, OH, substituted or unsubstituted alkyl or substituted or unsubstituted heteroalkyl or substituted or unsubstituted cycloalkyl, substituted or unsubstituted heterocycloalkyl, substituted or unsubstituted aryl, substituted or unsubstituted heteroaryl;
each $R_9$ is independently selected from among H, substituted or unsubstituted lower alkyl, and substituted or unsubstituted lower cycloalkyl;
each $R_{10}$ is independently H, substituted or unsubstituted lower alkyl, or substituted or unsubstituted lower cycloalkyl; or
two $R_{10}$ groups can together form a 5-, 6-, 7-, or 8-membered heterocyclic ring; or
$R_{10}$ and $R_{11}$ can together form a 5-, 6-, 7-, or 8-membered heterocyclic ring; or each $R_{11}$ is independently selected from H or substituted or unsubstituted alkyl; or a pharmaceutically acceptable salt thereof. In some embodiments, $L_3$, X and $L_4$ taken together form a nitrogen containing heterocyclic ring. In some embodiments, the nitrogen containing heterocyclic ring is a piperidine group. In some embodiments, G is

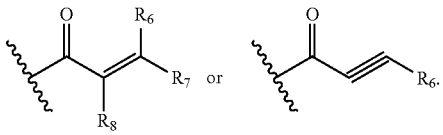

In some embodiments, the compound of Formula (A) is 1-[(3R)-3-[4-amino-3-(4-phenoxyphenyl)pyrazolo[3,4-d]pyrimidin-1-yl]piperidin-1-yl]prop-2-en-1-one. In some embodiments, the patient has cancer. In some embodiments, the patient has a hematological malignancy. In some embodiments, the patient has a relapsed or refractory hematological malignancy. In some embodiments, the patient has a B-cell malignancy. In some embodiments, the patient has a T-cell malignancy. In some embodiments, the patient has a leukemia, a lymphoma, or a myeloma. In some embodiments, the B-cell malignancy is a non-Hodgkin's lymphoma. In some embodiments, the B-cell malignancy is chronic lymphocytic leukemia (CLL). In some embodiments, the B-cell malignancy is a relapsed or refractory B-cell malignancy. In some embodiments, the B-cell malignancy is a relapsed or refractory non-Hodgkin's lymphoma. In some embodiments, the B-cell malignancy is a relapsed or refractory CLL. In some embodiments, the patient has high risk CLL. In some embodiments, the patient has a 17p chromosomal deletion. In some embodiments, the patient has 10%, 20%, 30%, 40%, 50%, 60%, 70%, 80%, 90%, or greater CLL as determined by bone marrow biopsy. In some embodiments, the patient has received one or more prior anticancer agents. In some embodiments, the anticancer agent is selected from among alemtuzumab, bendamustine, bortezomib, CAL-101, chlorambucil, cyclophosphamide, dexamethasone, docetaxel, doxorubicin, endostatineverolimus, etoposide, fludarabine, fostamatinib, hydroxydaunorubicin, ibritumomab, ifosphamide, lenalidomide, mesalazine, ofatumumab, paclitaxel, pentostatin, prednisone, rituximab, temsirolimus, thalidomide, tositumomab, vincristine, or a combination thereof. In some embodiments, the anticancer agent is rituximab. In some embodiments, the anticancer agent is alemtuzumab. In some embodiments, the anticancer agent is fludarabine, cyclophosphamide, and rituximab (FCR). In some embodiments, the anticancer agent is oxaliplatin, fludarabine, cytarabine, rituximab (OFAR). In some embodiments, the amount of the ACK inhibitor compound (e.g., a compound of Formula (A)) prevents or reduces GVHD while maintaining a graft-versus-leukemia (GVL) reaction effective to reduce or eliminate the number of cancerous cells in the blood of the patient. In some embodiments, the cell transplantation is a hematopoietic cell transplantation. In some embodiments, the GVHD is acute GVHD. In some embodiments, the GVHD is chronic GVHD. In some embodiments, the GVHD is sclerodermatous GVHD. In some embodiments, the GVHD is steroid resistant GVHD. In some embodiments, the GVHD is cyclosporin-resistant GVHD. In some embodiments, the GVHD is refractory GVHD. In some embodiments, the GHVD is oral GVHD. In some embodiments, the oral GVHD is reticular oral GVHD. In some embodiments, the oral GVHD is erosive oral GVHD. In some embodiments, the oral GVHD is ulcerative oral GVHD. In some embodiments, the oral GVHD is GVHD of the oral cavity. In some embodiments, the oral GVHD is GVHD of the oropharyngeal region. In some embodiments, the oral GVHD is GVHD of the pharyngeal region. In some embodiments, the oral GVHD is GVHD of the esophageal region. In some embodiments, the oral GVHD is acute oral GVHD. In some embodiments, the oral GVHD is chronic oral GVHD. In some embodiments, the patient exhibits one or more symptoms of GVHD. In some embodiments, the patient has or will receive an allogeneic bone marrow or hematopoietic stem cell transplant. In some embodiments, the ACK inhibitor compound (e.g., a compound of Formula (A)) is administered concurrently with an allogeneic bone marrow or hematopoietic stem cell transplant. In some embodiments, the ACK inhibitor compound (e.g., a compound of Formula (A)) is administered prior to an allogeneic bone marrow or hematopoietic stem cell transplant. In some embodiments, the ACK inhibitor compound (e.g., a compound of Formula (A)) is administered subsequent to an allogeneic bone marrow or hematopoietic stem cell transplant. In some embodiments, the patient is a candidate for receiving HLA-mismatched hematopoietic stem cells. In some embodiments, the patient is a candidate for receiving unrelated donor hematopoietic stem cells, umbilical vein hematopoietic stem cells, or peripheral blood stem cells. In some embodiments, the ACK inhibitor compound (e.g., a compound of Formula (A)) is administered orally. In some embodiments, the ACK inhibitor compound (e.g., a compound of Formula (A)) is administered at a dosage of between about 0.1 mg/kg per day to about 100 mg/kg per day. In some embodiments, the ACK inhibitor compound (e.g., a compound of Formula (A)) is administered at a dosage of about 40 mg/day, about 140 mg/day, about 280 mg/day, about 420 mg/day, about 560 mg/day, or about 840 mg/day. In some embodiments, the ACK inhibitor compound (e.g., a compound of Formula (A)) is administered in combination with other prophylactic agents. In some embodiments, the ACK inhibitor compound (e.g., a compound of Formula (A)) is administered from day 1 to about day 120 following allogeneic bone marrow or hematopoietic stem cell transplant. In some embodiments, the ACK inhibitor compound (e.g., a compound of Formula (A)) is administered from day 1 to about day 1000 following allogeneic bone marrow or hematopoietic stem cell transplant. In some embodiments, the ACK inhibitor compound (e.g., a compound of Formula (A)) is administered in combination with one or more additional therapeutic agents. In some embodiments, the additional therapeutic agent is a corticosteroid. In some embodiments, the therapeutic agent is cyclosporine (CSA), mycophenolate mofetil (MMF) or a combination thereof. In some embodiments, the patient has or will receive a donor lymphocyte infusions (DLI). In some embodiments, the patient is administered one or more DLIs. In some embodiments, the patient is administered two or more DLIs. In some embodiments, the DLI comprises CD3+ lymphocytes. In some embodiments, the patient is administered one or more donor lymphocyte infusions (DLI) following an allogeneic bone marrow or hematopoietic stem cell transplant. In some embodiments, the ACK inhibitor compound (e.g., a compound of Formula (A)) is administered concurrently with a DLI following allogeneic bone marrow or hematopoietic stem cell transplant. In some embodiments, the ACK inhibitor compound (e.g., a compound of Formula (A)) is administered prior to a DLI following an allogeneic bone marrow or hematopoietic stem cell transplant. In some embodiments, the ACK inhibitor compound (e.g., a compound of Formula (A)) is administered following a DLI following an allogeneic bone marrow or hematopoietic stem cell transplant. In some embodiments, the ACK inhibitor compound (e.g., a compound of Formula (A)) is ibrutinib.

In some embodiments, there are provided uses of a compound of Formula (A) with allogeneic hematopoietic stem cells and/or allogeneic T-cells for treating a patient for alleviation of a bone marrow mediated disease, with alleviation of consequently developed graft versus host disease (GVHD), wherein the compound of Formula (A) has the structure:

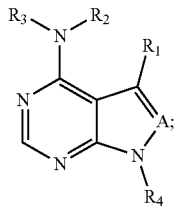

Formula (A)

wherein:

A is N;

$R_1$ is phenyl-O-phenyl or phenyl-S-phenyl;

$R_2$ and $R_3$ are independently H;

$R_4$ is $L_3$-X-$L_4$-G, wherein, $L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;

X is optional, and when present is a bond, —O—, —C(=O)—, —S—, —S(=O)—, —S(=O)$_2$—, —NH—, —NR$_9$—, —NHC(O)—, —C(O)NH—, —NR$_9$C(O)—, —C(O)NR$_9$—, —S(=O)$_2$NH—, —NHS(=O)$_2$—, —S(=O)$_2$NR$_9$—, —NR$_9$S(=O)$_2$—, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl-, aryl-, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;

$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;

or $L_3$, X and $L_4$ taken together form a nitrogen containing heterocyclic ring;

G is

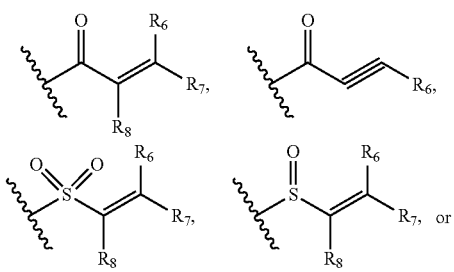

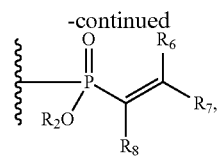

wherein, $R_6$, $R_7$ and $R_8$ are independently selected from among H, halogen, CN, OH, substituted or unsubstituted alkyl or substituted or unsubstituted heteroalkyl or substituted or unsubstituted cycloalkyl, substituted or unsubstituted heterocycloalkyl, substituted or unsubstituted aryl, substituted or unsubstituted heteroaryl;

each $R_9$ is independently selected from among H, substituted or unsubstituted lower alkyl, and substituted or unsubstituted lower cycloalkyl;

each $R_{10}$ is independently H, substituted or unsubstituted lower alkyl, or substituted or unsubstituted lower cycloalkyl; or two $R_{10}$ groups can together form a 5-, 6-, 7-, or 8-membered heterocyclic ring; or $R_{10}$ and $R_{11}$ can together form a 5-, 6-, 7-, or 8-membered heterocyclic ring; or each $R_{11}$ is independently selected from H or substituted or unsubstituted alkyl; or a pharmaceutically acceptable salt thereof, and is administered prior to, concurrently with, or following the administration of the allogeneic hematopoietic stem cells and/or allogeneic T-cells. In some embodiments, $L_3$, X and $L_4$ taken together form a nitrogen containing heterocyclic ring. In some embodiments, the nitrogen containing heterocyclic ring is a piperidine group. In some embodiments, G is

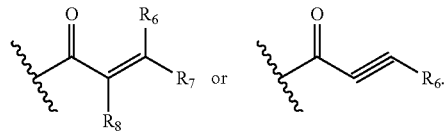

In some embodiments, the compound of Formula (A) is 1-[(3R)-3-[4-amino-3-(4-phenoxyphenyl)pyrazolo[3,4-d]pyrimidin-1-yl]piperidin-1-yl]prop-2-en-1-one. In some embodiments, the patient has cancer. In some embodiments, the patient has a hematological malignancy. In some embodiments, the patient has a relapsed or refractory hematological malignancy. In some embodiments, the patient has a B-cell malignancy. In some embodiments, the patient has a T-cell malignancy. In some embodiments, the patient has a leukemia, a lymphoma, or a myeloma. In some embodiments, the B-cell malignancy is a non-Hodgkin's lymphoma. In some embodiments, the B-cell malignancy is chronic lymphocytic leukemia (CLL). In some embodiments, the B-cell malignancy is a relapsed or refractory B-cell malignancy. In some embodiments, the B-cell malignancy is a relapsed or refractory non-Hodgkin's lymphoma. In some embodiments, the B-cell malignancy is a relapsed or refractory CLL. In some embodiments, the patient has high risk CLL. In some embodiments, the patient has a 17p chromosomal deletion. In some embodiments, the patient has 10%, 20%, 30%, 40%, 50%, 60%, 70%, 80%, 90%, or greater CLL as determined by bone marrow biopsy. In some embodiments, the patient has received one or more prior anticancer agents. In some embodiments, the anticancer agent is selected from among alemtuzumab, bendamustine, bortezomib, CAL-101, chlorambucil, cyclophosphamide, dexamethasone, docetaxel, doxorubicin, endostatineverolimus, etoposide, fludarabine, fostamatinib, hydroxydaunorubicin, ibritumomab, ifosphamide, lenalidomide, mesalazine, ofatumumab, paclitaxel, pentostatin, prednisone, rituximab, temsirolimus, thalidomide, tositumomab, vincristine, or a combination thereof. In some embodiments, the anticancer agent is rituximab. In some embodiments, the anticancer agent is alemtuzumab. In some embodiments, the anticancer agent is fludarabine, cyclophosphamide, and rituximab (FCR). In some embodiments, the anticancer agent is oxaliplatin, fludarabine, cytarabine, rituximab (OFAR). In some embodiments, the amount of the ACK inhibitor compound (e.g., a compound of Formula (A)) prevents or reduces GVHD while maintaining a graft-versus-leukemia (GVL) reaction effective to reduce or eliminate the number of cancerous cells in the blood of the patient. In some embodiments, the cell transplantation is a hematopoietic cell transplantation. In some embodiments, the GVHD is acute GVHD. In some embodiments, the GVHD is chronic GVHD. In some embodiments, the GVHD is sclerodermatous GVHD. In some embodiments, the GVHD is steroid resistant GVHD. In some embodiments, the GVHD is cyclosporin-resistant GVHD. In some embodiments, the GVHD is refractory GVHD. In some embodiments, the GHVD is oral GVHD. In some embodiments, the oral GVHD is reticular oral GVHD. In some embodiments, the oral GVHD is erosive oral GVHD. In some embodiments, the oral GVHD is ulcerative oral GVHD. In some embodiments, the oral GVHD is GVHD of the oral cavity. In some embodiments, the oral GVHD is GVHD of the oropharyngeal region. In some embodiments, the oral GVHD is GVHD of the pharyngeal region. In some embodiments, the oral GVHD is GVHD of the esophageal region. In some embodiments, the oral GVHD is acute oral GVHD. In some embodiments, the oral GVHD is chronic oral GVHD. In some embodiments, the patient exhibits one or more symptoms of GVHD. In some embodiments, the patient has or will receive an allogeneic bone marrow or hematopoietic stem cell transplant. In some embodiments, the ACK inhibitor compound (e.g., a compound of Formula (A)) is administered concurrently with an allogeneic bone marrow or hematopoietic stem cell transplant. In some embodiments, the ACK inhibitor compound (e.g., a compound of Formula (A)) is administered prior to an allogeneic bone marrow or hematopoietic stem cell transplant. In some embodiments, the ACK inhibitor compound (e.g., a compound of Formula (A)) is administered subsequent to an allogeneic bone marrow or hematopoietic stem cell transplant. In some embodiments, the patient is a candidate for receiving HLA-mismatched hematopoietic stem cells. In some embodiments, the patient is a candidate for receiving unrelated donor hematopoietic stem cells, umbilical vein hematopoietic stem cells, or peripheral blood stem cells. In some embodiments, the ACK inhibitor compound (e.g., a compound of Formula (A)) is administered orally. In some embodiments, the ACK inhibitor compound (e.g., a compound of Formula (A)) is administered at a dosage of between about 0.1 mg/kg per day to about 100 mg/kg per day. In some embodiments, the ACK inhibitor compound (e.g., a compound of Formula (A)) is administered at a dosage of about 40 mg/day, about 140 mg/day, about 280 mg/day, about 420 mg/day, about 560 mg/day, or about 840 mg/day. In some embodiments, the ACK inhibitor compound (e.g., a compound of Formula (A)) is administered in combination with other prophylactic agents. In some embodiments, the ACK inhibitor compound (e.g., a compound of Formula (A)) is administered from day 1 to about day 120 following allogeneic bone marrow or hematopoietic stem cell transplant. In some embodiments, the ACK inhibitor compound (e.g., a compound of Formula (A)) is administered from day 1 to about day 1000 following allogeneic bone marrow or hematopoietic stem cell transplant. In some embodiments, the ACK inhibitor compound (e.g., a compound of Formula (A)) is administered in combination with one or more additional therapeutic agents. In some embodiments, the additional therapeutic agent is a corticosteroid. In some embodiments, the therapeutic agent is cyclosporine (CSA), mycophenolate mofetil (MMF) or a combination thereof. In some embodiments, the patient has or will receive a donor lymphocyte infusions (DLI). In some embodiments, the patient is administered one or more DLIs. In some embodiments, the patient is administered two or more DLIs. In some embodiments, the DLI comprises CD3+ lymphocytes. In some embodiments, the patient is administered one or more donor lymphocyte infusions (DLI) following an allogeneic bone marrow or hematopoietic stem cell transplant. In some embodiments, the ACK inhibitor compound (e.g., a compound of Formula (A)) is administered concurrently with a DLI following allogeneic bone marrow or hematopoietic stem cell transplant. In some embodiments, the ACK inhibitor compound (e.g., a compound of Formula (A)) is administered prior to a DLI following an allogeneic bone marrow or hematopoietic stem cell transplant. In some embodiments, the ACK inhibitor compound (e.g., a compound of Formula (A)) is administered following a DLI following an allogeneic bone marrow or hematopoietic stem cell transplant. In some embodiments, the ACK inhibitor compound (e.g., a compound of Formula (A)) is ibrutinib.

Certain Terminology

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, "ACK" and "Accessible Cysteine Kinase" are synonyms. They mean a kinase with an accessible cysteine residue. ACKs include, but are not limited to, BTK, ITK, Bmx/ETK, TEC, EFGR, HER4, HER4, LCK, BLK, C-src, FGR, Fyn, HCK, Lyn, YES, ABL, Brk, CSK, FER, JAK3, SYK. In some embodiments, the ACK is a TEC family kinase. In some embodiments, the ACK is HER4. In some embodiments, the ACK is BTK. In some embodiments, the ACK is ITK.

As used herein, "amelioration" refers to any lessening of severity, delay in onset, slowing of growth, slowing of metastasis, or shortening of duration of HER2-amplified breast cancer, whether permanent or temporary, lasting or transient that can be attributed to or associated with administration of the compound or composition.

The term "Bruton's tyrosine kinase," as used herein, refers to Bruton's tyrosine kinase from *Homo sapiens*, as disclosed in, e.g., U.S. Pat. No. 6,326,469 (GenBank Accession No. NP_000052).

The term "Bruton's tyrosine kinase homolog," as used herein, refers to orthologs of Bruton's tyrosine kinase, e.g., the orthologs from mouse (GenBank Accession No. AAB47246), dog (GenBank Accession No. XP_549139.), rat (GenBank Accession No. NP_001007799), chicken (GenBank Accession No. NP_989564), or zebra fish (GenBank Accession No. XP_698117), and fusion proteins of any of the foregoing that exhibit kinase activity towards one or more substrates of Bruton's tyrosine kinase (e.g., a peptide substrate having the amino acid sequence "AVLESEEEL-YSSARQ" SEQ ID NO:1).

The term "HER4", also known as ERBB4, also known as "V-erb-a erythroblastic leukemia viral oncogene homolog 4" means either (a) the nucleic acid sequence encoding a receptor tyrosine kinase that is a member of the epidermal growth factor receptor subfamily, or (b) the protein thereof. For the nucleic acid sequence that comprises the human HER4 gene see GenBank Accession No. NM_001042599. For the amino acid sequence that comprises the human HER4 protein see GenBank Accession No. NP_001036064.

The term "homologous cysteine," as used herein refers to a cysteine residue found within a sequence position that is homologous to that of cysteine 481 of Bruton's tyrosine kinase, as defined herein. For example, cysteine 482 is the homologous cysteine of the rat ortholog of Bruton's tyrosine kinase; cysteine 479 is the homologous cysteine of the chicken ortholog; and cysteine 481 is the homologous cysteine in the zebra fish ortholog. In another example, the homologous cysteine of TXK, a Tec kinase family member related to Bruton's tyrosine, is Cys 350.

Figure 7:
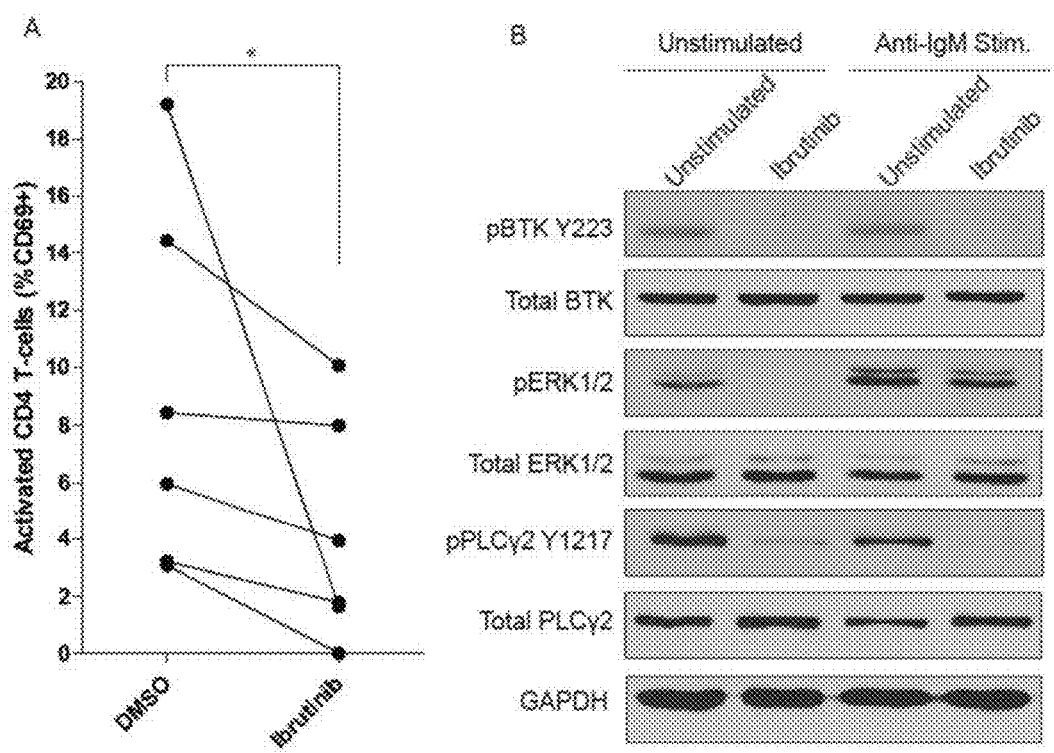
FIG. 7 exemplifies that ibrutinib limits activation of T-cells and B-cells from patients with active cGVHD. Primary CD4+ T-cells were isolated from patients with active cGVHD, pretreated with 1 µM ibrutinib (or DMSO), and stimulated using anti-CD3 for 6 hours. Panel A shows a graph depicting CD69+ CD4+ T-cell percentage for each patient. "*" indicates p<0.05. Panel B shows an image of an immunoblot analysis of BTK, ERK, and PLCγ2 in B-cells isolated from patients with cGVHD were pretreated with 1 µM ibrutinib (or DMSO), and stimulated using anti-IgM for 45 minutes. Data are representative of three experiments on three separate patients.

The term "irreversible BTK inhibitor," as used herein, refers to an inhibitor of BTK that can form a covalent bond with an amino acid residue of BTK. In one embodiment, the irreversible inhibitor of BTK can form a covalent bond with a Cys residue of BTK; in particular embodiments, the irreversible inhibitor can form a covalent bond with a Cys 481 residue (or a homolog thereof) of BTK or a cysteine residue in the homologous corresponding position of another tyrosine kinase, as shown in FIG. 7.

As used herein, the term "pERK" refers to phosphorylated ERK1 and ERK2 at Thr202/Tyr 204 as detected by commercially available phospho-specific antibodies (e.g. Cell Signaling Technologies #4377).

The terms "individual", "patient" and "subject" are used interchangeably. These terms refer to a mammal (e.g., a human) which is the object of treatment, or observation. The term is not to be construed as requiring the supervision of a medical practitioner (e.g., a physician, physician's assistant, nurse, orderly, or hospice care worker).

The terms "treat," "treating" or "treatment", as used herein, include lessening of severity of GVHD, delay in onset of GVHD, causing regression of GVHD, relieving a condition caused by of GVHD, or stopping symptoms which result from GVHD. The terms "treat," "treating" or "treatment", include, but are not limited to, prophylactic and/or therapeutic treatments.

As used herein, oral GVHD refers to local manifestation of GVHD in the oral cavity, oropharynx, pharyngeal, or esophageal regions.

Graft Versus Host Disease

Described herein are methods of preventing the occurrence of graft versus host disease (GVHD) or reducing the severity of GVHD occurrence in a patient requiring cell transplantation comprising administering to the patient a composition comprising a therapeutically-effective amount of an ACK inhibitor compound (e.g., an ITK or BTK inhibitor, such as, ibrutinib). In some embodiments, the patient requires hematopoietic cell transplantation. In some embodiments, the patient requires peripheral blood stem cell transplantation. In some embodiments, the patient requires bone marrow transplantation. In some embodiments, the ACK inhibitor compound is administered prior to administration of the cell transplant. In some embodiments, the ACK inhibitor compound is administered subsequent to administration of the cell transplant. In some embodiments, the ACK inhibitor compound is administered concurrently with administration of the cell transplant. In some embodiments, the patient exhibits one or more symptoms of GVHD. In some embodiments, the patient exhibits one or more symptoms of acute GVHD. In some embodiments, the patient exhibits one or more symptoms of chronic GVHD. In some embodiments, the GVHD is sclerodermatous GVHD. Exemplary symptoms of GVHD include, but are not limited to, skin rash or reddened areas on the skin, raised skin, blistering, thickening or tightening of the skin, yellow discoloration of the skin and/or eyes, abnormal blood test results, nausea, vomiting, diarrhea, abdominal swelling, abdominal cramping, increased dryness or irritation of the eyes, vision changes, dry mouth, white patches inside the mouth, pain or sensitivity to spicy foods, shortness of breath, difficulty swallowing, pain with swallowing, weight loss, fatigue, muscle weakness, muscle pain, increased urinary frequency, burning or bleeding with urination, vaginal dryness or tightening, or penile dysfunction.

In some embodiments, the patient exhibits one or more symptoms of oral GVHD. In some embodiments, the patient exhibits one or more symptoms of acute oral GVHD. In some embodiments, the patient exhibits one or more symptoms of chronic oral GVHD. Exemplary symptoms of oral GVHD include, but are not limited to, oral tissue inflammation, dry mouth, punctate or generalized mucosal erythema, white striae or papules on the oral mucosa and lips, mucosal erosion-desquamation-ulceration, pain or sensitivity to spicy foods, difficulty swallowing, pain with swallowing, pharyngo-esophageal stricture, xerostomia, lichen planus, poor bolus control, pharyngeal retention, excessive mucous secretion, oral tissue inflammation, and ulceration. In some embodiments, the patient suffers from refractory GVHD. In some embodiments, the oral GVHD is reticular oral GVHD. In some embodiments, the oral GVHD is erosive oral GVHD. In some embodiments, the oral GVHD is ulcerative oral GVHD.

In some embodiments, the patient suffers from steroid resistant GVHD. In some embodiments, the steroid resistant GVHD is acute GVHD. In some embodiments, the steroid resistant GVHD is chronic GVHD. In some embodiments, the patient suffers from cyclosporin-resistant GVHD.

Described herein are methods of preventing the occurrence of graft versus host disease (GVHD) or reducing the severity of GVHD occurrence in a patient requiring stem cell transplantation comprising administering to the patient a composition comprising a therapeutically-effective amount of an ACK inhibitor compound (e.g., an ITK or BTK inhibitor, such as for example ibrutinib). In some embodiments, the patient requires hematopoietic stem cell transplantation. In some embodiments, the patient requires peripheral blood stem cell transplantation. In some embodiments, the patient requires bone marrow transplantation. In some embodiments, the ACK inhibitor compound is administered prior to administration of the stem cell transplant. In some embodiments, the ACK inhibitor compound is administered subsequent to administration of the stem cell transplant. In some embodiments, the ACK inhibitor compound is administered concurrently with administration of the stem cell transplant. In some embodiments, the ACK inhibitor compound is administered prior to, subsequent to, or concurrently with administration of allogeneic hematopoietic stem cells and/or allogeneic T-cells.

Further described herein are methods of treating a patient for alleviation of a bone marrow mediated disease, with alleviation of consequently developed graft versus host disease (GVHD), comprising administering to the patient allogeneic hematopoietic stem cells and/or allogeneic T-cells, wherein a therapeutically effective amount of an ACK inhibitor compound (e.g., an ITK or BTK inhibitor, such as, ibrutinib) is administered prior to, subsequently, or concurrently with administration of the allogeneic hematopoietic stem cells and/or allogeneic T-cells.

Treatment of proliferative blood disorders, such as leukemia, lymphoma and myeloma usually involves one or more forms of chemotherapy and/or radiation therapy. These treatments destroy malignant cells, but also destroy healthy blood cells. Allogeneic hematopoietic cell transplantation is an effective therapy for the treatment of many hematologic malignancies, including, for example, B-cell and T-cell malignancies. In allogeneic hematopoietic cell transplantation, bone marrow (or, in some cases, peripheral blood) from an unrelated or a related (but not identical twin) donor is used to replace the healthy blood cells destroyed in the cancer patient. The bone marrow (or peripheral blood) contains stem cells, which are the precursors to all the different cell types (e.g., red cells, phagocytes, platelets and lymphocytes) found in blood. Allogeneic hematopoietic cell transplantation is known to have both a restorative effect and a curative effect. The restorative effect arises from the ability of the stem cells to repopulate the cellular components of blood. The curative properties of allogeneic hematopoietic cell transplantation derive largely from a graft-versus-leukemia (GVL) effect. The transplanted hematopoietic cells from the donor (specifically, the T lymphocytes) attack the cancerous cells, enhancing the suppressive effects of the other forms of treatment. Essentially, the GVL effect comprises an attack on the cancerous cells by the blood cells derived from the transplantation, making it less likely that the malignancy will return after transplant. Controlling the GVL effect prevents escalation of the GVL effect into GVHD. A similar effect against tumors (graft-versus tumor) is also known.

Allogeneic hematopoietic cell transplantation is often toxic to the patient. This toxicity arises from the difficulty in dissociating the GVL or GVT effect from graft-versus-host disease (GVHD), an often-lethal complication of allogeneic BMT.

GVHD is a major complication of allogeneic hematopoietic cell transplant (HCT). GVHD is an inflammatory disease initiated by T cells in the donor graft that recognize histocompatibility and other tissue antigens of the host and GVHD is mediated by a variety of effector cells and inflammatory cytokines. GVHD presents in both acute and chronic forms. The most common symptomatic organs are the skin, liver, and gastrointestinal tract, including the oral cavity and oropharyngeal regions. GVHD may involve other organs such as the lung. Treatment of GVHD is generally only 50-75% successful; the remainder of patients generally do not survive. The risk and severity of this immune-mediated condition are directly related to the degree of mismatch between a host and the donor of hematopoietic cells. For example, GVHD develops in up to 30% of recipients of human leukocyte antigen (HLA)-matched sibling marrow, in up to 60% of recipients of HLA-matched unrelated donor marrow, and in a higher percentage of recipient of HLA-mismatched marrow. Patients with mild intestinal GVHD present with anorexia, nausea, vomiting, abdominal pain and diarrhea, whereas patients with severe GVHD are disabled by these symptoms. If untreated, symptoms of intestinal GVHD persist and often progress; spontaneous remissions are unusual. In its most severe form, GVHD leads to necrosis and exfoliation of most of the epithelial cells of the intestinal mucosa, a frequently fatal condition. The symptoms of acute GVHD usually present within 100 days of transplantation. The symptoms of chronic GVHD usually present somewhat later, up to three years after allogeneic HCT, and are often proceeded by a history of acute GVHD.

Oral manifestations of GVHD are seen in both acute GVHD (aGVHD) and chronic GVHD (cGVHD). Oral involvement ranges between 33% and 75% for patients with aGVHD and up to about 80% for those with cGVHD. Involvement of the salivary glands may cause dryness of the oral mucosa and oral pain may be the first presenting symptom. Oral lesions in GVHD may be lichenoid or lupus-like in appearance. Oral findings of aGVHD include painful desquamative, erythematous, and ulcerative mucosal lesions. In cGVHD, they are lichenoid with associated erythema and ulcerations; additionally, they may be associated with sicca syndrome characterized by xerostomia and progressive salivary gland atrophy. Oral complications include pain due to the mucosal changes, altered or reduced taste, and may have a potential impact on speech, deglutition, and use of oral prostheses (when present). Oral infection, particularly due to *Candida* species, and dental demineralization and caries may also occur. Oral manifestations of cGVHD can significantly affect the life quality of patients through discomfort and impairment of the oral intake leading to malnutrition and increased morbidity.

The conventional management of oral cGVHD consists of systemic immunosuppressive therapies combined with proper oral hygiene and the judicious use of topical steroids. However, for patients with oral cGVHD as the most significant clinical finding, the use of systemic immunosuppressants may result in immunosuppression of the host with attendant systemic complications. In addition, some patients experience considerable and refractory oral complications, even with maximum doses of systemic immunosuppressants.

First-line therapy of oral GVHD is mostly systemic in nature, consisting of cyclosporin and steroids. The most common salvage treatments for cGVHD are thalidomide, tacrolimus, mycophenolate mofetil, T cell depletion by Campath-1, and phototherapy. Oral GVHD is often refractory to conventional treatment and therefore complementary topical treatment is required. Several agents are currently used for local treatments such as palliative rinses, topical immunosuppressive agents, thalidomide, retinoids, and phototherapy for oral GVHD.

Described herein are methods of preventing the occurrence of graft versus host disease (GVHD) or reducing the severity of GVHD occurrence in a patient requiring cell transplantation comprising administering to the patient a composition comprising a therapeutically-effective amount of an ACK inhibitor compound (e.g., an ITK or BTK inhibitor, such as for example ibrutinib). In some embodiments, the patient requires hematopoietic cell transplantation. Further described herein are methods of treating a patient for alleviation of a bone marrow mediated disease, with alleviation of consequently developed graft versus host disease (GVHD), comprising administering to the patient allogeneic hematopoietic stem cells and/or allogeneic T-cells, wherein a therapeutically effective amount of an ACK inhibitor compound (e.g., an ITK or BTK inhibitor, such as ibrutinib) is administered prior to, concurrently with, or following the allogeneic hematopoietic stem cells and/or allogeneic T-cells. In some embodiments, the patient has cancer. In some embodiments, the patient has a hematologic malignancy. In some embodiments, the patient has a B-cell malignancy. In some embodiments, the patient has a T-cell malignancy. In some embodiments, the patient has a leukemia, lymphoma, or a myeloma. In some embodiments, the B-cell malignancy is a non-Hodgkin's lymphoma. In some embodiments, the B-cell malignancy is chronic lymphocytic leukemia (CLL). In some embodiments, the B-cell malignancy is a relapsed or refractory B-cell malignancy. In some embodiments, the B-cell malignancy is a relapsed or refractory non-Hodgkin's lymphoma. In some embodiments, the B-cell malignancy is a relapsed or refractory CLL. In some embodiments, the patient has high risk CLL. In some embodiments, the patient has a 17p chromosomal deletion. In some embodiments, the patient has 10%, 20%, 30%, 40%, 50%, 60%, 70%, 80%, 90%, or greater CLL as determined by bone marrow biopsy. In some embodiments, the patient has received one or more prior anticancer agents. In some embodiments, the anticancer agent is selected from among alemtuzumab, bendamustine, bortezomib, CAL-101, chlorambucil, cyclophosphamide, dexamethasone, docetaxel, doxorubicin, endostatineverolimus, etoposide, fludarabine, fostamatinib, hydroxydaunorubicin, ibritumomab, ifosphamide, lenalidomide, mesalazine, ofatumumab, paclitaxel, pentostatin, prednisone, rituximab, temsirolimus, thalidomide, tositumomab, vincristine, or a combination thereof. In some embodiments, the anticancer agent is rituximab. In some embodiments, the anticancer agent is alemtuzumab. In some embodiments, the anticancer agent is fludarabine, cyclophosphamide, and rituximab (FCR). In some embodiments, the anticancer agent is oxaliplatin, fludarabine, cytarabine, rituximab (OFAR). In some embodiments, a compound disclosed herein prevents or reduces GVHD while maintaining a graft-versus-leukemia (GVL) reaction effective to reduce or eliminate the number of cancerous cells in the blood of the patient. In some embodiments, the GVHD is acute GVHD. In some embodiments, the GVHD is chronic GVHD. In some embodiments, the GHVD is oral GVHD. In some embodiments, the oral GVHD is GVHD of the oral cavity. In some embodiments, the oral GVHD is GVHD of the oropharyngal region. In some embodiments, the oral GVHD is GVHD of the pharyngeal region. In some embodiments, the oral GVHD is GVHD of the esophageal region. In some embodiments, the oral GVHD is acute oral GVHD. In some embodiments, the oral GVHD is chronic oral GVHD. In some embodiments, the patient has or will receive an allogeneic bone marrow or hematopoietic stem cell transplant. In some embodiments, an ACK inhibitor compound disclosed herein is administered concurrently with an allogeneic bone marrow or hematopoietic stem cell transplant. In some embodiments, an ACK inhibitor compound disclosed herein is administered prior to an allogeneic bone marrow or hematopoietic stem cell transplant. In some embodiments, an ACK inhibitor compound disclosed herein is administered subsequent to an allogeneic bone marrow or hematopoietic stem cell transplant. In some embodiments, the patient is a candidate for receiving HLA-mismatched hematopoietic stem cells. In some embodiments, the patient is a candidate for receiving unrelated donor hematopoietic stem cells, umbilical vein hematopoietic stem cells, or peripheral blood stem cells. In some embodiments, an ACK inhibitor compound disclosed herein is administered subsequent to a patient exhibiting one or more symptoms of oral GVHD, wherein the patient an allogeneic bone marrow or hematopoietic stem cell transplant.

In some embodiments, the patient is administered a donor lymphocyte infusions (DLI). A donor lymphocyte infusion is a blood cell infusion in which CD3+ lymphocytes from the original stem cell donor are infused, after the transplant, to augment an anti-tumor immune response or ensure that the donor stem cells remain engrafted. These donated white blood cells contain cells of the immune system that can recognize and destroy cancer cells. In some embodiments, the therapy induces a remission of the patient's cancer by a graft-versus-tumor effect (GVT). In some embodiments, the donor T-cells can attack and control the growth of residual cancer cells providing the GVT effect. In some embodiments, the patient is administered one or more donor lymphocyte infusions (DLI). In some embodiments, the DLI comprises CD3+ lymphocytes. In some embodiments, the patient is administered one or more donor lymphocyte infusions (DLI) following an allogeneic bone marrow or hematopoietic stem cell transplant. In some embodiments, the compound of Formula (A) is administered concurrently with a DLI following allogeneic bone marrow or hematopoietic stem cell transplant. In some embodiments, the compound of Formula (A) is administered prior to a DLI following an allogeneic bone marrow or hematopoietic stem cell transplant. In some embodiments, the compound of Formula (A) is administered following a DLI following an allogeneic bone marrow or hematopoietic stem cell transplant. In some embodiments, the compound of Formula (A) is ibrutinib.

In some embodiments, the patient has a non-Hodgkin's lymphoma. In some embodiments, the patient has a Hodgkin's lymphoma. In some embodiments, the patient has a B-cell malignancy. In some embodiments, the B-cell malignancy is chronic lymphocytic leukemia (CLL), small lymphocytic lymphoma (SLL), diffuse large B-cell lymphoma (DLBCL), follicular lymphoma (FL), activated B-cell diffuse large B-cell lymphoma (ABC-DLBCL), germinal center diffuse large B-cell lymphoma (GCB DLBCL), primary mediastinal B-cell lymphoma (PMBL), Burkitt's lymphoma, immunoblastic large cell lymphoma, precursor B-lymphoblastic lymphoma, mantle cell lymphoma (MCL), B cell prolymphocytic leukemia, lymphoplasmacytic lymphoma, Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the patient has a T-cell malignancy. In some embodiments, the T-cell malignancy is peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas. In some embodiments, the subject has multiple myeloma.

In some embodiments, the patient has a relapsed or refractory hematologic cancer. In some embodiments, the relapsed or refractory hematologic cancer is a leukemia, a lymphoma, or a myeloma. In some embodiments, the relapsed or refractory hematologic cancer is a non-Hodgkin's lymphoma. In some embodiments, the relapsed or refractory hematologic cancer is a Hodgkin's lymphoma. In some embodiments, the relapsed or refractory hematologic cancer is a B-cell malignancy. In some embodiments, the B-cell malignancy is chronic lymphocytic leukemia (CLL), small lymphocytic lymphoma (SLL), diffuse large B-cell lymphoma (DLBCL), follicular lymphoma (FL), activated B-cell diffuse large B-cell lymphoma (ABC-DLBCL), germinal center diffuse large B-cell lymphoma (GCB DLBCL), primary mediastinal B-cell lymphoma (PMBL), Burkitt's lymphoma, immunoblastic large cell lymphoma, precursor B-lymphoblastic lymphoma, mantle cell lymphoma (MCL), B cell prolymphocytic leukemia, lymphoplasmacytic lymphoma, Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the relapsed or refractory hematologic cancer is a T-cell malignancy. In some embodiments, the T-cell malignancy is peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas. In some embodiments, the subject has a relapsed or refractory multiple myeloma. In some embodiments, the patient has a B-cell malignancy. In some embodiments, the B-cell malignancy is a non-Hodgkin's lymphoma. In some embodiments, the B-cell malignancy is chronic lymphocytic leukemia (CLL). In some embodiments, the B-cell malignancy is a relapsed or refractory B-cell malignancy. In some embodiments, the B-cell malignancy is a relapsed or refractory non-Hodgkin's lymphoma. In some embodiments, the B-cell malignancy is a relapsed or refractory CLL.

In some embodiments, the patient exhibits one or more symptoms of a hematologic cancer. In some embodiments, the subject exhibits one or more symptoms of a B-cell malignancy. In some embodiments, the subject exhibits one or more symptoms of a leukemia, a lymphoma, or a myeloma. In some embodiments, the subject exhibits one or more symptoms such as, but not limited to, abnormal B-cell function, abnormal B-cell size or shape, abnormal B-cell count, fatigue, fever, night sweats, frequent infection, enlarged lymph nodes, paleness, anemia, easy bleeding or bruising, loss of appetite, weight loss, bone or joint pain, headaches, and petechiae.

In some embodiments, the subject has a high risk of cancer recurrence. In some embodiments, the subject is a mammal, such as, but not limited to a human, a non-human primate, mouse, rat, rabbit, goat, dog, cat, or cow. In some embodiments, the mammal is a human. In some embodiments, a high risk of cancer recurrence is determined based on the expression or presence of a biomarker. In some embodiments, the biomarker includes PMSB1 P11A G/C heterozygote, CD68, suppressor of cytokine signaling 1 (SOCS1), LIM domain only 2 (LMO2), CD137, or a combination thereof.

Combination Therapies

Described herein methods of preventing the occurrence of graft versus host disease (GVHD) or reducing the severity of GVHD occurrence in a patient requiring cell transplantation comprising co-administering to the individual a composition comprising a therapeutically-effective amount of an ACK inhibitor compound (e.g., an ITK or BTK inhibitor, such as for example ibrutinib) and an additional therapeutic agent. Further described herein are methods of treating a patient for alleviation of a bone marrow mediated disease, with alleviation of consequently developed oral graft versus host disease (GVHD), comprising co-administering to the individual a composition comprising a therapeutically-effective amount of an ACK inhibitor compound (e.g., an ITK or BTK inhibitor, such as for example ibrutinib) and an additional therapeutic agent prior to, subsequent to or concurrently with the allogeneic hematopoietic stem cells and/or allogeneic T-cells. In some embodiments, the individual is administered an additional therapy such as, but not limited to, extracorporeal photopheresis or infusion of mesenchymal stem cells or donor lymphocytes.

In some embodiments, the additional therapeutic agent is an anti-GVHD therapeutic agent. In some embodiments, the anti-GVHD therapeutic agent is an immunosuppressive drug. In some embodiments, the immunosuppressive drug includes cyclosporine, tacrolimus, methotrexate, mycophenolate mofetil, corticosteroids, azathioprine or antithymocyte globulin (ATG). In some embodiments, the immunosuppressive drug is a monoclonal antibody (for example, anti-CD3, anti-CD5, and anti-IL-2 antibodies). In some embodiments, the immunosuppressive drug is Mycophenolate mofetil, Alemtuzumab, Antithymocyte globulin (ATG), Sirolimus, Tacrolimus, Thalidomide, Daclizumab, Infliximab, or Clofazimine are of use to treat chronic GVHD. In some embodiments, the additional therapeutic agent is denileukin diftitox, defibrotide, budesonide, beclomethasone dipropionate, or pentostatin.

In some embodiments, the additional therapeutic agent is an IL-6 receptor inhibitor. In some embodiments, the additional therapeutic agent is an IL-6 receptor antibody.

In some embodiments, the additional therapeutic agent is a TLR5 agonist.

In some embodiments, the patient undergoes an additional therapy such as extracorporeal photopheresis or infusion of mesenchymal stem cells or donor lymphocytes.

In some embodiments, the additional therapeutic agent is a topically active corticosteroid (TAC). In some embodiments, the TAC is beclomethasone dipropionate, alciometasone dipropionate, busedonide, 22S busesonide, 22R budesonide, beclomethasone-17-monopropionate, betamethasone, clobetasol propionate, dexamethasone, diflorasone diacetate, flunisolide, fluocinonide, flurandrenolide, fluticasone propionate, halobetasol propionate, halcinocide, mometasone furoate, triamcinalone acetonide or a combination thereof.

In some embodiments, the additional therapeutic agent is an antifungal agent. In some embodiments, the additional therapeutic agent is nystatin, clotrimazole, amphotericin, fluconazole itraconazole or a combination thereof.

In some embodiments, the additional therapeutic agent is a sialogogue. In some embodiments, the additional therapeutic agent is cevimeline, pilocarpine, bethanechol or a combination thereof.

In some embodiments, the additional therapeutic agent is a topical anesthetic. In some embodiments, the additional therapeutic agent is lidocaine, dyclonine, diphenhydramine, doxepin or a combination thereof.

In the methods described herein, any suitable technique for chemotherapy, biotherapy, immunosuppression and radiotherapy known in the art may be used. For example, the chemotherapeutic agent may be any agent that exhibits an oncolytic effect against cancer cells or neoplastic cells of the subject. For example, the chemotherapeutic agent may be, without limitation, an anthracycline, an alkylating agent, an alkyl sulfonate, an aziridine, an ethylenimine, a methyhnelamine, a nitrogen mustard, a nitrosourea, an antibiotic, an antimetabolite, a folic acid analogue, a purine analogue, a pyrimidine analogue, an enzyme, a podophyllotoxin, a platinum-containing agent or a cytokine. Preferably, the chemotherapeutic agent is one that is known to be effective against the particular cell type that is cancerous or neoplastic. In some embodiments, the chemotherapeutic agent is effective in the treatment of hematopoietic malignancies, such as thiotepa, cisplatin-based compounds, and cyclophosphamide. Cytokines include interferons, G-CSF, erythropoietin, GM-CSF, interleukins, parathyroid hormone, and the like. Biotherapies include alemtuzumab, rituximab, bevacizumab, vascular disrupting agents, lenalidomide, and the like. Radiosensitizers include nicotinomide, and the like.

In some embodiments, the ACK inhibitor is administered in combination with a chemotherapeutic agent or biologic agent selected from among an antibody, a B cell receptor pathway inhibitor, a T cell receptor inhibitor, a PI3K inhibitor, an IAP inhibitor, an mTOR inhibitor, a radioimmunotherapeutic, a DNA damaging agent, a histone deacetylase inhibitor, a protein kinase inhibitor, a hedgehog inhibitor, an Hsp90 inhibitor, a telomerase inhibitor, a Jak1/2 inhibitor, a protease inhibitor, an IRAK inhibitor, a PKC inhibitor, a PARP inhibitor, a CYP3A4 inhibitor, an AKT inhibitor, an Erk inhibitor, a proteosome inhibitor, an alkylating agent, an anti-metabolite, a plant alkaloid, a terpenoid, a cytotoxin, a topoisomerase inhibitor, or a combination thereof. In some embodiments, the B cell receptor pathway inhibitor is a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, a CD22 inhibitor, a Bcl-2 inhibitor, an IRAK 1/4 inhibitor, a JAK inhibitor (e.g., ruxolitinib, baricitinib, CYT387, lestauritinib, pacritinib, TG101348, SAR302503, tofacitinib (Xeljanz), etanercept (Enbrel), GLPG0634, R256), a microtubule inhibitor, a Topo II inhibitor, anti-TWEAK antibody, anti-IL17 bispecific antibody, a CK2 inhibitor, anaplastic lymphoma kinase (ALK) and c-Met inhibitors, demethylase enzyme inhibitors such as demethylase, HDM, LSDI and KDM, fatty acid synthase inhibitors such as spirocyclic piperidine derivatives, glucocorticosteriod receptor agonist, fusion anti-CD 19-cytotoxic agent conjugate, antimetabolite, p70S6K inhibitor, immune modulators, AKT/PKB inhibitor, procaspase-3 activator PAC-1, BRAF inhibitor, lactate dehydrogenase A (LDH-A) inhibitor, CCR2 inhibitor, CXCR4 inhibitor, chemokine receptor antagonists, DNA double stranded break repair inhibitors, NOR202, GA-101, TLR2 inhibitor, or a combination thereof. In some embodiments, the T cell receptor inhibitor is Muromonab-CD3. In some embodiments, the chemotherapeutic agent is selected from among rituximab (rituxan), carfilzomib, fludarabine, cyclophosphamide, vincristine, prednisalone. chlorambucil, ifosphamide, doxorubicin, mesalazine, thalidomide, revlimid, lenalidomide, temsirolimus, everolimus, fostamatinib, paclitaxel, docetaxel, ofatumumab, dexamethasone, bendamustine, prednisone, CAL-101, ibritumomab, tositumomab, bortezomib, pentostatin, endostatin, ritonavir, ketoconazole, an anti-VEGF antibody, herceptin, cetuximab, cisplatin, carboplatin, docetaxel, erlotinib, etopiside, 5-fluorouracil, gemcitabine, ifosphamide, imatinib mesylate (Gleevec), gefitinib, erlotinib, procarbazine, prednisone, irinotecan, leucovorin, mechlorethamine, methotrexate, oxaliplatin, paclitaxel, sorafenib, sunitinib, topotecan, vinblastine, GA-1101, dasatinib, Sipuleucel-T, disulfiram, epigallocatechin-3-gallate, salinosporamide A, ONX0912, CEP-18770, MLN9708, R-406, lenalinomide, spirocyclic piperidine derivatives, quinazoline carboxamide azetidine compounds, thiotepa, DWA2114R, NK121, IS 3 295, 254-S, alkyl sulfonates such as busulfan, improsulfan and piposulfan; aziridines such as benzodepa, carboquone, meturedepa and uredepa; ethylenimine, methylmelamines such as altretamine, triethylenemelamine, triethylenephosphoramide, triethylenethiophosphoramide and trimethylmelamine; chlornaphazine; estramustine; ifosfamide; mechlorethamine; oxide hydrochloride; novobiocin; phenesterine; prednimustine; trofosfamide; uracil mustard; nitrosoureas such as carmustine, chlorozotocin, fotemustine, lomustine, nimustine, ranimustine; antibiotics such as aclacinomycins, actinomycin, anthramycin, azaserine, bleomycins, cactinomycin, calicheamicin, carubicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatrexate; defosfamide; demecolcine; diaziquone; eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; polysaccharide-K; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; cytosine arabinoside; taxoids, e.g., paclitaxel and docetaxel; 6-thioguanine; mercaptopurine; methotrexate; platinum analogs; platinum; etoposide (VP-16); ifosfamide; mitomycin C; mitoxantrone; vincristine; vinorelbine; Navelbine; Novantrone; teniposide; daunomycin; aminopterin; Xeloda; ibandronate; CPT1 1; topoisomerase inhibitor RFS 2000; difluoromethylornithine (DMFO); retinoic acid; esperamycins; capecitabine; and pharmaceutically acceptable salts, acids or derivatives of; anti-hormonal agents such as anti-estrogens including for example tamoxifen, raloxifene, aromatase inhibiting 4(5)-imidazoles, 4-hydroxytamoxifen, trioxifene, keoxifene, LY117018, onaprostone and toremifene (Fareston); antiandrogens such as flutamide, nilutamide, bicalutamide, leuprolide and goserelin; ACK inhibitors such as AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) or a combination thereof.

When an additional agent is co-administered with an ACK inhibitor, the additional agent and the ACK inhibitor do not have to be administered in the same pharmaceutical composition, and are optionally, because of different physical and chemical characteristics, administered by different routes. The initial administration is made, for example, according to established protocols, and then, based upon the observed effects, the dosage, modes of administration and times of administration are modified.

By way of example only, if a side effect experienced by an individual upon receiving an ACK inhibitor is nausea, then it is appropriate to administer an anti-emetic agent in combination with the ACK inhibitor.

Or, by way of example only, the therapeutic effectiveness of an ACK inhibitor described herein is enhanced by administration of an adjuvant (i.e., by itself the adjuvant has minimal therapeutic benefit, but in combination with another therapeutic agent, the overall therapeutic benefit to the patient is enhanced). Or, by way of example only, the benefit experienced by an individual is increased by administering an ACK inhibitor described herein with another therapeutic agent (which also includes a therapeutic regimen) that also has therapeutic benefit. In any case, regardless of the disease, disorder being treated, the overall benefit experienced by the patient is in some embodiments simply additive of the two therapeutic agents or in other embodiments, the patient experiences a synergistic benefit.

The particular choice of compounds used will depend upon the diagnosis of the attending physicians and their judgment of the condition of the patient and the appropriate treatment protocol. The compounds are optionally administered concurrently (e.g., simultaneously, essentially simultaneously or within the same treatment protocol) or sequentially, depending upon the nature of the disorder, the condition of the patient, and the actual choice of compounds used. The determination of the order of administration, and the number of repetitions of administration of each therapeutic agent during a treatment protocol, is based on an evaluation of the disease being treated and the condition of the patient.

In some embodiments, therapeutically-effective dosages vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disorder being treated and so forth. In addition, when co-administered with an additional therapeutic agent, an ACK inhibitor described herein is administered either simultaneously with the additional therapeutic agent, or sequentially. If administered sequentially, the attending physician will decide on the appropriate sequence of administering protein in combination with the biologically active agent(s).

If the additional therapeutic agent and the ACK inhibitor are administered simultaneously, the multiple therapeutic agents are optionally provided in a single, unified form, or in multiple forms (by way of example only, either as a single pill or as two separate pills). In some embodiments, one of the therapeutic agents is given in multiple doses, or both are given as multiple doses. If not simultaneous, the timing between the multiple doses is from about more than zero weeks to less than about four weeks. In addition, the combination methods, compositions and formulations are not to be limited to the use of only two agents; the use of multiple therapeutic combinations is also envisioned.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

In some embodiments, the pharmaceutical agents which make up the combination therapy disclosed herein are administered in a combined dosage form, or in separate dosage forms intended for substantially simultaneous administration. In some embodiments, the pharmaceutical agents that make up the combination therapy are administered sequentially, with either therapeutic compound being administered by a regimen calling for two-step administration. In some embodiments, the two-step administration regimen calls for sequential administration of the active agents or spaced-apart administration of the separate active agents. The time period between the multiple administration steps ranges from a few minutes to several hours, depending upon the properties of each pharmaceutical agent, such as potency, solubility, bioavailability, plasma half-life and kinetic profile of the pharmaceutical agent. In some embodiments, circadian variation of the target molecule concentration determines the optimal dose interval.

In some embodiments, the ACK inhibitor compound and the additional therapeutic agent are administered in a unified dosage form. In some embodiments, the ACK inhibitor compound and the additional therapeutic agent are administered in separate dosage forms. In some embodiments, the ACK inhibitor compound and the additional therapeutic agent are administered simultaneously or sequentially.

Administration

Described herein are methods of preventing the occurrence of graft versus host disease (GVHD) or reducing the severity of GVHD occurrence in a patient requiring cell transplantation comprising administering to the patient a composition comprising a therapeutically-effective amount of an ACK inhibitor compound (e.g., an ITK or BTK inhibitor, such as for example ibrutinib).

Further described herein are methods of reducing the severity of GVHD occurrence in a patient requiring cell transplantation comprising administering to the patient a composition comprising a therapeutically-effective amount of an ACK inhibitor compound (e.g., an ITK or BTK inhibitor, such as for example ibrutinib).

Further described herein are methods of treating a patient for alleviation of a bone marrow mediated disease, with alleviation of consequently developed graft versus host disease (GVHD), comprising administering to the patient allogeneic hematopoietic stem cells and/or allogeneic T-cells, wherein a therapeutically effective amount of an ACK inhibitor compound (e.g., an ITK or BTK inhibitor, such as for example ibrutinib) is administered prior to or concurrently with the allogeneic hematopoietic stem cells and/or allogeneic T-cells. In some embodiments, the ACK inhibitor compound is (R)-1-(3-(4-amino-3-(4-phenoxyphenyl)-1H-pyrazolo[3,4-d]pyrimidin-1-yl)piperidin-1-yl) prop-2-en-1-one (i.e., PCI-32765/ibrutinib).

The ACK inhibitor compound (e.g., an ITK or BTK inhibitor, such as for example ibrutinib) is administered before, during or after the development of GVHD. In some embodiments, the ACK inhibitor compound (e.g., an ITK or BTK inhibitor, such as for example ibrutinib) is used as a prophylactic and is administered continuously to subjects with a propensity to develop GVHD (e.g., allogeneic transplant recipients). In some embodiments, the ACK inhibitor compound (e.g., an ITK or BTK inhibitor, such as for example ibrutinib) is administered to an individual during or as soon as possible after the development of GVHD. In some embodiments, the administration of the ACK inhibitor compound (e.g., an ITK or BTK inhibitor, such as for example ibrutinib) is initiated within the first 48 hours of the onset of the symptoms, within the first 6 hours of the onset of the symptoms, or within 3 hours of the onset of the symptoms. In some embodiments, the initial administration of the ACK inhibitor compound (e.g., an ITK or BTK inhibitor, such as for example ibrutinib) is via any route practical, such as, for example, an intravenous injection, a bolus injection, infusion over 5 minutes to about 5 hours, a pill, a capsule, a tablet, a transdermal patch, buccal delivery, and the like, or combination thereof. The ACK inhibitor compound (e.g., an ITK or BTK inhibitor, such as for example ibrutinib) should be administered as soon as is practicable after the onset of a disorder is detected or suspected, and for a length of time necessary for the treatment of the disease, such as, for example, from about 1 month to about 3 months. The length of treatment can vary for each subject, and the length can be determined using the known criteria. In some embodiments, the ACK inhibitor compound (e.g., an ITK or BTK inhibitor, such as for example ibrutinib) is administered for at least 2 weeks, between about 1 month to about 5 years, or from about 1 month to about 3 years.

Therapeutically effective amounts will depend on the severity and course of the disorder, previous therapy, the patient's health status, weight, and response to the drugs, and the judgment of the treating physician. Prophylactically effective amounts depend on the patient's state of health, weight, the severity and course of the disease, previous therapy, response to the drugs, and the judgment of the treating physician.

In some embodiments, the ACK inhibitor compound (e.g., an ITK or BTK inhibitor, such as for example ibrutinib) is administered to the patient on a regular basis, e.g., three times a day, two times a day, once a day, every other day or every 3 days. In other embodiments, the ACK inhibitor compound (e.g., an ITK or BTK inhibitor, such as for example ibrutinib) is administered to the patient on an intermittent basis, e.g., twice a day followed by once a day followed by three times a day; or the first two days of every week; or the first, second and third day of a week. In some embodiments, intermittent dosing is as effective as regular dosing. In further or alternative embodiments, the ACK inhibitor compound (e.g., an ITK or BTK inhibitor, such as for example ibrutinib) is administered only when the patient exhibits a particular symptom, e.g., the onset of pain, or the onset of a fever, or the onset of an inflammation, or the onset of a skin disorder. Dosing schedules of each compound may depend on the other or may be independent of the other.

In the case wherein the patient's condition does not improve, upon the doctor's discretion the compounds may be administered chronically, that is, for an extended period of time, including throughout the duration of the patient's life in order to ameliorate or otherwise control or limit the symptoms of the patient's disorder.

In the case wherein the patient's status does improve, upon the doctor's discretion the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance regimen is administered if necessary. Subsequently, the dosage or the frequency of administration, or both, of the ACK inhibitor compound (e.g., an ITK or BTK inhibitor, such as for example ibrutinib) can be reduced, as a function of the symptoms, to a level at which the individual's improved condition is retained. Individuals can, however, require intermittent treatment on a long-term basis upon any recurrence of symptoms.

The amount of the ACK inhibitor compound (e.g., an ITK or BTK inhibitor, such as for example ibrutinib) will vary depending upon factors such as the particular compound, disorder and its severity, the identity (e.g., weight) of the subject or host in need of treatment, and is determined according to the particular circumstances surrounding the case, including, e.g., the specific agents being administered, the routes of administration, and the subject or host being treated. In general, however, doses employed for adult human treatment will typically be in the range of 0.02-5000 mg per day, or from about 1-1500 mg per day. The desired dose may be presented in a single dose or as divided doses administered simultaneously (or over a short period of time) or at appropriate intervals, for example as two, three, four or more sub-doses per day.

In some embodiments, the therapeutic amount of the ACK inhibitor (e.g., an ITK or BTK inhibitor, such as for example ibrutinib) is from 100 mg/day up to, and including, 2000 mg/day. In some embodiments, the amount of the ACK inhibitor (e.g., an ITK or BTK inhibitor, such as for example ibrutinib) is from 140 mg/day up to, and including, 840 mg/day. In some embodiments, the amount of the ACK inhibitor (e.g., an ITK or BTK inhibitor, such as for example ibrutinib) is from 420 mg/day up to, and including, 840 mg/day. In some embodiments, the amount of the ACK inhibitor (e.g., an ITK or BTK inhibitor, such as for example ibrutinib) is about 40 mg/day. In some embodiments, the amount of the ACK inhibitor (e.g., an ITK or BTK inhibitor, such as for example ibrutinib) is about 140 mg/day. In some embodiments, the amount of the ACK inhibitor (e.g., an ITK or BTK inhibitor, such as for example ibrutinib) is about 280 mg/day. In some embodiments, the amount of the ACK inhibitor (e.g., an ITK or BTK inhibitor, such as for example ibrutinib) is about 420 mg/day. In some embodiments, the amount of the ACK inhibitor (e.g., an ITK or BTK inhibitor, such as for example ibrutinib) is about 560 mg/day. In some embodiments, the amount of the ACK inhibitor (e.g., an ITK or BTK inhibitor, such as for example ibrutinib) is about 700 mg/day. In some embodiments, the amount of the ACK inhibitor (e.g., an ITK or BTK inhibitor, such as for example ibrutinib) is about 840 mg/day. In some embodiments, the amount of the ACK inhibitor (e.g., an ITK or BTK inhibitor, such as for example ibrutinib) is about 980 mg/day. In some embodiments, the amount of the ACK inhibitor (e.g., an ITK or BTK inhibitor, such as for example ibrutinib) is about 1120 mg/day. In some embodiments, the amount of the ACK inhibitor (e.g., an ITK or BTK inhibitor, such as for example ibrutinib) is about 1260 mg/day. In some embodiments, the amount of the ACK inhibitor (e.g., an ITK or BTK inhibitor, such as for example ibrutinib) is about 1400 mg/day. In some embodiments, a compound of Formula (A) is administered at a dosage of between about 0.1 mg/kg per day to about 100 mg/kg per day.

In some embodiments, the dosage of the ACK inhibitor (e.g., an ITK or BTK inhibitor, such as for example ibrutinib) is escalated over time. In some embodiments, the dosage of the ACK inhibitor (e.g., an ITK or BTK inhibitor, such as for example ibrutinib) is escalated, for example, from at or about 1.25 mg/kg/day to at or about 12.5 mg/kg/day over a predetermined period of time. In some embodiments the predetermined period of time is over 1 month, over 2 months, over 3 months, over 4 months, over 5 months, over 6 months, over 7 months, over 8 months, over 9 months, over 10 months, over 11 months, over 12 months, over 18 months, over 24 months or longer.

The ACK inhibitor compound (e.g., an ITK or BTK inhibitor, such as for example ibrutinib) may be formulated into unit dosage forms suitable for single administration of precise dosages. In unit dosage form, the formulation is divided into unit doses containing appropriate quantities of one or both compounds. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

It is understood that a medical professional will determine the dosage regimen in accordance with a variety of factors. These factors include the severity of GVHD in the subject, as well as the age, weight, sex, diet, and medical condition of the subject.

Compounds

Described herein are methods of preventing the occurrence of graft versus host disease (GVHD) or reducing the severity of GVHD occurrence in a patient requiring cell transplantation comprising administering to the patient a composition comprising a therapeutically-effective amount of an ACK inhibitor compound (e.g., an ITK or BTK inhibitor, such as for example ibrutinib).

Further described herein are methods of treating a patient for alleviation of a bone marrow mediated disease, with alleviation of consequently developed graft versus host disease (GVHD), comprising administering to the patient allogeneic hematopoietic stem cells and/or allogeneic T-cells, wherein a therapeutically effective amount of an ACK inhibitor compound (e.g., an ITK or BTK inhibitor, such as for example ibrutinib) is administered prior to or concurrently with the allogeneic hematopoietic stem cells and/or allogeneic T-cells.

In the following description of irreversible BTK compounds suitable for use in the methods described herein, definitions of referred-to standard chemistry terms may be found in reference works (if not otherwise defined herein), including Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the ordinary skill of the art are employed. In addition, nucleic acid and amino acid sequences for BTK (e.g., human BTK) are known in the art as disclosed in, e.g., U.S. Pat. No. 6,326,469. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients.

The BTK inhibitor compounds described herein are selective for BTK and kinases having a cysteine residue in an amino acid sequence position of the tyrosine kinase that is homologous to the amino acid sequence position of cysteine 481 in BTK. Generally, an irreversible inhibitor compound of BTK used in the methods described herein is identified or characterized in an in vitro assay, e.g., an acellular biochemical assay or a cellular functional assay. Such assays are useful to determine an in vitro $IC_{50}$ for an irreversible BTK inhibitor compound.

For example, an acellular kinase assay can be used to determine BTK activity after incubation of the kinase in the absence or presence of a range of concentrations of a candidate irreversible BTK inhibitor compound. If the candidate compound is in fact an irreversible BTK inhibitor, BTK kinase activity will not be recovered by repeat washing with inhibitor-free medium. See, e.g., J. B. Smaill, et al. (1999), *J. Med. Chem.* 42(10):1803-1815. Further, covalent complex formation between BTK and a candidate irreversible BTK inhibitor is a useful indicator of irreversible inhibition of BTK that can be readily determined by a number of methods known in the art (e.g., mass spectrometry). For example, some irreversible BTK-inhibitor compounds can form a covalent bond with Cys 481 of BTK (e.g., via a Michael reaction).

Cellular functional assays for BTK inhibition include measuring one or more cellular endpoints in response to stimulating a BTK-mediated pathway in a cell line (e.g., BCR activation in Ramos cells) in the absence or presence of a range of concentrations of a candidate irreversible BTK inhibitor compound. Useful endpoints for determining a response to BCR activation include, e.g., autophosphorylation of BTK, phosphorylation of a BTK target protein (e.g., PLC-γ), and cytoplasmic calcium flux.

High-throughput assays for many acellular biochemical assays (e.g., kinase assays) and cellular functional assays (e.g., calcium flux) are well known to those of ordinary skill in the art. In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. Automated systems thereby allow the identification and characterization of a large number of irreversible BTK compounds without undue effort.

In some embodiments, the BTK inhibitor is selected from the group consisting of a small organic molecule, a macromolecule, a peptide or a non-peptide.

In some embodiments, the BTK inhibitor provided herein is a reversible or irreversible inhibitor. In certain embodiments, the BTK inhibitor is an irreversible inhibitor.

In some embodiments, the irreversible BTK inhibitor forms a covalent bond with a cysteine sidechain of a Bruton's tyrosine kinase, a Bruton's tyrosine kinase homolog, or a BTK tyrosine kinase cysteine homolog.

Irreversible BTK inhibitor compounds can be used for the manufacture of a medicament for treating any of the foregoing conditions (e.g., autoimmune diseases, inflammatory diseases, allergy disorders, B-cell proliferative disorders, or thromboembolic disorders).

In some embodiments, the irreversible BTK inhibitor compound used for the methods described herein inhibits BTK or a BTK homolog kinase activity with an in vitro $IC_{50}$ of less than 10 μM (e.g., less than 1 μM, less than 0.5 μM, less than 0.4 μM, less than 0.3 μM, less than 0.1, less than 0.08 μM, less than 0.06 μM, less than 0.05 μM, less than 0.04 μM, less than 0.03 μM, less than less than 0.02 μM, less than 0.01, less than 0.008 μM, less than 0.006 μM, less than 0.005 μM, less than 0.004 μM, less than 0.003 μM, less than less than 0.002 μM, less than 0.001, less than 0.00099 μM, less than 0.00098 μM, less than 0.00097 μM, less than 0.00096 μM, less than 0.00095 μM, less than 0.00094 μM, less than 0.00093 μM, less than 0.00092, or less than 0.00090 μM).

In some embodiments, the irreversible BTK inhibitor compound is selected from among ibrutinib (PCI-32765), PCI-45292, PCI-45466, AVL-101, AVL-291, AVL-292, or ONO-WG-37. In some embodiments, the irreversible BTK inhibitor compound is ibrutinib.

In one embodiment, the irreversible BTK inhibitor compound selectively and irreversibly inhibits an activated form of its target tyrosine kinase (e.g., a phosphorylated form of the tyrosine kinase). For example, activated BTK is transphosphorylated at tyrosine 551. Thus, in these embodiments the irreversible BTK inhibitor inhibits the target kinase in cells only once the target kinase is activated by the signaling events.

In other embodiments, the BTK inhibitor used in the methods describe herein has the structure of any of Formula (A). Also described herein are pharmaceutically acceptable salts, pharmaceutically acceptable solvates, pharmaceutically active metabolites, and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided.

Definition of standard chemistry terms are found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques are optionally used for chemical syntheses, chemical analyses, pharmaceutical preparation, formulation, and delivery, and treatment of patients. Standard techniques are optionally used for recombinant DNA, oligonucleotide synthesis, and tissue culture and transformation (e.g., electroporation, lipofection). Reactions and purification techniques are performed using documented methodologies or as described herein.

It is to be understood that the methods and compositions described herein are not limited to the particular methodology, protocols, cell lines, constructs, and reagents described herein and as such optionally vary. It is also to be understood that the terminology used herein is for the purpose of describing particular embodiments only, and is not intended to limit the scope of the methods and compositions described herein, which will be limited only by the appended claims.

Unless stated otherwise, the terms used for complex moieties (i.e., multiple chains of moieties) are to be read equivalently either from left to right or right to left. For example, the group alkylenecycloalkylene refers both to an alkylene group followed by a cycloalkylene group or as a cycloalkylene group followed by an alkylene group.

The suffix "ene" appended to a group indicates that such a group is a diradical. By way of example only, a methylene is a diradical of a methyl group, that is, it is a —CH$_2$— group; and an ethylene is a diradical of an ethyl group, i.e., —CH$_2$CH$_2$—.

An "alkyl" group refers to an aliphatic hydrocarbon group. The alkyl moiety includes a "saturated alkyl" group, which means that it does not contain any alkene or alkyne moieties. The alkyl moiety also includes an "unsaturated alkyl" moiety, which means that it contains at least one alkene or alkyne moiety. An "alkene" moiety refers to a group that has at least one carbon-carbon double bond, and an "alkyne" moiety refers to a group that has at least one carbon-carbon triple bond. The alkyl moiety, whether saturated or unsaturated, includes branched, straight chain, or cyclic moieties. Depending on the structure, an alkyl group includes a monoradical or a diradical (i.e., an alkylene group), and if a "lower alkyl" having 1 to 6 carbon atoms.

As used herein, C$_1$-C$_x$ includes C$_1$-C$_2$, C$_1$-C$_3$ . . . C$_1$-C$_x$.

The "alkyl" moiety optionally has 1 to 10 carbon atoms (whenever it appears herein, a numerical range such as "1 to 10" refers to each integer in the given range; e.g., "1 to 10 carbon atoms" means that the alkyl group is selected from a moiety having 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein may be designated as "C$_1$-C$_4$ alkyl" or similar designations. By way of example only, "C$_1$-C$_4$ alkyl" indicates that there are one to four carbon atoms in the alkyl chain, i.e., the alkyl chain is selected from among methyl, ethyl, propyl, iso-propyl, n-butyl, iso-butyl, sec-butyl, and t-butyl. Thus C$_1$-C$_4$ alkyl includes C$_1$-C$_2$ alkyl and C$_1$-C$_3$ alkyl. Alkyl groups are optionally substituted or unsubstituted. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

The term "alkenyl" refers to a type of alkyl group in which the first two atoms of the alkyl group form a double bond that is not part of an aromatic group. That is, an alkenyl group begins with the atoms —C(R)=C(R)—R, wherein R refers to the remaining portions of the alkenyl group, which are either the same or different. The alkenyl moiety is optionally branched, straight chain, or cyclic (in which case, it is also known as a "cycloalkenyl" group). Depending on the structure, an alkenyl group includes a monoradical or a diradical (i.e., an alkenylene group). Alkenyl groups are optionally substituted. Non-limiting examples of an alkenyl group include —CH=CH$_2$, —C(CH$_3$)=CH$_2$, —CH=CHCH$_3$, —C(CH$_3$)=CHCH$_3$. Alkenylene groups include, but are not limited to, —CH=CH—, —C(CH$_3$)=CH—, —CH=CHCH$_2$—, —CH=CHCH$_2$CH$_2$— and —C(CH$_3$)=CHCH$_2$—. Alkenyl groups optionally have 2 to 10 carbons, and if a "lower alkenyl" having 2 to 6 carbon atoms.

The term "alkynyl" refers to a type of alkyl group in which the first two atoms of the alkyl group form a triple bond. That is, an alkynyl group begins with the atoms —C≡C—R, wherein R refers to the remaining portions of the alkynyl group, which is either the same or different. The "R" portion of the alkynyl moiety may be branched, straight chain, or cyclic. Depending on the structure, an alkynyl group includes a monoradical or a diradical (i.e., an alkynylene group). Alkynyl groups are optionally substituted. Non-limiting examples of an alkynyl group include, but are not limited to, —C≡CH, —C≡CCH$_3$, —C≡CCH$_2$CH$_3$, —C≡C—, and —C≡CCH$_2$—. Alkynyl groups optionally have 2 to 10 carbons, and if a "lower alkynyl" having 2 to 6 carbon atoms.

An "alkoxy" group refers to a (alkyl)O— group, where alkyl is as defined herein.

"Hydroxyalkyl" refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl.

"Alkoxyalkyl" refers to an alkyl radical, as defined herein, substituted with an alkoxy group, as defined herein.

The term "alkylamine" refers to the —N(alkyl)$_x$H$_y$ group, where x and y are selected from among x=1, y=1 and x=2, y=0. When x=2, the alkyl groups, taken together with the N atom to which they are attached, optionally form a cyclic ring system.

"Alkylaminoalkyl" refers to an alkyl radical, as defined herein, substituted with an alkylamine, as defined herein.

"Hydroxyalkylaminoalkyl" refers to an alkyl radical, as defined herein, substituted with an alkylamine, and alkyl-hydroxy, as defined herein.

"Alkoxyalkylaminoalkyl" refers to an alkyl radical, as defined herein, substituted with an alkylamine and substituted with an alkylalkoxy, as defined herein.

An "amide" is a chemical moiety with the formula —C(O)NHR or —NHC(O)R, where R is selected from among alkyl, cycloalkyl, aryl, heteroaryl (bonded through a ring carbon) and heteroalicyclic (bonded through a ring carbon). In some embodiments, an amide moiety forms a linkage between an amino acid or a peptide molecule and a compound described herein, thereby forming a prodrug. Any amine, or carboxyl side chain on the compounds described herein can be amidified. The procedures and specific groups to make such amides are found in sources such as Greene and Wuts, Protective Groups in Organic Synthesis, 3$^{rd}$ Ed., John Wiley & Sons, New York, N.Y., 1999, which is incorporated herein by reference for this disclosure.

The term "ester" refers to a chemical moiety with formula —COOR, where R is selected from among alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are found in sources such as Greene and Wuts, Protective Groups in Organic Synthesis, 3$^{rd}$ Ed., John Wiley & Sons, New York, N.Y., 1999, which is incorporated herein by reference for this disclosure.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "fused" refers to structures in which two or more rings share one or more bonds.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e. a heteroatom). Heterocycle includes heteroaryl and heterocycloalkyl. Carbocycles and heterocycles can be optionally substituted.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

An "aryloxy" group refers to an (aryl)O— group, where aryl is as defined herein.

The term "carbonyl" as used herein refers to a group containing a moiety selected from the group consisting of —C(O)—, —S(O)—, —S(O)$_2$—, and —C(S)—, including, but not limited to, groups containing a least one ketone group, and/or at least one aldehyde group, and/or at least one ester group, and/or at least one carboxylic acid group, and/or at least one thioester group. Such carbonyl groups include ketones, aldehydes, carboxylic acids, esters, and thioesters. In some embodiments, such groups are a part of linear, branched, or cyclic molecules.

The term "cycloalkyl" refers to a monocyclic or polycyclic radical that contains only carbon and hydrogen, and is optionally saturated, partially unsaturated, or fully unsaturated. Cycloalkyl groups include groups having from 3 to 10 ring atoms. Illustrative examples of cycloalkyl groups include the following moieties:

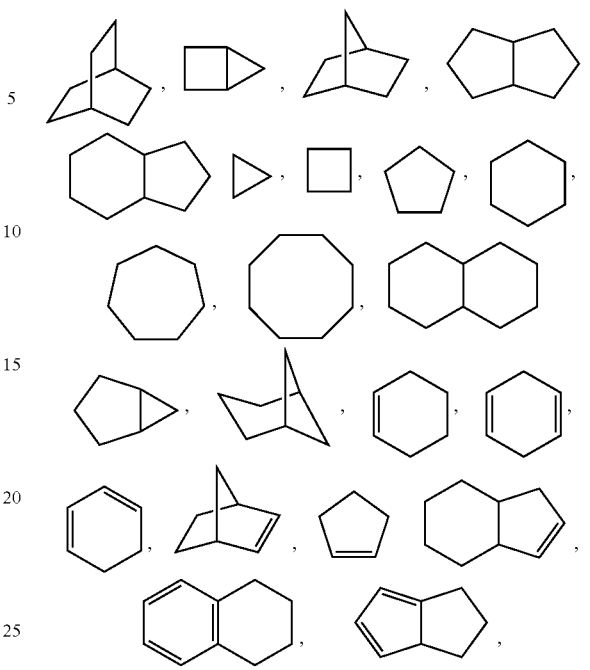

and the like. Depending on the structure, a cycloalkyl group is either a monoradical or a diradical (e.g., an cycloalkylene group), and if a "lower cycloalkyl" having 3 to 8 carbon atoms.

"Cycloalkylalkyl" means an alkyl radical, as defined herein, substituted with a cycloalkyl group. Non-limiting cycloalkylalkyl groups include cyclopropylmethyl, cyclobutylmethyl, cyclopentylmethyl, cyclohexylmethyl, and the like.

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocylic ring can have additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In heterocycles that have two or more heteroatoms, those two or more heteroatoms can be the same or different from one another. Heterocycles can be optionally substituted. Binding to a heterocycle can be at a heteroatom or via a carbon atom. Non-aromatic heterocyclic groups include groups having only 4 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, are optionally C-attached or N-attached where such is possible. For instance, a group derived from pyrrole includes pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group).

The terms "heteroaryl" or, alternatively, "heteroaromatic" refers to an aromatic group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Illustrative examples of heteroaryl groups include the following moieties:

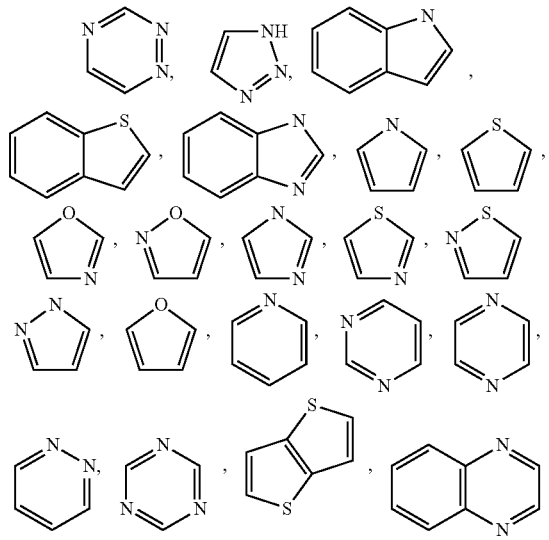

and the like. Depending on the structure, a heteroaryl group can be a monoradical or a diradical (i.e., a heteroarylene group).

As used herein, the term "non-aromatic heterocycle", "heterocycloalkyl" or "heteroalicyclic" refers to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. In some embodiments, the radicals are fused with an aryl or heteroaryl. Heterocycloalkyl rings can be formed by three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

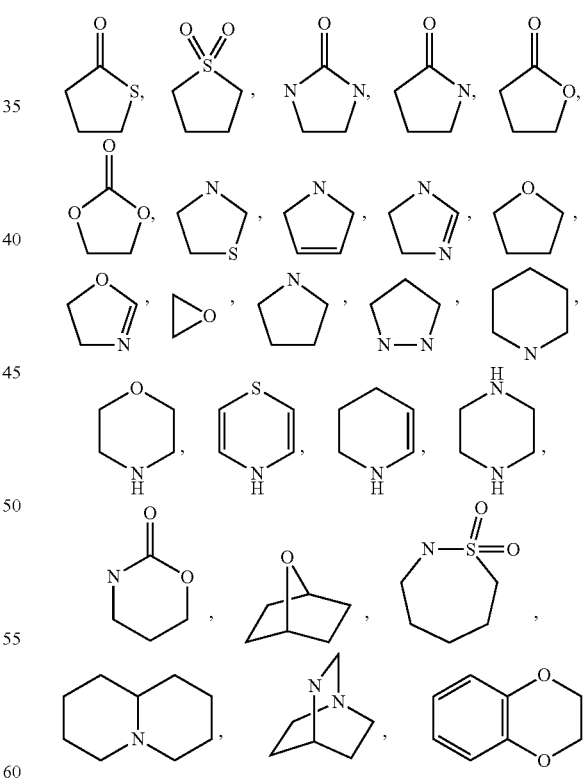

and the like. The term heteroalicyclic also includes all ring forms of the carbohydrates, including but not limited to the monosaccharides, the disaccharides and the oligosaccharides. Depending on the structure, a heterocycloalkyl group can be a monoradical or a diradical (i.e., a heterocycloalkylene group).

The term "halo" or, alternatively, "halogen" or "halide" means fluoro, chloro, bromo, and iodo.

The term "haloalkyl," refers to alkyl structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another.

The term "fluoroalkyl," as used herein, refers to alkyl group in which at least one hydrogen is replaced with a fluorine atom. Examples of fluoroalkyl groups include, but are not limited to, —$CF_3$, —$CH_2CF_3$, —$CF_2CF_3$, —$CH_2CH_2CF_3$ and the like.

As used herein, the term "heteroalkyl" refers to optionally substituted alkyl radicals in which one or more skeletal chain atoms is a heteroatom, e.g., oxygen, nitrogen, sulfur, silicon, phosphorus or combinations thereof. The heteroatom(s) are placed at any interior position of the heteroalkyl group or at the position at which the heteroalkyl group is attached to the remainder of the molecule. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. In addition, in some embodiments, up to two heteroatoms are consecutive, such as, by way of example, —$CH_2$—NH—$OCH_3$ and —$CH_2$—O—Si($CH_3$)$_3$.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

A "thioalkoxy" or "alkylthio" group refers to a —S-alkyl group.

A "SH" group is also referred to either as a thiol group or a sulfhydryl group.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, acyl, nitro, haloalkyl, fluoroalkyl, amino, including mono- and di-substituted amino groups, and the protected derivatives thereof. By way of example an optional substituents may be $L_sR_s$, wherein each $L_s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, -(substituted or unsubstituted $C_1$-$C_6$ alkyl), or -(substituted or unsubstituted $C_2$-$C_6$ alkenyl); and each $R_s$ is independently selected from H, (substituted or unsubstituted $C_1$-$C_4$ alkyl), (substituted or unsubstituted $C_3$-$C_6$ cycloalkyl), heteroaryl, or heteroalkyl. The protecting groups that form the protective derivatives of the above substituents include those found in sources such as Greene and Wuts, above.

ACK Inhibitor Compounds

Described herein are methods of preventing the occurrence of graft versus host disease (GVHD) or reducing the severity of GVHD occurrence in a patient requiring cell transplantation comprising administering to the patient a composition comprising a therapeutically-effective amount of an ACK inhibitor compound (e.g., an ITK or BTK inhibitor, such as, for example, ibrutinib).

Further described herein are methods of treating a patient for alleviation of a bone marrow mediated disease, with alleviation of consequently developed graft versus host disease (GVHD), comprising administering to the patient allogeneic hematopoietic stem cells and/or allogeneic T-cells, wherein a therapeutically effective amount of an ACK inhibitor compound (e.g., an ITK or BTK inhibitor, such as, for example, ibrutinib) is administered prior to or concurrently with the allogeneic hematopoietic stem cells and/or allogeneic T-cells.

The ACK inhibitor compounds described herein are selective for kinases having an accessible cysteine that is able to form a covalent bond with a Michael acceptor moiety on the inhibitor compound. In some embodiments, the cysteine residue is accessible or becomes accessible when the binding site moiety of the irreversible inhibitor binds to the kinase. That is, the binding site moiety of the irreversible inhibitor binds to an active site of the ACK and the Michael acceptor moiety of irreversible inhibitor gains access (in one embodiment the step of binding leads to a conformational change in the ACK, thus exposing the cysteine) or is otherwise exposed to the cysteine residue of the ACK; as a result a covalent bond is formed between the "S" of the cysteine residue and the Michael acceptor of the irreversible inhibitor. Consequently, the binding site moiety of the irreversible inhibitor remains bound or otherwise blocks the active site of the ACK.

In some embodiments, the ACK is BTK, a homolog of BTK or a tyrosine kinase having a cysteine residue in an amino acid sequence position that is homologous to the amino acid sequence position of cysteine 481 in BTK. In some embodiments, the ACK is ITK. In some embodiments, the ACK is HER4. Inhibitor compounds described herein include a Michael acceptor moiety, a binding site moiety and a linker that links the binding site moiety and the Michael acceptor moiety (and in some embodiments, the structure of the linker provides a conformation, or otherwise directs the Michael acceptor moiety, so as to improve the selectivity of the irreversible inhibitor for a particular ACK). In some embodiments, the ACK inhibitor inhibits ITK and BTK.

In some embodiments, the ACK inhibitor is a compound of Formula (A):

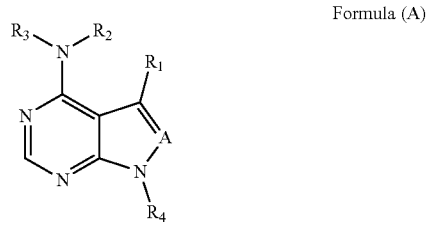

Formula (A)

wherein

A is independently selected from N or $CR_5$;

$R_1$ is H, $L_2$-(substituted or unsubstituted alkyl), $L_2$-(substituted or unsubstituted cycloalkyl), $L_2$-(substituted or unsubstituted alkenyl), $L_2$-(substituted or unsubstituted cycloalkenyl), $L_2$-(substituted or unsubstituted heterocycle), $L_2$-(substituted or unsubstituted heteroaryl), or $L_2$-(substituted or unsubstituted aryl), where $L_2$ is a bond, O, S, —S(=O), —S(=O)$_2$, C(=O), -(substituted or unsubstituted $C_1$-$C_6$ alkyl), or -(substituted or unsubstituted $C_2$-$C_6$ alkenyl);

$R_2$ and $R_3$ are independently selected from H, lower alkyl and substituted lower alkyl;

$R_4$ is $L_3$-X-$L_4$-G, wherein, $L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;

X is optional, and when present is a bond, O, —C(=O), S, —S(=O), —S(=O)$_2$, —NH, —NR$_9$, —NHC(O), —C(O)NH, —NR$_9$C(O), —C(O)NR$_9$, —S(=O)$_2$NH, —NHS(=O)$_2$, —S(=O)$_2$NR$_9$—, —NR$_9$S(=O)$_2$, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl, aryl, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)—;

$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;

or $L_3$, X and $L_4$ taken together form a nitrogen containing heterocyclic ring;

G is

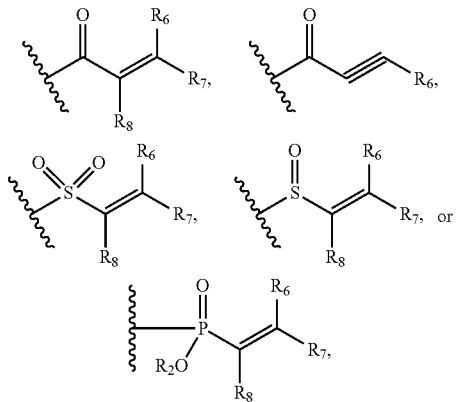

wherein, $R_6$, $R_7$ and $R_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl;

$R_5$ is H, halogen, -$L_6$-(substituted or unsubstituted $C_1$-$C_3$ alkyl), -$L_6$-(substituted or unsubstituted $C_2$-$C_4$ alkenyl), -$L_6$-(substituted or unsubstituted heteroaryl), or -$L_6$-(substituted or unsubstituted aryl), wherein $L_6$ is a bond, O, S, —S(=O), S(=O)$_2$, NH, C(O), —NHC(O)O, —OC(O)NH, —NHC(O), or —C(O)NH;

each $R_9$ is independently selected from among H, substituted or unsubstituted lower alkyl, and substituted or unsubstituted lower cycloalkyl;

each $R_{10}$ is independently H, substituted or unsubstituted lower alkyl, or substituted or unsubstituted lower cycloalkyl; or two $R_{10}$ groups can together form a 5-, 6-, 7-, or 8-membered heterocyclic ring; or $R_{10}$ and $R_{11}$ can together form a 5-, 6-, 7-, or 8-membered heterocyclic ring; or each $R_{11}$ is independently selected from H or alkyl; and pharmaceutically active metabolites, pharmaceutically acceptable solvates, pharmaceutically acceptable salts, or pharmaceutically acceptable prodrugs thereof.

In some embodiments, the compound of Formula (A) is a BTK inhibitor. In some embodiments, the compound of Formula (A) is an ITK inhibitor. In some embodiments, the compound of Formula (A) inhibits ITK and BTK.

In some embodiments, the compound of Formula (A) has the structure:

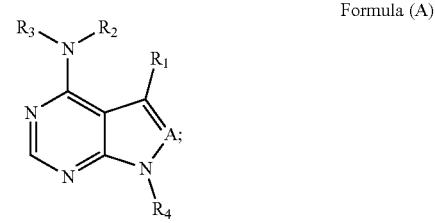

Formula (A)

wherein:

A is N;

$R_2$ and $R_3$ are each H;

$R_1$ is phenyl-O-phenyl or phenyl-S-phenyl; and $R_4$ is $L_3$-X-$L_4$-G, wherein, $L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;

X is optional, and when present is a bond, O, —C(=O), S, —S(=O), —S(=O)$_2$, —NH, —NR$_9$, —NHC(O), —C(O)NH, —NR$_9$C(O), —C(O)NR$_9$, —S(=O)$_2$NH, —NHS(=O)$_2$, —S(=O)$_2$NR$_9$—, —NR$_9$S(=O)$_2$, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl, aryl, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;

$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;

or L₃, X and L₄ taken together form a nitrogen containing heterocyclic ring;

G is

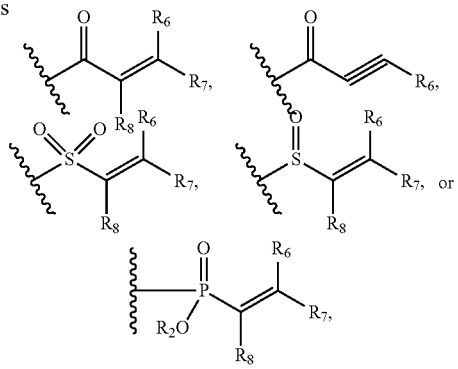

wherein,

R₆, R₇ and R₈ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl.

In some embodiments, the ACK inhibitor is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib)

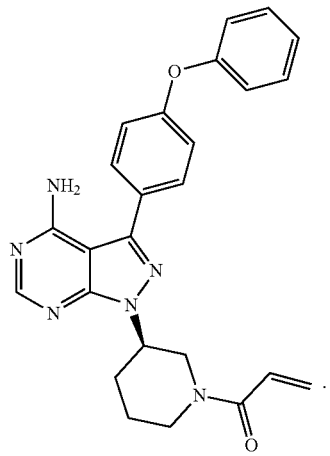

Ibrutinib

In some embodiments, the ACK inhibitor is AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), or HM71224 (Hanmi Pharmaceutical Company Limited).

In some embodiments, the ACK inhibitor is 4-(tert-butyl)-N-(2-methyl-3-(4-methyl-6-((4-(morpholine-4-carbonyl) phenyl)amino)-5-oxo-4,5-dihydropyrazin-2-yl)phenyl)benzamide (CGI-1746); 7-benzyl-1-(3-(piperidin-1-yl)propyl)-2-(4-(pyridin-4-yl)phenyl)-1H-imidazo[4,5-g]quinoxalin-6 (5H)-one (CTA-056); (R)—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide (GDC-0834); 6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one (RN-486); N-[5-[5-(4-acetylpiperazine-1-carbonyl)-4-methoxy-2-methylphenyl]sulfanyl-1,3-thiazol-2-yl]-4-[(3, 3-dimethylbutan-2-ylamino)methyl]benzamide (BMS-509744, HY-11092); or N-(5-((5-(4-Acetylpiperazine-1-carbonyl)-4-methoxy-2-methylphenyl)thio)thiazol-2-yl)-4-(((3-methylbutan-2-yl)amino)methyl)benzamide (HY11066).

In some embodiments, the ACK inhibitor is:

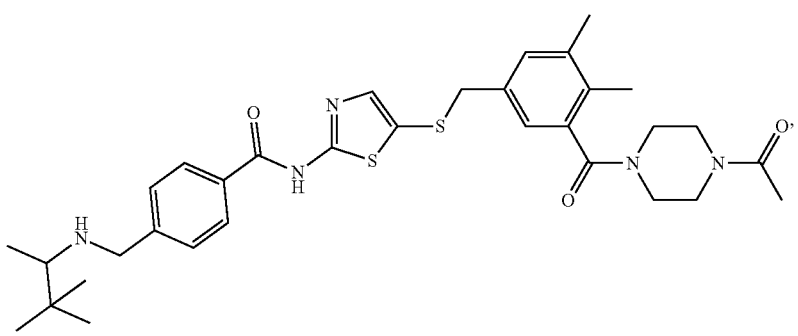

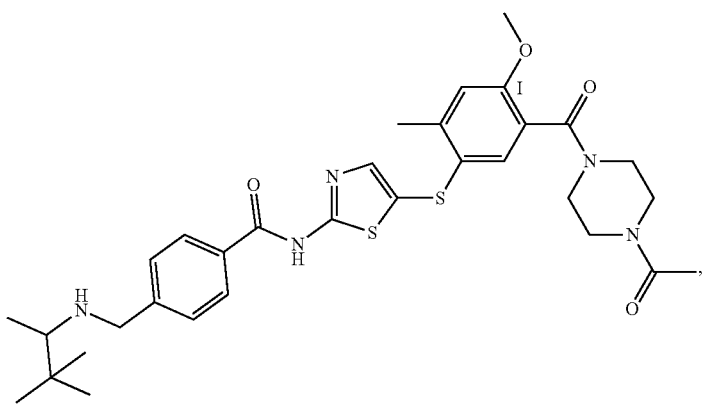
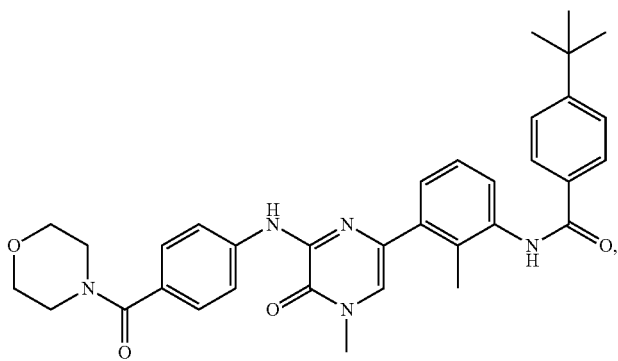
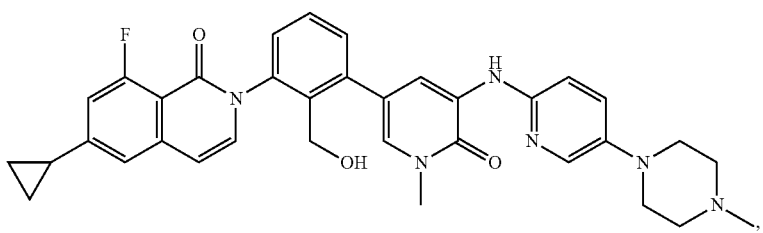
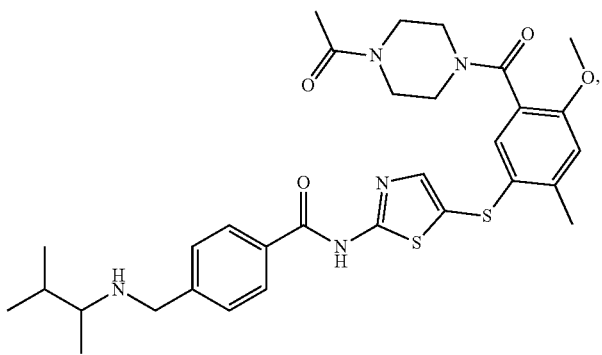

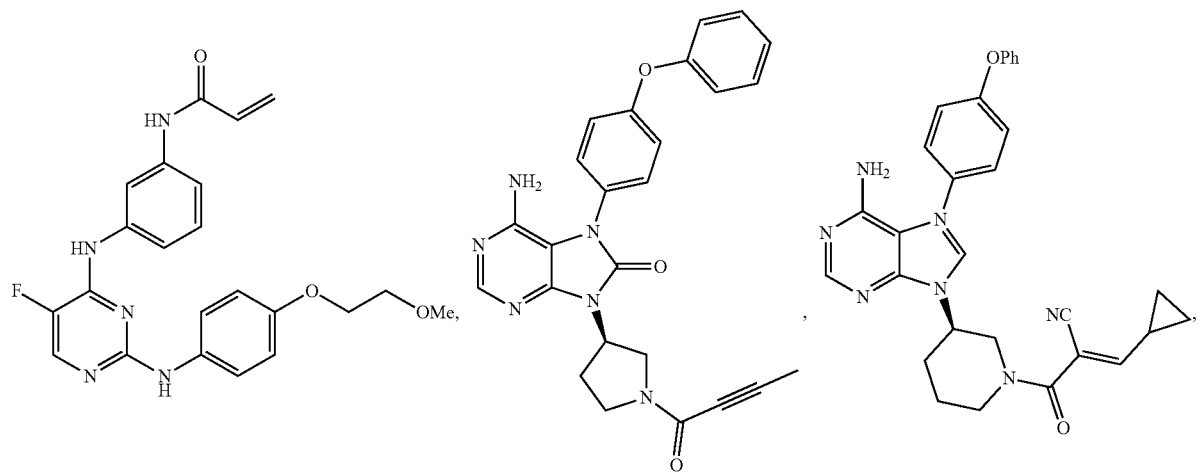
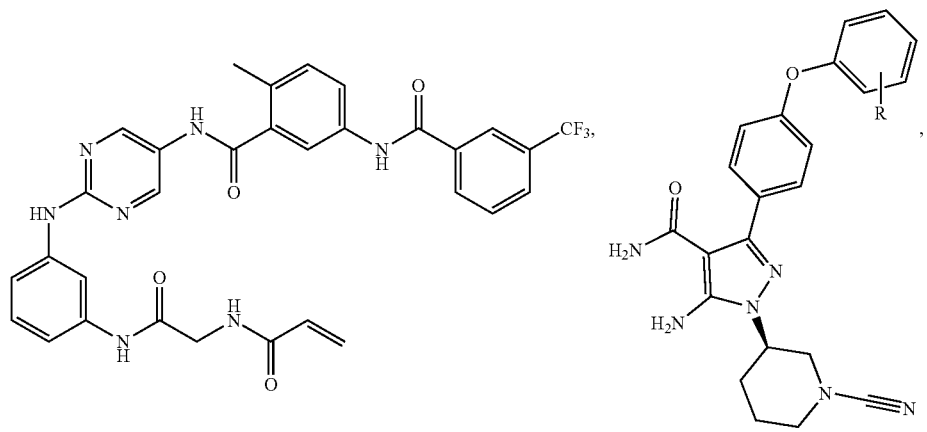
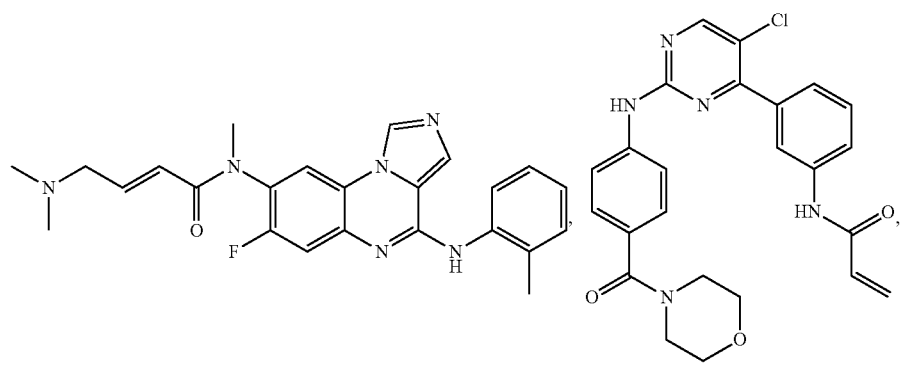

-continued
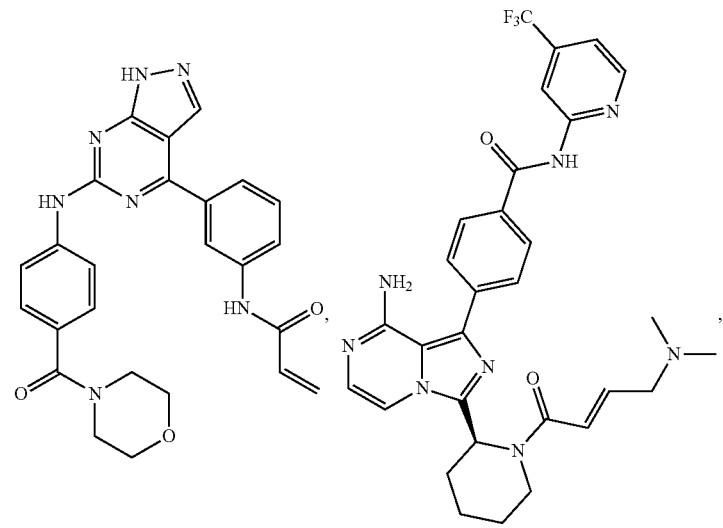
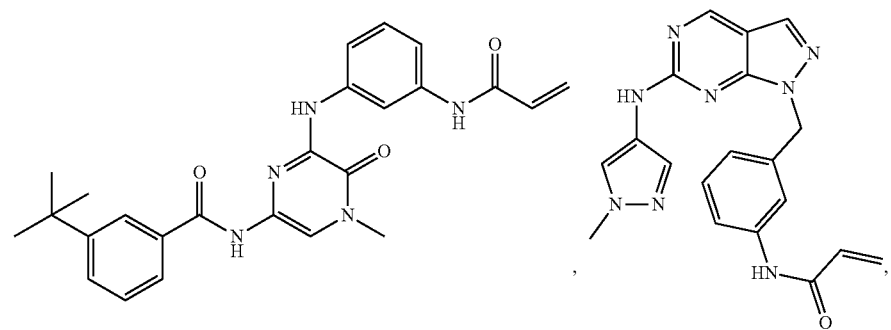

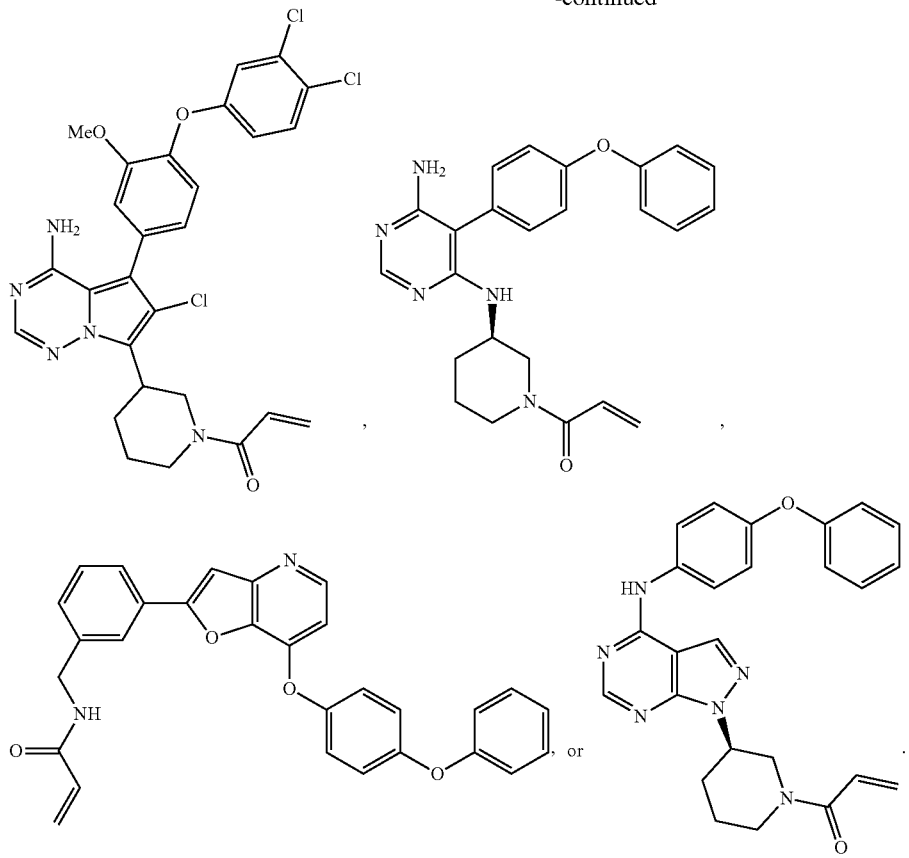

In some embodiments, ACK inhibitor is an ITK inhibitor. In some embodiments, the ITK inhibitor is an ITK inhibitor compound described in WO2002/0500071, which is incorporated by reference in its entirety. In some embodiments, the ITK inhibitor is an ITK inhibitor compound described in WO2005/070420, which is incorporated by reference in its entirety. In some embodiments, the ITK inhibitor is an ITK inhibitor compound described in WO2005/079791, which is incorporated by reference in its entirety. In some embodiments, the ITK inhibitor is an ITK inhibitor compound described in WO2007/076228, which is incorporated by reference in its entirety. In some embodiments, the ITK inhibitor is an ITK inhibitor compound described in WO2007/058832, which is incorporated by reference in its entirety. In some embodiments, the ITK inhibitor is an ITK inhibitor compound described in WO2004/016610, which is incorporated by reference in its entirety. In some embodiments, the ITK inhibitor is an ITK inhibitor compound described in WO2004/016611, which is incorporated by reference in its entirety. In some embodiments, the ITK inhibitor is an ITK inhibitor compound described in WO2004/016600, which is incorporated by reference in its entirety. In some embodiments, the ITK inhibitor is an ITK inhibitor compound described in WO2004/016615, which is incorporated by reference in its entirety. In some embodiments, the ITK inhibitor is an ITK inhibitor compound described in WO2005/026175, which is incorporated by reference in its entirety. In some embodiments, the ITK inhibitor is an ITK inhibitor compound described in WO2006/065946, which is incorporated by reference in its entirety. In some embodiments, the ITK inhibitor is an ITK inhibitor compound described in WO2007/027594, which is incorporated by reference in its entirety. In some embodiments, the ITK inhibitor is an ITK inhibitor compound described in WO2007/017455, which is incorporated by reference in its entirety. In some embodiments, the ITK inhibitor is an ITK inhibitor compound described in WO2008/025820, which is incorporated by reference in its entirety. In some embodiments, the ITK inhibitor is an ITK inhibitor compound described in WO2008/025821, which is incorporated by reference in its entirety. In some embodiments, the ITK inhibitor is an ITK inhibitor compound described in WO2008/025822, which is incorporated by reference in its entirety. In some embodiments, the ITK inhibitor is an ITK inhibitor compound described in WO2011/017219, which is incorporated by reference in its entirety. In some embodiments, the ITK inhibitor is an ITK inhibitor compound described in WO2011/090760, which is incorporated by reference in its entirety. In some embodiments, the ITK inhibitor is an ITK inhibitor compound described in WO2009/158571, which is incorporated by reference in its entirety. In some embodiments, the ITK inhibitor is an ITK inhibitor compound described in WO2009/051822, which is incorporated by reference in its entirety. In some embodiments, the ITK inhibitor is an ITK inhibitor compound described in U.S. Ser. No. 13/177,657, which is incorporated by reference in its entirety.

In some embodiments, the ITK inhibitor has a structure selected from the group consisting of:
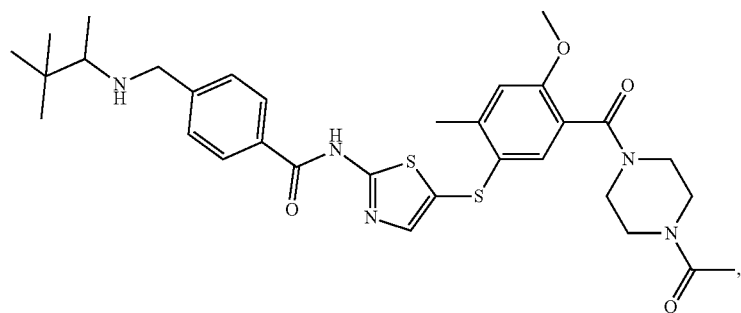
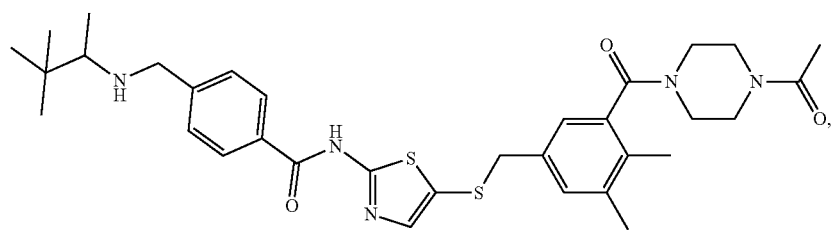
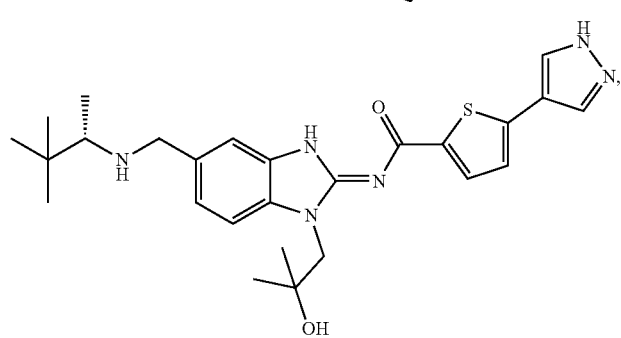
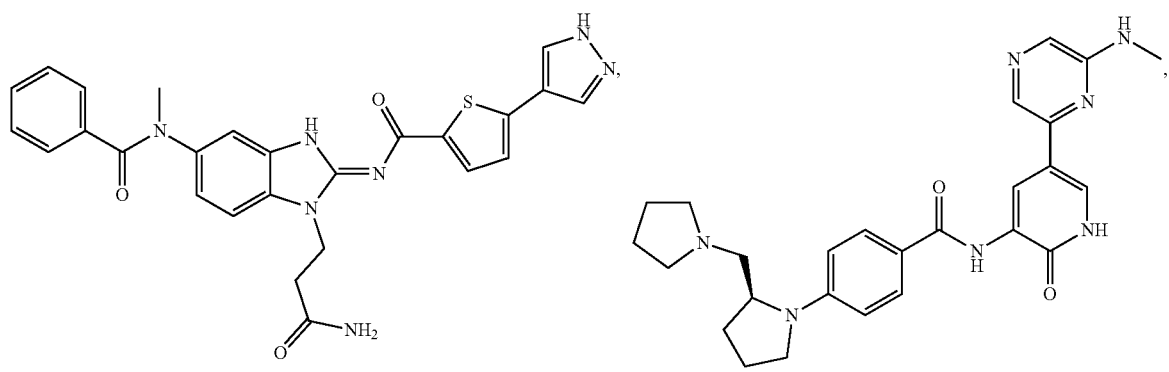
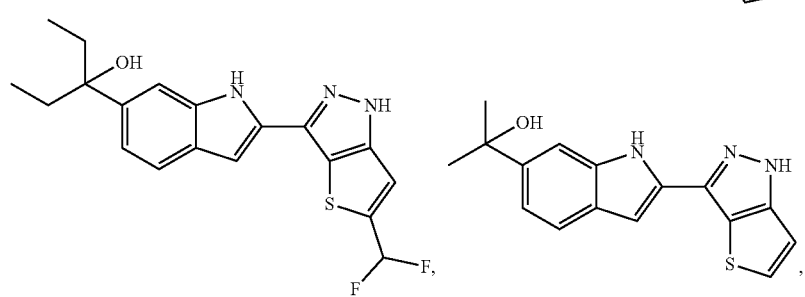

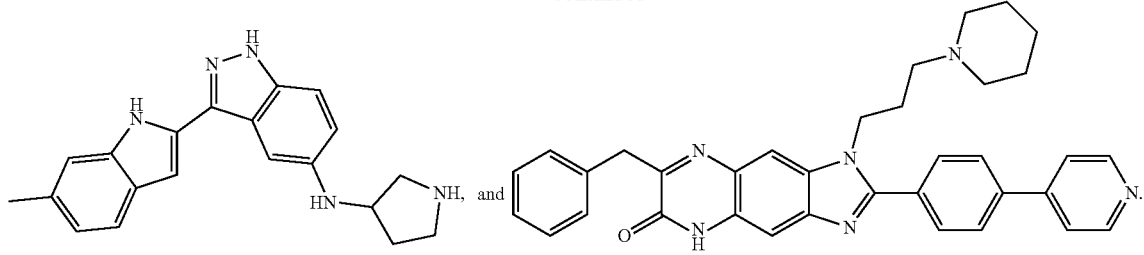

Pharmaceutical Compositions/Formulations

Disclosed herein, in certain embodiments, are compositions comprising a therapeutically effective amount of an ACK inhibitor compound, and a pharmaceutically acceptable excipient. In some embodiments, the ACK inhibitor compound (e.g., an ITK or BTK inhibitor, such as for example ibrutinib) is a compound of Formula (A). In some embodiments, the ACK inhibitor compound is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib).

Pharmaceutical compositions of ACK inhibitor compound (e.g., an ITK or BTK inhibitor, such as for example ibrutinib) are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

A pharmaceutical composition, as used herein, refers to a mixture of an ACK inhibitor compound (e.g., an ITK or BTK inhibitor, such as for example ibrutinib) with other chemical components, such as carriers, stabilizers, diluents, dispersing agents, suspending agents, thickening agents, and/or excipients.

Pharmaceutical compositions are optionally manufactured in a conventional manner, such as, by way of example only, by means of conventional mixing, dissolving, granulating, dragee-making, levigating, emulsifying, encapsulating, entrapping or compression processes.

The pharmaceutical formulations described herein are administered by any suitable administration route, including but not limited to, oral, parenteral (e.g., intravenous, subcutaneous, intramuscular), intranasal, buccal, topical, rectal, or transdermal administration routes.

The pharmaceutical compositions described herein are formulated into any suitable dosage form, including but not limited to, aqueous oral dispersions, liquids, gels, syrups, elixirs, slurries, suspensions and the like, for oral ingestion by an individual to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, the compositions are formulated into capsules. In some embodiments, the compositions are formulated into solutions (for example, for IV administration).

The pharmaceutical solid dosage forms described herein optionally include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In some embodiments, using standard coating procedures, such as those described in Remington's Pharmaceutical Sciences, 20th Edition (2000), a film coating is provided around the compositions. In some embodiments, the compositions are formulated into particles (for example for administration by capsule) and some or all of the particles are coated. In some embodiments, the compositions are formulated into particles (for example for administration by capsule) and some or all of the particles are microencapsulated. In some embodiments, the compositions are formulated into particles (for example for administration by capsule) and some or all of the particles are not microencapsulated and are uncoated.

In some embodiments, the pharmaceutical compositions are formulated such that the amount of the ACK inhibitor (e.g., an ITK or BTK inhibitor, such as for example ibrutinib) in each unit dosage form is about 140 mg per unit.

Kits/Articles of Manufacture

Described herein are kits for preventing the occurrence of graft versus host disease (GVHD) or reducing the severity of GVHD occurrence in a patient requiring cell transplantation comprising a therapeutically-effective amount of an ACK inhibitor compound (e.g., an ITK or BTK inhibitor, such as for example ibrutinib).

Further described herein are kits for treating a patient for alleviation of a bone marrow mediated disease, with alleviation of consequently developed graft versus host disease (GVHD) comprising a therapeutically effective amount of an ACK inhibitor compound (e.g., an ITK or BTK inhibitor, such as for example ibrutinib), wherein a therapeutically effective amount of an ACK inhibitor compound (e.g., an ITK or BTK inhibitor, such as for example ibrutinib) is administered prior to or concurrently with allogeneic hematopoietic stem cells and/or allogeneic T-cells.

For use in the therapeutic applications described herein, kits and articles of manufacture are also described herein. In some embodiments, such kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disorder that benefit by inhibition of BTK, or in which BTK is a mediator or contributor to the symptoms or cause.

The container(s) optionally have a sterile access port (for example the container is an intravenous solution bag or a vial having a stopper pierceable by a hypodermic injection needle). Such kits optionally comprise a compound with an identifying description or label or instructions relating to its use in the methods described herein.

A kit will typically include one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes, carrier, package, container, vial and/or tube labels listing contents and/or instructions for use, and package inserts with instructions for use. A set of instructions will also typically be included.

In some embodiments, a label is on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, a pharmaceutical composition comprising the ACK inhibitor compound (e.g., an ITK or BTK inhibitor, such as for example ibrutinib) is presented in a pack or dispenser device which can contain one or more unit dosage forms. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

Example 1: Immune Reconstitution and the Development of cGVHD

The influence of lymphocyte reconstitution at days 30 and 100 following allogeneic SCT on subsequent development of cGVHD was evaluated using of an extensive immune reconstitution flow cytometric "immunome" assay, which allowed for monitoring of changes in cell activation markers, memory T cell status, Treg subsets, NK cell subsets and Th1 vs Th2 cell subsets. Patients who developed cGVHD had a larger increase in CD4+ T cells and a smaller increase in CD8+ T cells compared with patients who did not develop cGVHD over time, suggesting a selective expansion of CD4+ T cells. Further, a significant decrease in NK cells and concomitant increase in percentages of activated B cells was noted. An increase in CD4+ cells is associated with an inflammatory phenotype, and a Th2-skewed proinflammatory response may contribute to B cell activation. The presence of a Th2-skewed phenotype was supported by the presence of increased CD4+/CD193+ cells among patients with cGVHD, as CCR3 is preferentially expressed on Th2 cells.

Example 2: Ibrutinib in a Murine Model of cGVHD

An established in vivo allo-bone marrow transplant (BMT) model system was used to preclinically test ibrutinib as a therapy for cGVHD. The LP/J→C57BL/6 model is a murine model of sclerodermatous cGVHD which develops dermal lesions characterized by hair loss, redness, flaking, scabbing, hunched posture, and thickened skin. In this murine model, external symptoms become apparent between days 20 and 25 and peak between days 37 and 47 post hematopoietic stem cell transplantation (HSCT).

C57BL/6 mice received lethal X-ray irradiation (850 cGy) followed by allo-BMT derived from MHC-matched LP/J mice. A small number of mature spleen cells were included in the transplant to seed the development of cGVHD. The studies demonstrated that approximately ⅓ of mice survived to day 25 post transplant and at that time began to develop classic external signs of cGVHD including scleroderma, hair loss, hunched posture, weight loss, and dermal fibrosis. Therefore, 25 days post-BMT was selected for treatment time point.

Ibrutinib Ameliorates cGVHD Symptomatology after Allotransplant

C57BL/6 mice were engrafted with LP/J bone marrow after 850 cGy lethal irradiation. 25 days post-transplant mice were randomly assigned to vehicle, cyclosporine, or ibrutinib cohorts and drug was administered via drinking water or intraperitoneal injection. Scoring was conducted on day 36 or day 39 post-transplantation using a physical scoring system adapted from Cooke et al., which incorporates weight, posture, coat condition, skin condition, and mobility.

These studies confirmed a dramatic therapeutic response to ibrutinib which allowed for complete resolution of cGVHD induced scleroderma, alopecia, weight loss, and paralysis as compared to vehicle or cyclosporine treatment groups (FIGS. 1A, D). The quality of therapeutic response was quantitatively assessed using a previously established scoring model for the assessment of hair loss, scleroderma, weight loss, posture, and mobility in mice suffering from cGVHD (FIG. 1B). In the scoring model, scores range from 0 (healthy mouse) to 19 (mouse which has died due to cGVHD) with 18 representing the maximum score for a living mouse with cGVHD (FIG. 1C). cGVHD progression was defined as a >2 point change in overall cGVHD score from treatment baseline. Histologic preparations of sclerodermatous skin lesions revealed dermal fibrosis, epidermal hyperplasia, serocellular crusting, erosion, and lymphohistiocytic infiltration, consistent with external examination (FIG. 1E). Normal dermal histology was observed in mice receiving therapeutic ibrutinib.

Figure 5:
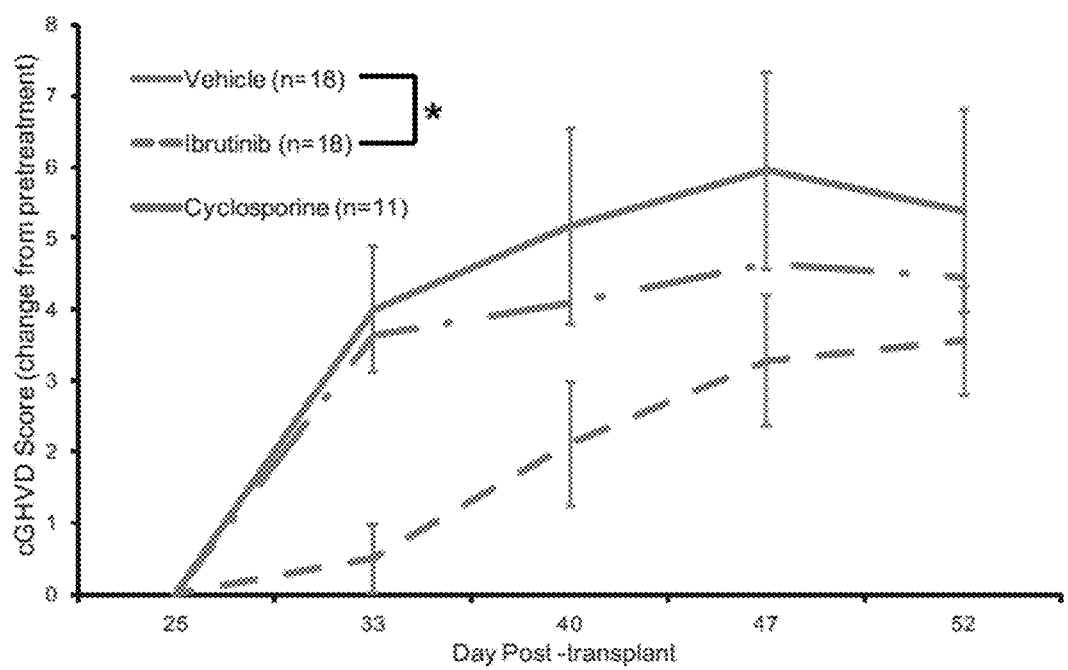
FIG. 5 exemplifies that ibrutinib inhibited cGVHD auto-immune symptomatology and progression. Panel A provides a plot of the weekly blinded analysis of cGVHD external metrics including weight, posture, vitality, mobility, coat, and skin. All cGVHD scores were corrected for individual scores at the beginning of treatment (day 25). Panel B provides a Kaplan Meier plot of cGVHD progression free survival. Progression is defined as >2 point increase in day 25 cGVHD score. *=p<0.01 Error bars=s.e.m.
Figure 5:
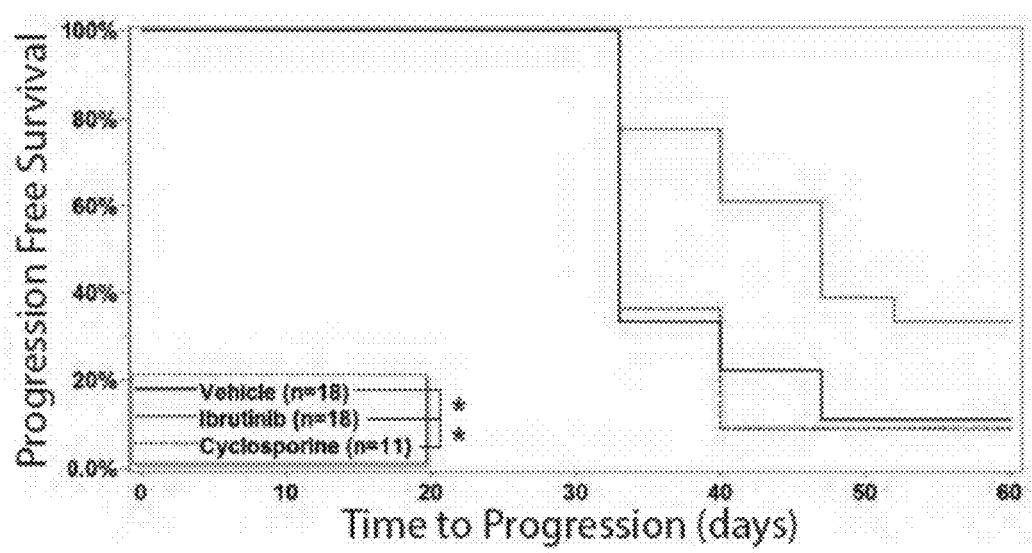

Ibrutinib significantly extended median time to cGVHD progression by 14 days and 33% (6 of 18) of ibrutinib treated mice remained progression free as compared to 12% (2 of 18) of mice receiving vehicle and 10% (1 of 11) of mice receiving cyclosporine 10 mg/kg/day (p<0.02) (FIG. 5). A 100% survival in the ibrutinib cohort as compared to 82 and 88% survival for cyclosporine and vehicle groups respectively, was observed. Weekly evaluation of mouse body-weight revealed little variation between groups with ibrutinib treated mice weighing slightly more on average.

Tregs were not Inhibited by Ibrutinib

In allo-BMT recipients, Tregs (regulatory T cells) control cGVHD by actively suppressing autoreactive T-cells within the periphery; unfortunately, most current therapies disrupt Treg development or functionality. To study the effects of ibrutinib on Tregs, C57BL/6 mice were treated with ibrutinib (25 mg/kg/day) or vehicle for 9 weeks and the percent FoxP3+CD4+ cells was analyzed by flow cytometry on peripheral blood. In addition, purified CD4+ CD25hiCD127dim CD49d-FoxP3+ Tregs were pretreated with 1 µM ibrutinib or vehicle and mixed with CF SE-labeled autologous CD8+ responder cells at different responder: suppressor ratios of 1:0, 1:1, 2:1, 4:1, 8:1, and 16:1. Anti-CD3/CD28/CD2 stimulation beads were added and stimulation was assessed by CFSE (carboxyfluorescein succinimidyl ester) dilution calculated division index after 6 days. Negative control wells contained no stimulation beads.

Figure 2:
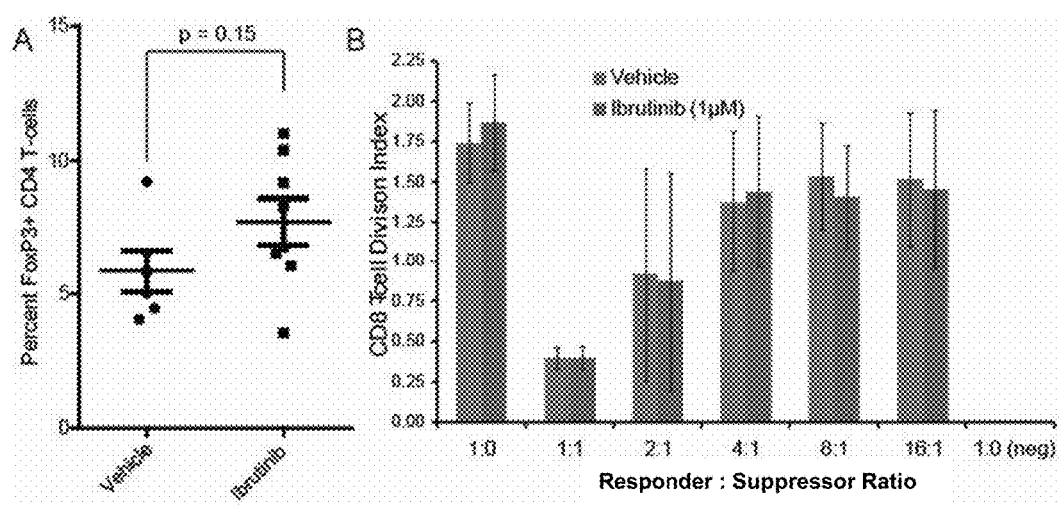
FIG. 2 exemplifies that Tregs are not inhibited by ibrutinib. Panel A provides a plot of FoxP3+ CD4+ cells in C57BL/6 mice treated with ibrutinib (25 mg/kg/day) or vehicle for 9 weeks. The percent FoxP3+ CD4+ cells was analyzed by flow cytometry on peripheral blood. Student's T-test indicates no significant difference between the two groups. Panel B provides a plot of CD8 T cell division index for various responder:suppressor ratios. Purified CD4+ CD25hiCD127dim CD49d-FoxP3+ Tregs were pretreated with 1 µM ibrutinib or vehicle and mixed with CF SE-labeled autologous CD8+ responder cells at the indicated ratio. Anti-CD3/CD28/CD2 stimulation beads were added and stimulation was assessed by CFSE dilution calculated division index after 6 days. Negative control wells contained no stimulation beads. n=7; error bars: s.e.m.

The in vivo data showed that ibrutinib did not diminish overall Treg numbers after 9 weeks of continuous ibrutinib therapy (FIG. 2A). The in vitro data indicated that the suppressive function of human Tregs was maintained after ibrutinib treatment as assayed by an in vitro T-cell suppression assay (FIG. 2B). The data showed that ibrutinib had the ability to suppress anti-host immunity while preserving Treg function, which is important for the graft-versus-tumor effect.

Th2 Immunity was Inhibited by Ibrutinib

Figure 3:
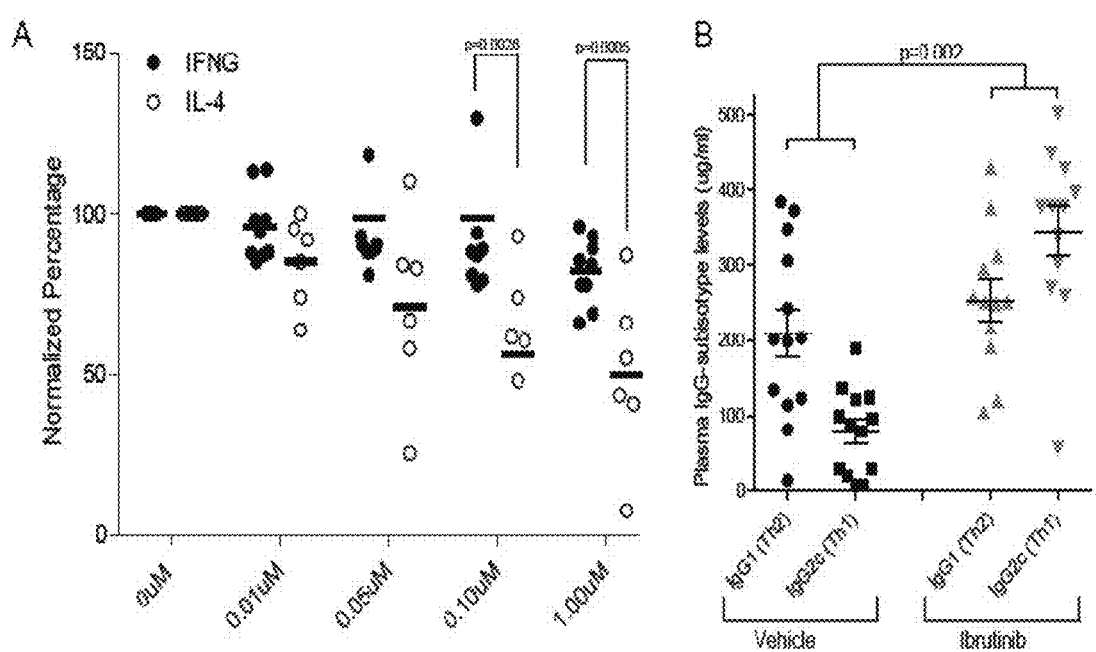
FIG. 3 exemplifies that Th2 immunity was inhibited by ibrutinib. Panel A provides a plot of normalized intracellular staining analysis of IL4 (open bars n=6) and IFNγ (closed bars n=9) CD4+ cells derived pretreated with ibrutinib and stimulated with anti-CD3/anti-CD28. Error bars=s.e.m. Panel B provides a plot of plasma IgG1 (Th2) and IgG2c (Th1) subisotype analysis of C57BL/6 EµTCL1 mice at 8 months of age after 7 consecutive months of ibrutinib (25 mg/kg/day) (n=12) or vehicle (n=13) administration via drinking.

Intracellular staining was performed for IFNγ and IL4 in ibrutinib-treated, TCR-stimulated CD4+ T-cells. Following stimulation, a significant decrease was identified in the IL4-producing Th2 population of CD4+ T-cells, whereas IFNγ-producing Th1 cells were largely unaffected (FIG. 3A). These data confirmed that a significant divergence of the two cell populations was achieved in a purified T-cell culture at ibrutinib doses ranging from 0.1-1 µM. This dose range was consistent with serum concentrations observed in vivo during pharmacokinetic studies of ibrutinib in both mouse and human trials. To assess the long-term implications of ibrutinib-induced Th1 cytokine skewing, IgG sub-isotype analyses were conducted in a cohort of 8 month old C57BL/6 EµTCL1 mice. These mice were treated continuously for 7 months with ibrutinib (25 mg/kg/day) or vehicle. Results revealed a significant (p=0.002) inversion of the Th1/Th2 ratio as measured by the relative levels of IgG1 (Th2) and IgG2c (Th1), confirming an in vivo ibrutinib-related Th1 skewing (FIG. 3B).

Th17 Immunity was Inhibited by Ibrutinib

Figure 4:
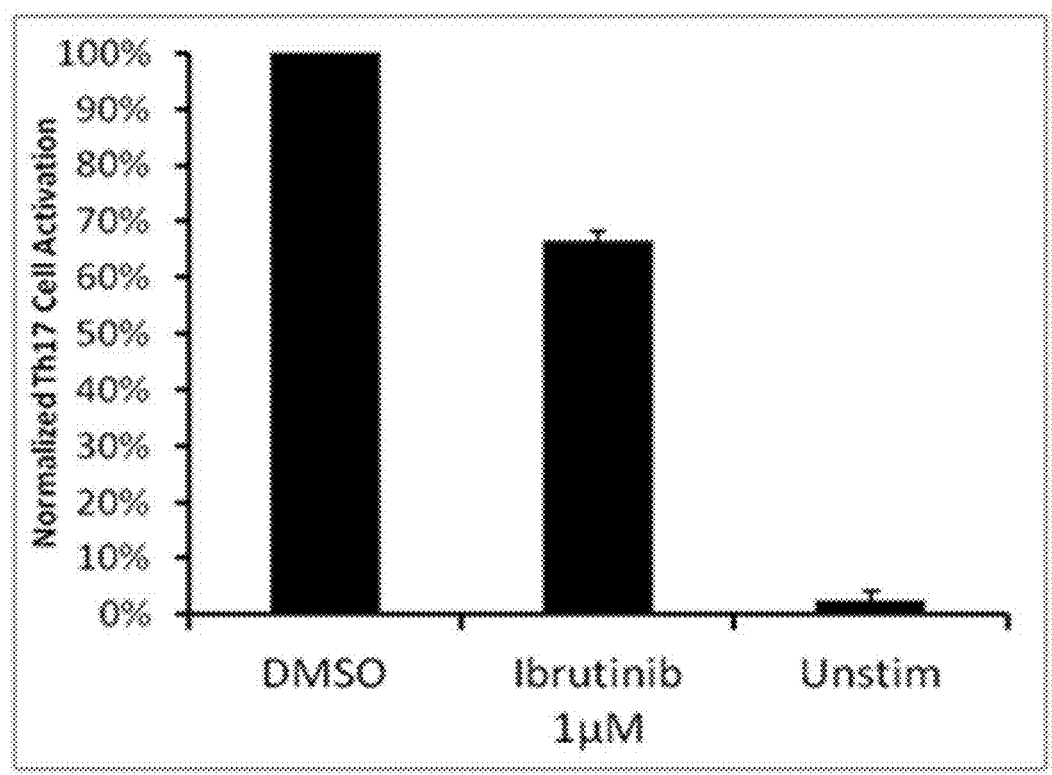
FIG. 4 exemplifies that Th17 immunity was inhibited by ibrutinib. Th17 cells were magnetically enriched from freshly isolated healthy donor PBMCs using CXCR3-CD4+ CCL6+ isolation. After enrichment cells were treated with ibrutinib or vehicle for 30 minutes prior to drug washout. Cells were stimulated with anti-CD3 and anti-CD28 for 12 hours with GOLGISTOP protein transport inhibitor. IL17 producing cells were quantified as a percentage of total live CD4+ T-cells and final percentages were normalized to DMSO group. n=3; error bars: s.e.m.

In cGVHD, there is a common link in which alloreactive Th2 and Th17 T-cells drive pro-fibrotic pathways and B-cell autoantibody production as a result of defective thymic conditioning. Given the role of Th17 cells, the effect of ibrutinib on this specific T-cell subtype was investigated. Healthy donor Th17 cells were magnetically isolated from freshly isolated healthy donor PBMCs using CXCR3-CD4+ CCL6+ isolation and TCR stimulation for 12 hours following 30 minute pretreatment with vehicle or 1 µM ibrutinib. The percentage of IL17 secreting CD4+ T-cells was quantified by intracellular cytokine staining and normalized to vehicle treatment (FIG. 4). The data indicated that ibrutinib limited the TCR-induced activation of Th17 cells.

Ibrutinib Therapeutically Controlled cGVHD-Induced Organ Injury

Figure 6:
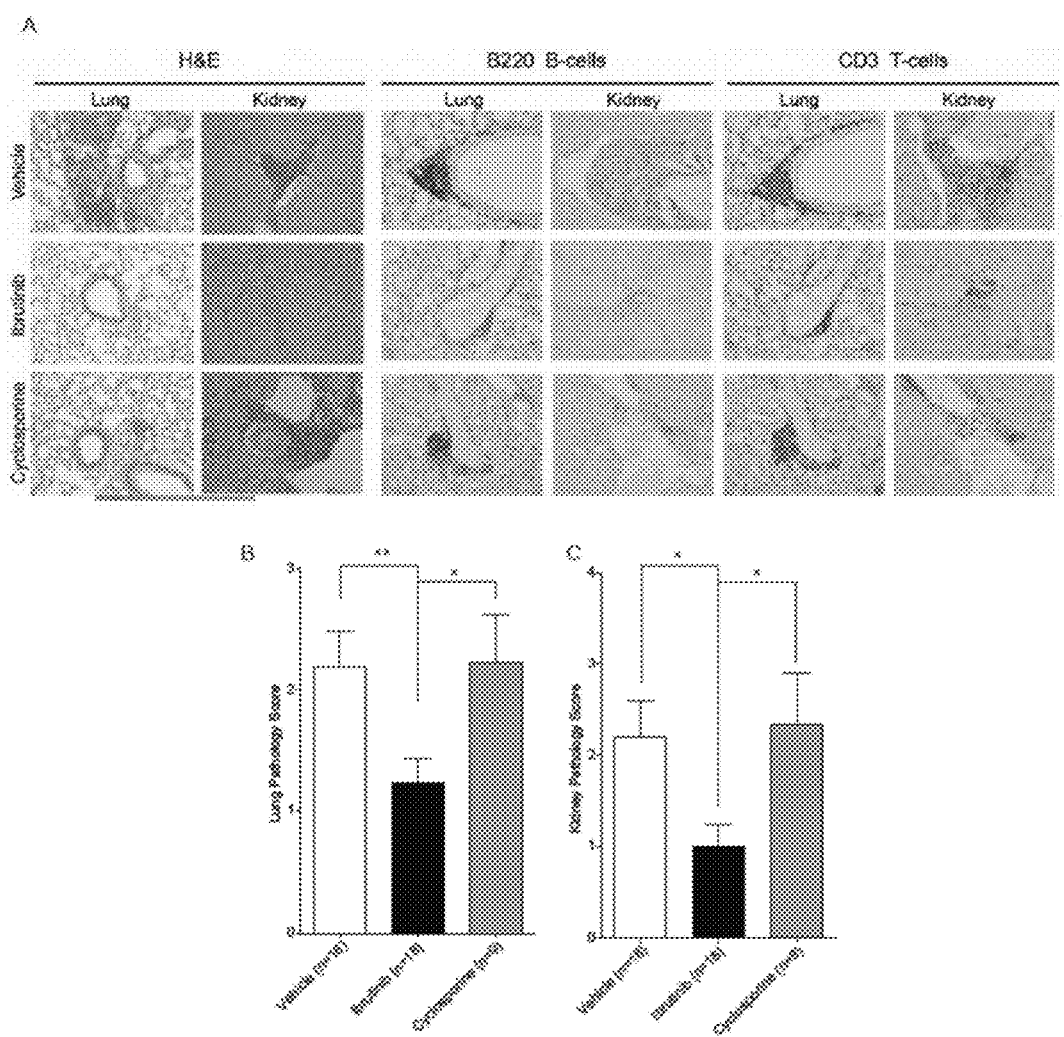
FIG. 6 exemplifies that ibrutinib therapy combats auto-immune infiltration of internal organs in a T-cell dependent model of cGVHD. Panel A shows representative 20× images from H&E, B220, or CD3 stained lung and kidney tissues from mice sacrificed at day 125 post-HSCT. Images were taken by a trained veterinary pathologist who was blinded to animal cohorts. Panel B shows a blinded pathologic analysis of H&E stained lung tissues obtained from cGVHD cohorts. Lymphohistiocytic infiltration was graded on a 0-4 scale for each animal. Panel C shows a blinded pathologic analysis of H&E stained liver tissues obtained from cGVHD cohorts. Portal hepatitis and vasculitis was graded on a 0-4 scale for each animal. Panel D shows a Kaplan-Meier plot of cGVHD progression-free survival in an independent experiment aimed to determine sustained benefits from continued ibrutinib therapy. During the course of the experiment, ibrutinib was withdrawn on day 60 from animals in the Ibrutinib (day 25 to day 60) cohort. **P<0.001.
Figure 6:
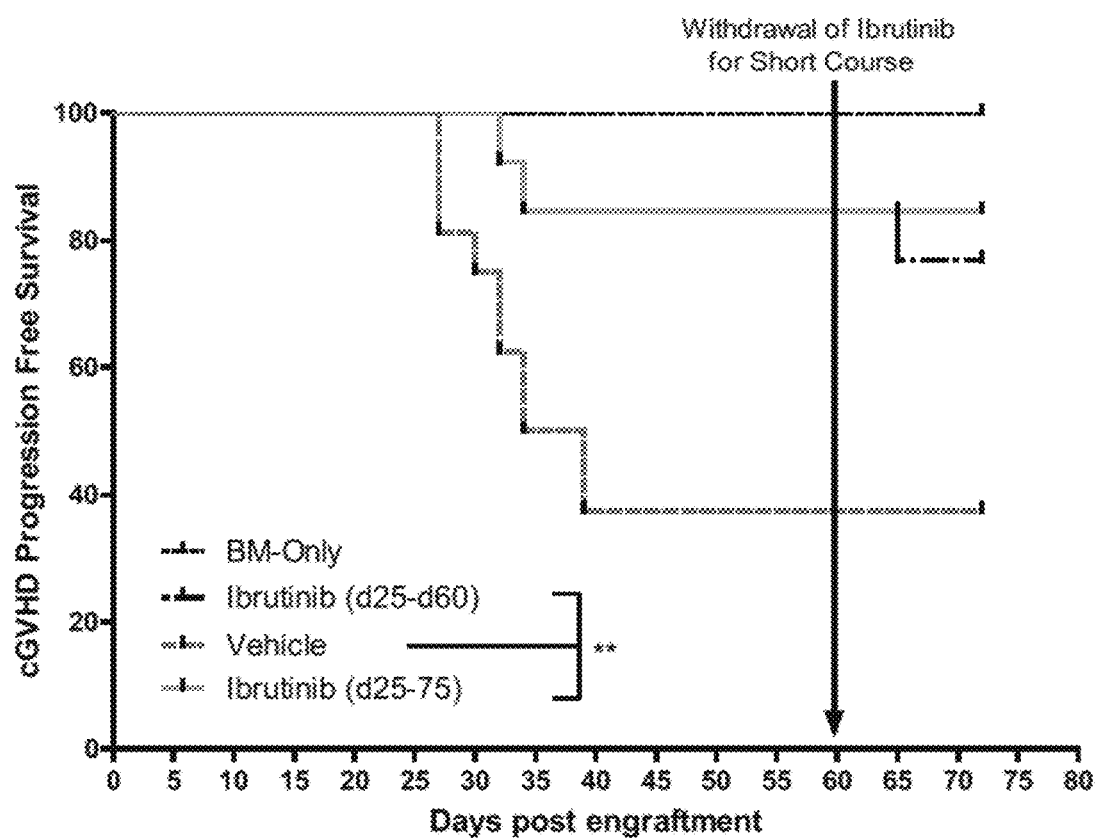

In addition to the externally measurable cGVHD metrics, it was found that the LP/J→C57BL/6 model developed pulmonary and renal cGVHD, apparent upon histologic assessment. Evaluation of H&E stained sections revealed that ibrutinib therapy systemically limited cGVHD-induced aggregates of lymphocytes, plasma cells, and histiocytes surrounding bronchioles and small caliber vessels throughout the pulmonary parenchyma and within the renal interstitium. Immunohistochemistry revealed B220+ B-cell and CD3+ T-cell pulmonary infiltration in addition to CD3+ T-cell renal infiltration in both the vehicle and cyclosporine groups which was not observed in ibrutinib treatment groups (FIG. 6A). Coded pathologic analysis by a trained veterinary pathologist confirmed that ibrutinib improved internal systemic cGVHD in this model (FIGS. 6B and C).

An additional long-term therapeutic experiment was conducted (FIG. 6D). Once again, ibrutinib significantly limited cGVHD progression as compared with vehicle control (P=0.0019). It was also found that withdrawal of therapy at day 60 permitted clinical breakthrough cGVHD in a single mouse (1 of 6); however, this was not statistically significant. A similar trend was observed by external cGVHD scoring. Analysis of internal cGVHD pathology within the pulmonary and renal tissues on day 75 suggested that continuous long-term ibrutinib was more effective at controlling cGVHD; notably, internal pathology of the lung and kidney was not curtailed in BM-only recipients, indicating that certain cGVHD internal pathology in this model persists despite the elimination of T cells from the graft similar to what is observed in human allo-HSCT recipients. Prophylactic ibrutinib treatment initiated pre-HSCT at day −2 and concluded at day 25 did not yield a significant improvement in cGVHD progression, suggesting that ibrutinib will be most effective when T and B cell responses are more fully developed.

Example 3: Ibrutinib Inhibition of CD4 T-Cell and B-Cell Activation in Cells from Patients with cGVHD CD4+ T-Cell Activation in Cells from cGVHD Patients Inhibited by Ibrutinib Primary CD4+ T-cells were isolated from patients with active cGVHD, pretreated with 1 µM ibrutinib (or DMSO), and stimulated using anti-CD3 for 6 hours. Quantitation of the activated T-cell percentage for each patient showed a significant decrease in the population of CD69+ CD4+ T-cells (FIG. 7A) in cells pretreated with ibrutinib as compared to DMSO.

B-Cell Activation in Cells from cGVHD Patients Inhibited by Ibrutinib

B-cells isolated from patients with cGVHD were pretreated with 1 µM ibrutinib and stimulated with anti-IgM for 45 minutes. Analysis of B-cell receptor pathway activation using phospho-specific antibodies for pERK1/2, pBTK, and pPLCγ2 revealed that ibrutinib was effective in inhibiting the B-cell receptor pathway (FIG. 7B). These data confirmed that ibrutinib curtailed immune receptor activation in human B and T cells in the setting of active cGVHD.

Example 4: Clinical Studies of Ibrutinib in CLL and Lymphoma

Fifty-six patients, including 16 with CLL, were treated on the initial phase I study of ibrutinib. Seven cohorts were evaluated: 5 cohorts where patients were treated on a 28 days on, 7 days off schedule, and 2 cohorts where patients were treated on a continuous dosing schedule at 8.3 mg/kg daily or a fixed dose of 560 mg once daily. Patients had received a median of 3 prior regimens, and the median age was 65, with the oldest patient being 82 years old. The maximum tolerated dose was not reached, and only 2 dose-limiting toxicities were observed: a grade 3 allergic hypersensitivity in a patient with a history of drug hypersensitivities; and a dose interruption for more than 7 days because of transient grade 2 neutropenia. Using a competitive binding assay to evaluate, ≥95% BTK occupancy was achieved 4 hours post dose in all patients receiving 2.5 mg/kg/day. Thus, doses of 420 mg and 840 mg given daily were selected for further study. Of 50 patients evaluable for tumor response, 60% achieved an objective response (CR or PR). Responses were observed across all histologies, including in 11 of the 16 patients with CLL/SLL. All of the patients with CLL who responded had rapid reduction in lymphadenopathy during the first cycle accompanied by an increase in the absolute lymphocyte count, and all but one had an eventual reduction in the ALC to meet IWCLL criteria for a PR. Responses were durable, with a median progression-free survival of 13.6 months.

Based on the impressive responses in CLL patients seen in the phase I study, a phase Ib/II study was conducted in patients with CLL. Patients were enrolled in one of 5 cohorts evaluating ibrutinib at a fixed dose of 420 mg daily or 840 mg daily. Cohorts evaluated patients who were treatment-naïve and at or above the age of 65, relapsed or refractory after 2 or more prior lines of treatment, including a purine-nucleoside analog, or high-risk, with relapse within 2 years of receiving chemoimmunotherapy, or the presence of del17p. One-hundred-and-sixteen patients were enrolled: 31 treatment-naïve patients, 61 in the relapsed/refractory cohorts, and 24 high-risk patients. The overall median follow-up was 16.6 months, with 4 median prior therapies in both the relapsed/refractory and high-risk cohorts. The most common adverse events noted were diarrhea, fatigue, upper respiratory tract infection, rash, nausea, and arthralgia, and most were grade 2 or less. Importantly, no evidence of cumulative toxicity has been reported. Responses were observed, independent of poor-risk factors including advanced disease stage, increasing numbers of prior therapies, higher beta-2-microglobulin, or poor-risk cytogenetics, with an ORR of 67% in patients with del17p in the relapsed/refractory cohorts. The estimated 22 month PFS for the 85 patients in the relapsed/refractory and high-risk cohorts was 76% and was 96% for the 31 treatment-naïve patients. The estimated 22 month overall survival for these two groups respectively was 85% and 96%. Median progression-free and overall survivals for any of the cohorts had not been met at the time.

Example 5: Clinical Study of Ibrutinib in Patients with Steroid Resistant or Refractory Chronic Graft-Versus-Host Disease (cGVHD)

cGVHD and its associated immune deficiency has been identified as a leading cause of non-relapse mortality (NRM) in allogeneic SCT survivors. SCT survivors with cGVHD are 4.7 times as likely to develop severe or life-threatening health conditions compared with healthy siblings, and patients with active cGVHD are more likely to report adverse general health, mental health, functional impairments, activity limitation, and pain than allo-SCT survivors with no history of cGVHD. Rituximab notwithstanding, historical response rates with a number of investigational agents in steroid-refractory cGVHD have been around 30%, so this is a patient population with a clear need for an effective intervention to reduce dependence on steroids and improve quality of life and survival. Ibrutinib induces apoptosis in B lymphocytes through inhibition of the BCR pathway and antagonizes multiple external microenvironment survival signals mediated through cytokines such as BAFF, and it can reverse Th2 polarization. It has thus far been shown to be safe in the treatment of patients with relapsed or refractory B cell lymphomas and CLL, with the most common toxicities being diarrhea, fatigue, upper respiratory infection and rash, and being grade 2 or less. Importantly, no cumulative toxicities were noted, allowing long-term use of the drug. In comparison, long-term use of the steroids and calcineurin inhibitors used to treat cGVHD is known to cause adverse effects, leading to much of the morbidity and mortality seen in patients with cGVHD. Based on ibrutinib's tolerability in early phase studies and its mechanism of action, it was expected that this would be a well-tolerated agent and with clinical efficacy against cGVHD.

For the primary objectives of evaluating safety and efficacy of ibrutinib when used for cGVHD, it is expected that ibrutinib will be well tolerated in patients with steroid-dependent/refractory cGVHD and will improve response at 12 weeks compared with the historical response rate of 30%. Further, it is expected that use of ibrutinib will allow faster tapering of steroids and will contribute to improved quality of life at 1 and 2 years compared with historical controls. Because patients will be exposed to less corticosteroids, it is expected that relapse rates of primary disease will improve with ibrutinib, particularly in patients who receive a transplant for a lymphoid malignancy, in which ibrutinib has documented efficacy in phase II studies. Because ibrutinib has effects on ITK it is expected that compared to institutional controls, use of ibrutinib in this setting will skew towards a Th1 phenotype, which will be evaluated through serial evaluation of immune reconstitution by flow cytometry. Additionally, it inhibits activation of Th17 cells, while preserving the function and numbers of Tregs, thereby preserving the graft-versus-tumor effect while treating GVHD.

Objectives of the Study:

1. Primary endpoint:

To determine the safety of ibrutinib when given for chronic GVHD (Phase Ib portion)

To evaluate the response rate (CR+PR) at 12 weeks using ibrutinib as a treatment for steroid-refractory or -resistant chronic GVHD (Phase II portion)

2. Secondary endpoints:

To evaluate the impact of ibrutinib on steroid dose at 12 weeks, 6 months, 1 year, and 2 years To evaluate response at 6 months and 1 and 2 years To evaluate overall survival at 1 and 2 years To evaluate the relapse rate (both primary disease and cGVHD symptoms) at 1 year To evaluate the incidence of grade 3-5 infections during treatment To evaluate quality of life at 1 and 2 years To evaluate effect on immune reconstitution at 1 and 2 years Eligibility Criteria:

1. Classic or overlap chronic GVHD that is resistant or refractory to corticosteroids (equivalent to at least 0.5 mg/kg/day or 1 mg/kg/every other day prednisone for at least one month of treatment). Organ-specific topical therapy permitted 2. History of allogeneic stem cell transplant for hematologic malignancy 3. Age 18-75 years at the time of registration 4. Within seven days of administration of the first dose of ibrutinib, the patient must have adequate organ function and performance status as follows:

Absolute neutrophil count (ANC)≥500/μL

Platelets ≥30,000/μL

Total bilirubin ≤2.5× institutional upper limit of normal unless due to Gilbert's disease unless attributable to cGVHD AST (SGOT)≤2.5× institutional upper limit of normal unless attributable to cGVHD Creatinine clearance ≥40 mL/min 5. ECOG performance status ≤2

6. Life expectancy ≥12 weeks

7. Willing and able to participate in all required evaluations and procedures in this study protocol 8. Able to understand the purpose and risks of the study and provide signed and dated informed consent and authorization to use protected health information (in accordance with national and local subject privacy regulations)

Exclusion Criteria:

1. New immunosuppression within 4 weeks of starting ibrutinib

2. "Currently active" malignancy, except for adequately treated basal cell or squamous cell skin cancer, in situ cervical cancer, or other cancer from which the subject has been disease free for at least 2 years, aside from the primary indication for transplant, or which will not limit survival to less than 2 years 3. A life-threatening illness, medical condition or organ system dysfunction which, in the investigator's opinion, could compromise the subject's safety or put the study outcomes at undue risk 4. Active and uncontrolled bacterial, fungal, or viral infection 5. Significant cardiovascular disease such as uncontrolled or symptomatic arrhythmias, congestive heart failure, or myocardial infarction in absence of significant predisposing cause (i.e., severe autoimmune hemolytic anemia or sepsis) within 6 months of screening, or any Class 3 or 4 cardiac disease as defined by the New York Heart Association Functional Classification 6. Known history of Human Immunodeficiency Virus (HIV) or active infection with Hepatitis C Virus (HCV) or Hepatitis B Virus (HBV) or any uncontrolled active systemic infection.

7. Concurrent antineoplastic therapy after hematopoietic stem cell transplant

8. Lactating or pregnant

9. Will not agree to use highly effective contraception (e.g., condoms, implants, injectables, combined oral contraceptives, some intrauterine devices [IUDs], sexual abstinence, or sterilized partner) during the study and for 30 days after the last dose of study drug (Note: applies to men and women of child-bearing potential only)

Study Design:

1. Overview

This is a non-randomized, open-label phase Ib/II study for patients with steroid resistant or refractory chronic graft-versus-host disease (cGVHD), equivalent to at least 0.5 mg/kg/day or 1 mg/kg/every other day prednisone for at least one month of treatment, following allogeneic stem cell transplant for hematologic malignancy. If a patient is on a calcineurin inhibitor and the level is less than 5 ng/ml at the start of the study, it will be stopped. Following enrollment, patients will be started on 420 mg ibrutinib daily, based on phase I and II studies in hematologic malignancies demonstrating that this dose is well tolerated and that 90% of the BTK active sites are occupied at this dose. For ease of documentation and follow-up, a cycle will be defined as 28 days. Treatment is oral, and will be administered on an outpatient basis. The first six patients will be subject to a dose-limiting toxicity (DLT) assessment period. The DLT period will be 28 days following initial administration of the drug, and the sixth patient must complete the DLT period before accrual can continue. A DLT is defined as the following: grade 2 acute graft-versus-host disease (biopsy-proven preferable but not necessary); grade 4 thrombocytopenia that does not improve to 80% of baseline or better following a 14-day treatment-free period without disease progression; grade 4 febrile neutropenia or infection; grade 3 febrile neutropenia or infection that fails to resolve within 7 days; any Grade 4 non-hematologic toxicity excluding infection; and grade 4 electrolyte abnormalities if not corrected by optimal replacement therapy.

The initial steroid taper may start at 4 weeks following initiation of ibrutinib, but the steroid dose may not be lower than 50% of the starting dose by the end of the third cycle (12 weeks). Patients will have a physical exam with comprehensive cGVHD evaluation at the beginning of each cycle. Patients will be assessed for response at the end of cycle 3, and if there is no improvement in symptoms, then this will be considered a treatment failure and they will come off study. Additionally, patients who require additional treatment for cGVHD prior to the response assessment at the end of cycle 3 will be considered a treatment failure, and these patients will be removed from study. If patients are in a CR or PR at the 12 week assessment, they will continue on daily ibrutinib while steroids are tapered. Once the steroids have been tapered off, ibrutinib can be discontinued. If patients are deriving clinical benefit allowing for reduction of steroid dose at the 1 year assessment point, then they will be allowed to continue on study for a maximum of 24 months. GVHD will be assessed monthly, and correlative studies, including immune reconstitution, B and T cell activation, serum immunoglobulins, and serum BAFF levels will be assessed every 3 months. Symptom burden and quality of life studies including the Lee cGVHD symptom scale, the 10-point cGVHD activity assessment, the FACT-BMT, SF36, and Human Activity Profile will be assessed at 12 weeks, 6 months, 1 year, and 2 years.

2. Ibrutinib Therapy

Ibrutinib will be administered daily each day of a 28 day cycle. The first administration of ibrutinib will define C1D1. A fixed dose of 420 mg will be administered. A comprehensive chronic graft-versus-host assessment according to NIH consensus criteria 35 will be performed at baseline in order to determine organ-specific and global score. The comprehensive assessment will be repeated at the end of cycle 3. This study will be performed using a phase Ib/II study design, in which the phase II portion will be conducted as a Simon optimal 2 stage design. If no more than 5 of the initial 15 patients, including the 6 enrolled in the phase Ib portion, have evidence of a CR or a PR at the 12 week assessment, the study will be stopped for futility. At the treating physician's discretion, the initial taper of prednisone may begin 2 weeks following initiation of ibrutinib if a clinical response is seen. The prednisone may not be tapered below 50% of the original dose by the 12 week assessment period, and an increase in cGVHD symptoms during steroid taper requiring an increase in steroid dose to NO MORE than the original dose will not be considered progression. However, if a patient requires a steroid dose higher than the original dose or the addition of a new treatment for cGVHD at any point, this will be considered evidence of progressive disease and will require removal from study. Because approximately 66% of patients with cGVHD are expected to progress, regardless of therapy, stopping rules will be triggered if more than 75% of patients progress prior to the assessment at the end of cycle 3. Daily ibrutinib will continue until steroids have been tapered off. A specific prednisone taper schedule will not be mandated. Once steroids are off, ibrutinib will continue for an additional 4 weeks, then stop. Patients may continue on ibrutinib for 2 years, and patients who are able to stop ibrutinib will be followed for 2 years from the start of treatment for secondary endpoints.

Endpoints/Statistical Considerations: This study will be conducted in 2 parts, a phase Ib portion and a phase II portion. Six patients will initially be enrolled to the phase Ib portion of the study. Analogous to a maximum tolerated dose (MTD) evaluation, the regimen will be considered sufficiently tolerable if at most one of these 6 patients experiences a DLT during the observation period of 28 days, in which case the study will progress to the phase II portion. Using a Simon optimal two-stage phase II design, in order to test the null hypothesis that the overall response rate will be 30% against the alternate hypothesis that the overall response rate will be 50%, with a one-sided type I error of 0.1 and 80% power, 32 patients will be needed. Of over 100 allogeneic transplants perform annually by the inventors, approximately half of these ultimately develop cGVHD. Approximately 50% of these will have disease that is not responsive to initial treatment with steroids, resulting in approximately 20 incident cases of cGVHD at Ohio State annually. The study is expected to accrue approximately 1 patient per month, resulting in a nearly 3 year accrual period if performed at a single institution. Transplant volumes are slightly lower at the University of North Carolina and the University of Chicago, and therefore, with the addition of these 2 sites, it would be expected to be able to fully accrue in approximately 24 months. If at most 5 of 15 patients in the first stage respond at the 12 week assessment point, the study will be terminated. If at most 12 patients respond overall, this treatment will not be considered worthy of further pursuit. In general, regardless of treatment, it is expected that approximately 66% of patients will have progressive disease by 6 months after starting treatment. Therefore, stopping rules will be triggered if 75% of patients or more enrolled prior to the interim analysis cutoff develop worsening cGVHD requiring treatment escalation within the first 12 weeks (3 of 4 patients, 6 of 8 patients, and 9 of 12 patients).

Response will evaluated by NIH consensus criteria for GVHD grading.

Complete response (CR) will be defined as complete resolution of symptoms attributable to GVHD.

Partial response (PR) will be defined as the presence of an objective response in one involved organ with no evidence of progression elsewhere and no requirements for additional systemic therapy.

The length of follow-up will be 24 months, and the estimated accrual period will be 2 years.

Patient characteristics will be presented as median and range for continuous variables and as frequency and percentage for categorical variables. Laboratory correlates will be summarized at each time point using descriptive statistics. The non-parametric Wilcoxon signed-rank procedure will be used to compare to baseline values for correlative studies. For the quality-of-life correlates, a 0.5 standard deviation change will be considered statistically significant. Logistic regression models will be fitted to find correlations that merit further research in future studies. Time-course plots will be generated for each patient and repeated measures analysis of variance will be used to explore relationships. The κ statistic will be used to evaluate agreement between the NIH response and clinically meaningful improvement in the quality of life measures.

Example 6: CLL/GVHD Case Study

A 52 year old male with high risk 17p del CLL was originally diagnosed in November 2002. In 2003, he was initially treated with six cycles of fludarabine, cyclophosphamide, and rituximab (FCR) and achieved a complete response. He recurred one year later with a right pleural effusion and retroperitoneal/mesenteric lymph nodes. In December 2006, peripheral blood fluorescence in situ hybridization (FISH) showed 23 percent of the cells to be 17p deleted and CT scan showed increasing adenopathy. In March 2007, his bone marrow was hypercellular and diffusely infiltrated with CLL (62 percent of CD45+ cells). By April 2007, he was restarted on FCR and received four cycles with a partial response (bone marrow showing persistent disease with 44 percent CD45+ cells). Because of his persistent disease and p17 del diagnosis, he received Campath (alemtuzumab) for a total of 20 doses and a subsequent bone marrow biopsy in October 2007 showed no CLL and the PET/CT was negative.

In November 2007, the patient underwent a non-myeloablative allogeneic hematopoietic stem cell transplant using total lymphoid irradiation and antithymocyte globulin (TLI/ATG) with infusion of GCSF mobilized peripheral blood stem cells from his matched related sibling donor (sister). His oral graft versus host disease (GVHD) prophylaxis consisted of cyclosporine (CSA) and mycophenolate mofetil (MMF). He was transplanted on a Stanford research protocol (BMT 172) that incorporated rituximab 375 mg/m2 infused post-transplant on days 56, 63, 70, and 77.

The patient's post-transplantation course was complicated by infectious complications (multi-lobar fungal pneumonia, influenza A, varicella zoster reactivation) and post-transplant lymphoproliferative disorder (PTLD) treated with nine doses of rituximab in 2008. The patient never achieved full donor chimerism post-HCT. By September 2008, approximately nine months post-HCT, he was found to have disease progression by flow cytometry and a CT scan that showed some retroperitoneal adenopathy enlargement from prior study. Due to the patient's mixed donor chimerism and disease progression, the patient received a total of five donor lymphocyte infusions (DLIs).

The patient's first DLI was given in September 2008 at a dose of $1 \times 10^7$ donor CD3+ cells/kg recipient body weight. No GVHD or disease response. He received a second DLI in November 2008 at a dose of $3 \times 10^7$ donor CD3+ cells/kg recipient body weight. He was found to have a decrease in his allele-specific oligonucleotide (ASO) quantification results with reduction from 268,000 clonal IgH sequences per mcg of DNA down to 120. There was also an increase in donor blood T cell chimerism to 90% in January 2009 with associated mild oropharyngeal chronic GVHD. Bone marrow biopsy in April 2009 showed only 10% CLL. He received a third DLI in May 2009 at a dose of $5 \times 10^7$ donor CD3+ cells/kg recipient body weight. The patient also received a cycle of rituximab (4 doses during this time). Approximately 18 days after his third DLI, he developed oral GVHD with erythema and ulceration associated with a dramatic increase in donor T cell chimerism from 71 percent on day of DLI infusion to 87 percent 11 days later and up to 97 percent 25 days later. He did not require systemic steroid therapy for the GVHD but required local therapy and it persisted for about a year.

In the summer of 2009, the patient's PET/CT scan showed disease progression with bulky disease in the chest/abdomen and a bone marrow biopsy with 40 to 50 percent CLL. For this persistent disease, the patient was subsequently treated with combination chemotherapy with four cycles of OFAR (oxaliplatin, fludarabine, cytarabine, rituximab). In December 2009, the patient received a fourth DLI at a dose of $5 \times 10^7$ donor CD3+ cells/kg recipient body weight. GVHD flared when his donor chimerism reached above 95 percent following OFAR. However, his disease persisted, so he was given a fifth DLI in February 2010 at a dose of $1 \times 10^6$ donor CD3+ cells/kg recipient body weight. His oral GVHD required local steroid treatment. His bone marrow biopsy performed in May still showed 50 percent CLL.

Figure 8:
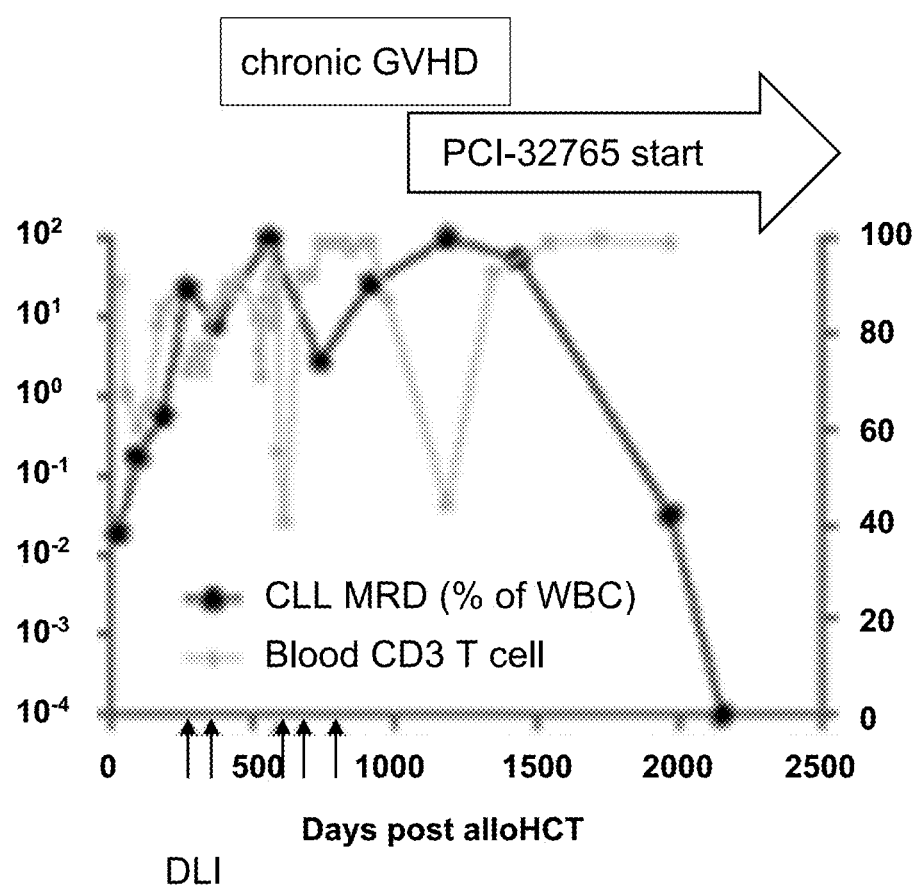
FIG. 8 exemplifies a clinical study of ibrutinib (PCI-32765) treatment of a post-allogeneic HCT transplant patient with refractory CLL with oropharyngeal chronic GVHD. CLL minimum residual disease (MRD) and blood CD3+ T cell donor chimerism is shown over time following allo-HCT transplantation. Donor lymphocyte infusions (DLI) and initiation of ibrutinib treatment are indicated (see Example 5 for exemplary treatment protocol).

By August 2010, the patient's PET/CT showed rapidly progressive disease and recurrence of massive lymphadenopathy including an abdominal mass up to 12 centimeters in diameter. In September 2010, the patient was enrolled in a clinical trial with ibrutinib (oral BTK inhibitor) through Stanford's Hematology group and completed over three years of therapy on ibrutinib, and achieved a complete response in both the bone marrow and on CT (see FIG. 8). In addition, his oral GVHD symptoms completely resolved and he achieved a durable full donor chimerism (see FIG. 8).

In summary, this post-allogeneic HCT CLL patient had refractory CLL with oropharyngeal chronic GVHD that resolved with ibrutinib therapy. His CLL was undetectable using B cell IgH sequencing (CLONOSIGHT minimal residual disease test (Sequenta, Inc.)) and he achieved full donor engraftment with no chronic GVHD.

Figure 9:
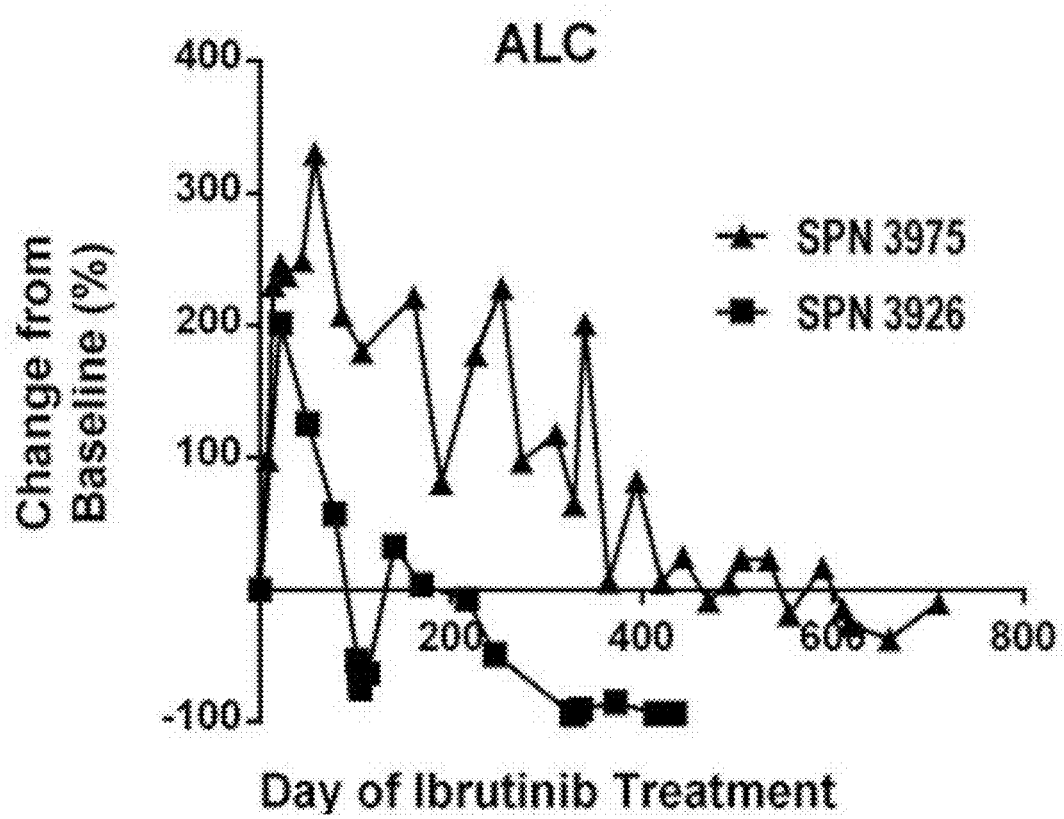
FIG. 9 Panels A-E shows plots depicting percent change in absolute lymphocytic count (ALC) for 2 patients who received ibrutinib treatment for >1 yr. SPN=Stanford Patient Number (Panel A); percent reduction in LN size, as reported by the sum of the product of LN diameters (SPD) for 4 patients following initiation of ibrutinib (Panel B); CLL MRD (reported as a percentage of WBCs) and blood donor CD3 T cell levels shown for patient SPN 3975 (Panel C); B cells (excluding the CLL clone) as percent of total PBMC for patient SPN 3975 as measured by IgH HTS (Panel D); Total IgH molecules and unique IgH clone counts for patient SPN 3975 at different time points (D=day) post allo-HCT (Panel E).
Figure 9:
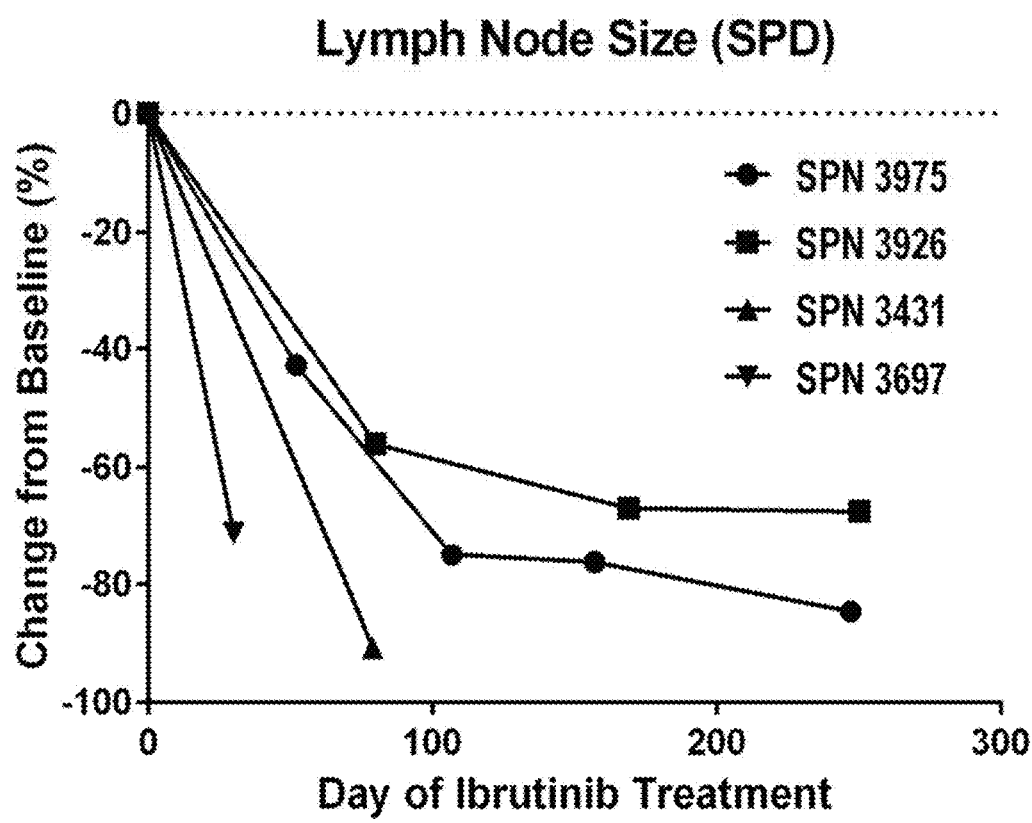
Figure 9:
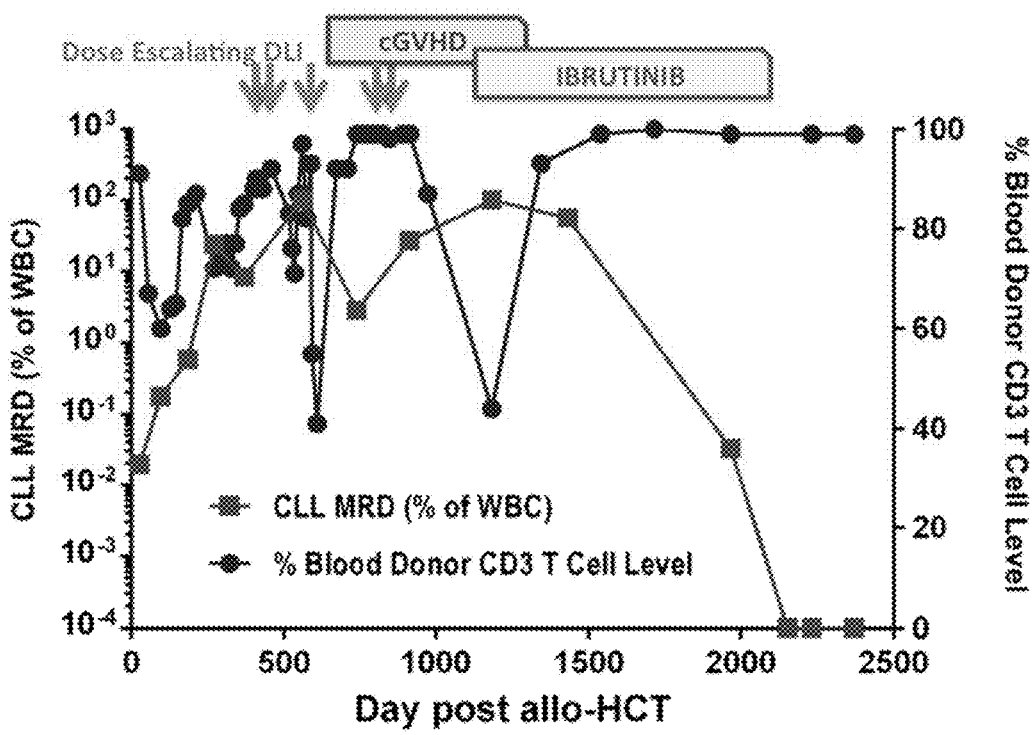
Figure 9:
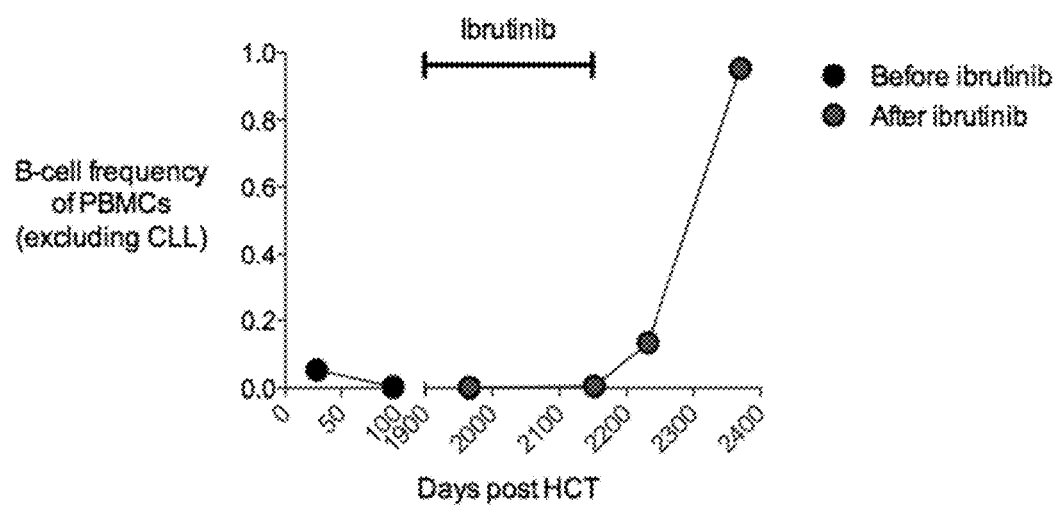
Figure 9:
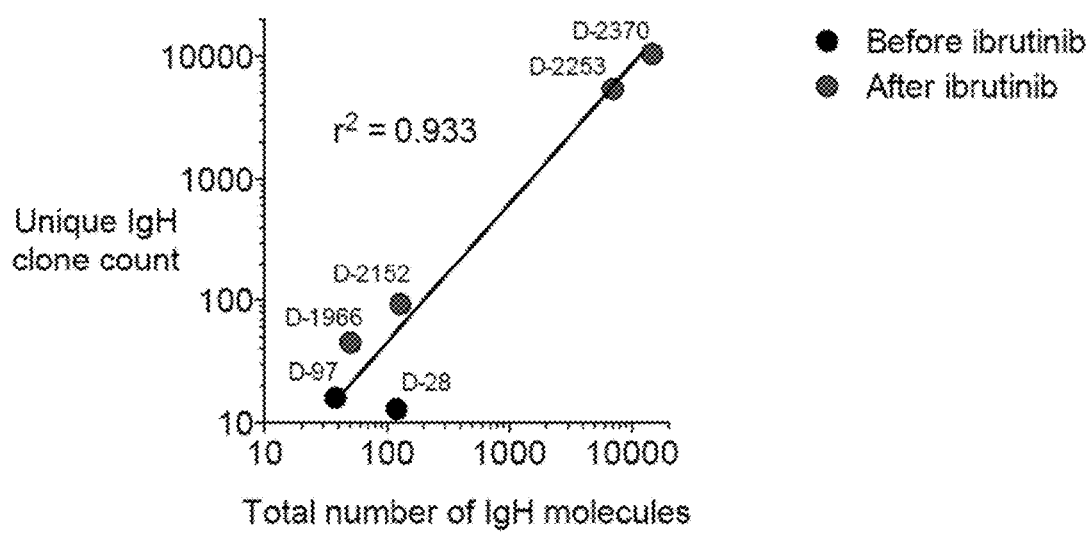

Example 7: Ibrutinib Treatment of Relapsed CLL Following Allogeneic Transplantation: Sustained Disease Response and Promising Donor Immune Modulation This example demonstrates the effects of ibrutinib salvage therapy in 5 CLL patients who relapsed following allogeneic hematopoietic cell transplantation (allo-HCT). In addition to minimal residual disease (MRD) response measurements, donor T cell chimerism and donor B cell immune reconstitution following ibrutinib therapy were also assessed. Five patients with high-risk CLL relapsed 1-8.5 yrs following allo-HCT. Four patients had never achieved donor CD3 T cell chimerism >95% following reduced-intensity transplant. Ibrutinib 420 mg daily was started 1 mo-2 yrs after clinical relapse. Four of the 5 patients remained on ibrutinib with treatment courses ranging from 3-17 mos. CLL MRD was measured by IgH high-throughput sequencing (HTS) using the CLONOSIGHT minimal residual disease test (Sequenta, Inc.), which has the sensitivity to detect 1 CLL clone per million leukocytes. Lymph node (LN) size was assessed by CT scan and reported as the sum of the products of the LN diameters (SPD). Donor B cell reconstitution was determined by IgH HTS quantification of total IgH molecules and unique IgH clonotypes. Lymphocytosis was observed in all 5 patients following initiation of ibrutinib treatment, consistent with previous reports. In 2 patients who received >1 yr of ibrutinib treatment, lymphocytosis peaked at 3 wks and 8 wks after initiation of treatment and slowly declined thereafter, fully resolving within 1 yr (FIG. 9A). All 4 patients with pathologic lymphadenopathy prior to treatment experienced dramatic LN reduction (FIG. 9B; 68% average reduction in LN size after 3 months on ibrutinib). The longest duration of follow-up was reported for patient SPN 3975, who had a 17p deletion and received ibrutinib for 39 months. Treatment was discontinued after CLL MRD became undetectable by CLONOSIGHT minimal residual disease test (FIG. 9C). Evidence of donor T cell immune modulation included achievement of full donor CD3 chimerism after 1 year and resolution of oral and skin chronic graft-versus-host disease (GVHD) after 6 months. Although this patient has been off ibrutinib for >8 months, full donor chimerism persisted and CLL MRD remained undetectable (FIG. 9C). Before ibrutinib treatment, donor B cells (excluding the patient's CLL clone) accounted for <0.2% of total PBMC as determined by IgH HTS. Following discontinuation of ibrutinib, the percentage of donor B cells increased within 6 months to >1% of PBMC (FIG. 9D). Furthermore, recovering B cells had diverse, low frequency IgH clonotypes (FIG. 9E). Together, these findings show rapid, sustained, and diverse immune reconstitution without CLL recurrence following ibrutinib discontinuation. Ibrutinib provided effective salvage therapy for CLL relapse following allo-HCT. Post-transplant CLL relapse is often extra-nodal and our experience shows ibrutinib is effective in clearing both nodal and extra-nodal disease. One patient who stopped therapy after achieving MRD negativity maintains undetectable disease 8 months following ibrutinib discontinuation. Ibrutinib treatment demonstrated promising donor immune modulation by promoting full donor chimerism and resolution of chronic GVHD. These data supported using ibrutinib in relapsed CLL patients following allo-HCT.

Example 8: Safety and Efficacy of Ibrutinib in Patients with Relapsed/Refractory (R/R) Chronic Lymphocytic Leukemia (CLL)/Small Lymphocytic Lymphoma (SLL) Who have Undergone Prior Allogeneic Stem Cell Transplant Patients with CLL who relapse after allogeneic hematopoietic stem cell transplantation (alloHCT) are difficult to treat with chemotherapy due to impaired hematopoietic reserve, infections, and concern for graft-versus-host disease (GVHD). Ibrutinib is approved in the USA for patients with CLL or MCL who have received ≥1 prior therapy, and for patients with CLL with del17p. In preclinical studies, ibrutinib reversed established chronic GVHD (cGVHD). The safety and efficacy of ibrutinib in a subset of patients with prior alloHCT were evaluated in this example. Data were collected for R/R patients with prior allogeneic HSCT enrolled in 1 of 4 clinical trials (PCYC-1102, PCYC-1109, PCYC-1112, and PCYC-1117). PCYC-1112 and PCYC-1117 only enrolled patients >6 months post-HCT and without GVHD. Efficacy evaluations included overall response rate (ORR; iwCLL criteria), duration of response (DOR), progression-free survival (PFS), and overall survival (OS). Safety evaluations included adverse events (AEs), including serious AEs (SAEs). 16 patients from 4 clinical trials had prior alloHCT (median age, 54.5 y; 16 patients with ECOG performance status 0 or 1; 10 patients with del17p, 3 patients with del11q, 12 patients with ≥4 prior therapies). Median time since the most recent HCT was 27 months (range, 8-115). Baseline neutropenia, anemia, and thrombocytopenia were reported in 31%, 25%, and 38%, respectively. Median time on ibrutinib was 18.1 months (range, 0.4-38.8), with 12 patients being treated for >12 months. At data cut-off, 11 patients were continuing treatment. Reasons for discontinuation included disease progression (n=2), AEs (n=2), and consent withdrawal (n=1). Investigator-assessed responses included 2 complete responses, 9 partial responses (PRs), and 3 PRs with lymphocytosis, resulting in a best ORR of 87.5%. Median DOR, PFS, and OS were not reached at a median follow-up of 23 months. The 24-month PFS and OS rates were 77% and 75%, respectively. Treatment-emergent grade ≥3 SAEs were observed in 11 patients and included infections (n=6), and febrile neutropenia, atrial flutter, colitis, perirenal hematoma, subdural hematoma, postprocedural hemorrhage, hypercalcemia, bone lesion, syncope, hematuria, urinary retention, and dyspnea (n=1 each, some events reported for the same patient). The only AE leading to ibrutinib discontinuation was pneumonia (n=2); both were fatal events. Two additional deaths occurred on study due to disease progression at 24 and 28 months. Ibrutinib was well tolerated in patients who had prior alloHCT, with a safety profile similar to that observed in the overall R/R CLL population. Best ORR (87.5%) was consistent with results observed in the overall/broader population.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating refractory chronic graft versus host disease (GVHD) comprising orally administering 420 mg of ibrutinib once per day to an adult human patient having chronic GVHD refractory to systemic therapy, wherein the adult human patient achieves a complete response (CR), wherein the CR is a complete resolution of symptoms attributable to chronic GVHD.

2. The method of claim 1, wherein the adult human had a hematopoietic cell transplantation.

3. The method of claim 1, wherein the refractory chronic GVHD is steroid-resistant chronic GVHD.

4. The method of claim 1, wherein the refractory chronic GVHD is cyclosporin-resistant chronic GVHD.

* * * * *

```
SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 1

Ala Val Leu Glu Ser Glu Glu Glu Leu Tyr Ser Ser Ala Arg Gln
1               5                   10                  15
```